(12) United States Patent
Kühnemund et al.

(10) Patent No.: US 11,555,219 B2
(45) Date of Patent: Jan. 17, 2023

(54) METHOD OF DETECTING TARGET NUCLEIC ACID MOLECULES

(71) Applicant: 10x Genomics, Inc., Pleasanton, CA (US)

(72) Inventors: Malte Kühnemund, Solna (SE); Toon Verheyen, Solna (SE)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

(21) Appl. No.: 17/335,931

(22) Filed: Jun. 1, 2021

(65) Prior Publication Data

US 2021/0340618 A1 Nov. 4, 2021

Related U.S. Application Data

(63) Continuation of application No. PCT/EP2020/065090, filed on May 29, 2020.

(30) Foreign Application Priority Data

May 31, 2019 (GB) ...................... 1907752
May 31, 2019 (GB) ...................... 1907764

(Continued)

(51) Int. Cl.
*C12Q 1/6844* (2018.01)
*C12Q 1/6874* (2018.01)
(Continued)

(52) U.S. Cl.
CPC .......... *C12Q 1/6874* (2013.01); *C12Q 1/6813* (2013.01); *C12Q 1/6816* (2013.01); *C12Q 1/6844* (2013.01); *C12Q 2537/1373* (2013.01)

(58) Field of Classification Search
None
See application file for complete search history.

(56) References Cited

U.S. PATENT DOCUMENTS

| 4,883,867 A | 11/1989 | Lee et al. |
| 5,200,314 A | 4/1993 | Urdea |

(Continued)

FOREIGN PATENT DOCUMENTS

| WO | WO-2011/100617 A2 | 8/2011 |
| WO | WO-2016/138500 A1 | 9/2016 |

(Continued)

OTHER PUBLICATIONS

Duose et al., "Configuring robust DNA strand displacement reactions for in situ molecular analyses," Nucleic Acids Res. (2012) 40(7): 3289-3298.

(Continued)

*Primary Examiner* — Robert T. Crow
(74) *Attorney, Agent, or Firm* — Morrison & Foerster LLP

(57) ABSTRACT

The present application provides methods for detecting a nucleic acid molecule involving the use of a signal code sequence which corresponds to said nucleic acid molecule and a plurality of labelled detection probes which yield signals which make up the signal code sequence. In particular, the invention provides a sequential barcoding and decoding scheme which utilises a sequencing-by-hybridisation (SBH) strategy to sequence and decode a nucleotide barcode sequence, and to differentiate the nucleotide barcode sequence from other nucleotide barcode sequences. In an extension of the method, the application also provides a new coding scheme for providing a target nucleic acid with a detectable "colour" (or similar signal)-based code.

17 Claims, 23 Drawing Sheets

Specification includes a Sequence Listing.

(30) Foreign Application Priority Data

May 31, 2019 (GB) .................................... 1907772
May 31, 2019 (GB) .................................... 1907779

(51) Int. Cl.
C12Q 1/6813 (2018.01)
C12Q 1/6816 (2018.01)

(56) References Cited

U.S. PATENT DOCUMENTS

| | | | |
|---|---|---|---|
| 5,648,245 A * | 7/1997 | Fire | C12N 15/10 435/91.1 |
| 5,695,940 A | 12/1997 | Drmanac et al. | |
| 6,306,597 B1 | 10/2001 | Macevicz | |
| 6,534,266 B1 | 3/2003 | Singer | |
| 6,855,523 B2 | 2/2005 | Zhang et al. | |
| 7,255,994 B2 | 8/2007 | Lao | |
| 7,473,767 B2 | 1/2009 | Dimitrov | |
| 7,534,991 B2 | 5/2009 | Miller et al. | |
| 7,555,155 B2 | 6/2009 | Levenson et al. | |
| 7,655,898 B2 | 2/2010 | Miller | |
| 7,700,323 B2 * | 4/2010 | Willis | C12Q 1/6827 435/91.1 |
| 7,910,304 B2 | 3/2011 | Drmanac | |
| 7,941,279 B2 | 5/2011 | Hwang et al. | |
| 7,989,166 B2 | 8/2011 | Koch et al. | |
| 8,124,751 B2 | 2/2012 | Pierce et al. | |
| 8,199,999 B2 | 6/2012 | Hoyt et al. | |
| 8,268,554 B2 | 9/2012 | Schallmeiner | |
| 8,330,087 B2 | 12/2012 | Domenicali | |
| 8,415,102 B2 | 4/2013 | Geiss et al. | |
| 8,431,691 B2 | 4/2013 | McKernan et al. | |
| 8,462,981 B2 | 6/2013 | Determan et al. | |
| 8,481,258 B2 | 7/2013 | Church et al. | |
| 8,519,115 B2 | 8/2013 | Webster et al. | |
| 8,551,710 B2 | 10/2013 | Bernitz et al. | |
| 8,658,361 B2 | 2/2014 | Wu et al. | |
| 8,771,950 B2 | 7/2014 | Church et al. | |
| 8,986,926 B2 | 3/2015 | Ferree et al. | |
| 9,201,063 B2 | 12/2015 | Sood et al. | |
| 9,273,349 B2 | 3/2016 | Nguyen et al. | |
| 9,371,563 B2 | 6/2016 | Geiss et al. | |
| 9,371,598 B2 | 6/2016 | Chee | |
| 9,376,717 B2 | 6/2016 | Gao et al. | |
| 9,541,504 B2 | 1/2017 | Hoyt | |
| 9,551,032 B2 | 1/2017 | Landegren et al. | |
| 9,624,538 B2 | 4/2017 | Church et al. | |
| 9,714,446 B2 | 7/2017 | Webster et al. | |
| 9,714,937 B2 | 7/2017 | Dunaway | |
| 9,727,810 B2 | 8/2017 | Fodor et al. | |
| 9,778,155 B2 | 10/2017 | Gradinaru et al. | |
| 9,783,841 B2 | 10/2017 | Nolan et al. | |
| 9,909,167 B2 | 3/2018 | Samusik et al. | |
| 10,032,064 B2 | 7/2018 | Hoyt | |
| 10,059,990 B2 | 8/2018 | Boyden et al. | |
| 10,126,242 B2 | 11/2018 | Miller et al. | |
| 10,179,932 B2 | 1/2019 | Church et al. | |
| 10,227,639 B2 | 3/2019 | Levner et al. | |
| 10,246,700 B2 | 4/2019 | Dunaway et al. | |
| 10,266,888 B2 | 4/2019 | Daugharthy et al. | |
| 10,267,808 B2 | 4/2019 | Cai | |
| 10,309,879 B2 | 6/2019 | Chen et al. | |
| 10,317,321 B2 | 6/2019 | Tillberg et al. | |
| 10,364,457 B2 | 7/2019 | Wassie et al. | |
| 10,370,698 B2 | 8/2019 | Nolan et al. | |
| 10,415,080 B2 | 9/2019 | Dunaway et al. | |
| 10,457,980 B2 | 10/2019 | Cai et al. | |
| 10,465,235 B2 | 11/2019 | Gullberg et al. | |
| 10,494,662 B2 | 12/2019 | Church et al. | |
| 10,495,554 B2 | 12/2019 | Deisseroth et al. | |
| 10,501,777 B2 | 12/2019 | Beechem et al. | |
| 10,501,791 B2 | 12/2019 | Church et al. | |
| 10,510,435 B2 | 12/2019 | Cai et al. | |
| 10,526,649 B2 | 1/2020 | Chen et al. | |
| 10,545,075 B2 | 1/2020 | Deisseroth et al. | |
| 10,580,128 B2 | 3/2020 | Miller | |
| 10,640,816 B2 | 5/2020 | Beechem et al. | |
| 10,640,826 B2 | 5/2020 | Church et al. | |
| 10,669,569 B2 | 6/2020 | Gullberg et al. | |
| 10,746,981 B2 | 8/2020 | Tomer et al. | |
| 10,774,372 B2 | 9/2020 | Chee et al. | |
| 10,774,374 B2 | 9/2020 | Frisén et al. | |
| 10,794,802 B2 | 10/2020 | Gradinaru et al. | |
| 10,802,262 B2 | 10/2020 | Tomer et al. | |
| 10,815,519 B2 | 10/2020 | Husain et al. | |
| 10,844,426 B2 | 11/2020 | Daugharthy et al. | |
| 10,858,698 B2 | 12/2020 | Church et al. | |
| 10,872,679 B2 | 12/2020 | Cai et al. | |
| 10,964,001 B2 | 3/2021 | Miller | |
| 2011/0223585 A1 | 9/2011 | Gullberg et al. | |
| 2013/0288249 A1 | 10/2013 | Gullbert | |
| 2013/0323729 A1 | 12/2013 | Landegren et al. | |
| 2013/0344508 A1 * | 12/2013 | Schwartz | C12Q 1/6804 435/7.21 |
| 2014/0342354 A1 * | 11/2014 | Evans | C12Q 1/6827 435/6.11 |
| 2016/0108458 A1 | 4/2016 | Frei et al. | |
| 2016/0305856 A1 | 10/2016 | Boyden et al. | |
| 2016/0376642 A1 | 12/2016 | Landegren et al. | |
| 2017/0009278 A1 | 1/2017 | Söderberg et al. | |
| 2017/0029872 A1 | 2/2017 | Bhattacharyya et al. | |
| 2017/0081489 A1 | 3/2017 | Rodrigues et al. | |
| 2017/0101672 A1 | 4/2017 | Luo et al. | |
| 2017/0220733 A1 | 8/2017 | Zhuang et al. | |
| 2017/0253918 A1 | 9/2017 | Kohman | |
| 2018/0052081 A1 | 2/2018 | Kohman | |
| 2018/0080876 A1 | 3/2018 | Rockel et al. | |
| 2018/0142286 A1 * | 5/2018 | Dunaway | C12Q 1/6869 |
| 2018/0208967 A1 | 7/2018 | Larman et al. | |
| 2018/0237864 A1 | 8/2018 | Imler et al. | |
| 2018/0320226 A1 | 11/2018 | Church et al. | |
| 2019/0017106 A1 | 1/2019 | Frisen et al. | |
| 2019/0032128 A1 | 1/2019 | Chen et al. | |
| 2019/0055594 A1 | 2/2019 | Samusik et al. | |
| 2019/0112599 A1 | 4/2019 | Church et al. | |
| 2019/0119735 A1 | 4/2019 | Deisseroth et al. | |
| 2019/0155835 A1 | 5/2019 | Daugharthy et al. | |
| 2019/0161796 A1 | 5/2019 | Hauling et al. | |
| 2019/0177718 A1 | 6/2019 | Church et al. | |
| 2019/0194709 A1 | 6/2019 | Church et al. | |
| 2019/0218608 A1 | 7/2019 | Daugharthy et al. | |
| 2019/0249248 A1 | 8/2019 | Beechem et al. | |
| 2019/0264270 A1 | 8/2019 | Zhuang et al. | |
| 2019/0271028 A1 | 9/2019 | Khafizov et al. | |
| 2019/0276881 A1 | 9/2019 | Zhuang et al. | |
| 2019/0339203 A1 | 11/2019 | Miller et al. | |
| 2020/0010891 A1 | 1/2020 | Beechem et al. | |
| 2020/0071751 A1 | 3/2020 | Daugharthy et al. | |
| 2020/0123597 A1 | 4/2020 | Daniel | |
| 2020/0140920 A1 | 5/2020 | Pierce et al. | |
| 2020/0224243 A1 | 7/2020 | Desai et al. | |
| 2020/0224244 A1 | 7/2020 | Nilsson et al. | |
| 2020/0239946 A1 | 7/2020 | Dewal | |
| 2020/0332368 A1 | 10/2020 | Ferree et al. | |
| 2020/0354774 A1 | 11/2020 | Church et al. | |
| 2020/0354782 A1 | 11/2020 | Dewal | |
| 2020/0362398 A1 | 11/2020 | Kishi et al. | |
| 2020/0393343 A1 | 12/2020 | Kennedy-Darling et al. | |
| 2021/0017587 A1 | 1/2021 | Cai et al. | |
| 2021/0115504 A1 | 4/2021 | Cai et al. | |
| 2022/0083832 A1 | 3/2022 | Shah | |
| 2022/0084628 A1 | 3/2022 | Shah | |
| 2022/0084629 A1 | 3/2022 | Shah | |
| 2022/0136049 A1 | 5/2022 | Bava et al. | |
| 2022/0186300 A1 | 6/2022 | Bava | |
| 2022/0195498 A1 | 6/2022 | Kuhnemund et al. | |
| 2022/0213529 A1 | 7/2022 | Kuhnemund et al. | |
| 2022/0228200 A1 | 7/2022 | Bava | |

FOREIGN PATENT DOCUMENTS

| | | |
|---|---|---|
| WO | WO-2017/143155 A2 | 8/2017 |
| WO | WO-2017/222453 A1 | 12/2017 |
| WO | WO-2019/199579 A1 | 10/2019 |

(56) References Cited

FOREIGN PATENT DOCUMENTS

| WO | WO-2020/076976 A1 | 4/2020 |
|---|---|---|
| WO | WO-2020/076979 A1 | 4/2020 |
| WO | WO-2020/096687 A1 | 5/2020 |
| WO | WO-2020/099640 A1 | 5/2020 |
| WO | WO-2020/117914 A1 | 6/2020 |
| WO | WO 2020/123316 | 6/2020 |
| WO | WO-2020/123742 A1 | 6/2020 |
| WO | WO-2020/142490 A1 | 7/2020 |
| WO | WO-2020/240025 A1 | 12/2020 |
| WO | WO-2020/254519 A1 | 12/2020 |
| WO | WO 2021/123282 | 6/2021 |
| WO | WO 2021/123286 | 6/2021 |
| WO | WO 2021/155063 | 8/2021 |
| WO | WO 2021/168326 | 8/2021 |

OTHER PUBLICATIONS

Goh, J.J.L. et al. (Jul. 2020, e-pub. Jun. 15, 2020). "Highly Specific Multiplexed RNA Imaging In Tissues With Split-FISH," Nat Methods 17(7):689-693. doi: 10.1038/s41592-020-0858-0. Epub Jun. 15, 2020.
Goransson et al., "A single molecule array for digital targeted molecular analyses," Nucleic Acids Res. 2009 37(1):e7. doi: 10.1093/nar/gkn921.
Liu et al. Barcoded oligonucleotides ligated on RNA amplified for multiplexed and parallel in situ analyses. Nucleic Acids Res. (2021) 49(10):e58, 15 pages, doi 10.1093/nar/gkab120.
McGinn et al., "New technologies for DNA analysis—a review of the READNA Project," N Biotechnol. (2016) 33(3): 311-30. doi: 10.1016/j.nbt.2015.10.003.
Payne et al. "In situ genome sequencing resolves DNA sequence and structure in intact biological samples," Science. (2021) 371(6532): eaay3446. doi:10.1126/science.aay3446. Epub Dec. 31, 2020.
Peng, "Sequential Color Display for Highly Multiplexed in situ Single-Molecule Detection," Dissertation for Doctor of Philosophy, Stanford University; Jun. 2017; 116 pgs.
Rouhanifard et al. "ClampFISH detects individual nucleic acid molecules using click chemistry-based amplification," Nat Biotechnol. (2018) 17 pages, doi: 10.1038/nbt.4286.
Takei et al., (Feb. 2021, e-pub Jan. 27, 2021). "Integrated Spatial Genomics Reveals Global Architecture Of Single Nuclei," Nature 590(7845):344-350, 53 pages, doi 10.1038/S41586-020-03126-2.
Wu, C. et al. (Nov. 28, 2018). "RollFISh Achieves Robust Quantification Of Single-Molecule RNA Biomarkers In Paraffin-Embedded Tumor Tissue Samples," Commun Biol. 1:(209):1-8. doi: 10.1038/s42003-018-0218-0.
Xiao et al., "Single-Cell in Situ RNA Analysis With Switchable Fluorescent Oligonucleotides," Front Cell Dev Biol. (2018) 6:42.
Zhang et al., "Droplet-Based Digital Ratiometric Fluorescence Coding for Multiplex Nucleic Acid Amplification Testing," 2019 IEEE 32nd International Conference on Micro Electro Mechanical Systems (MEMS) (2019): pp. 588-591, doi 10.1109/MEMSYS.2019.8870782.
Bibikova et al., "Quantitative gene expression profiling in formalin-fixed, paraffin-embedded tissues using universal bead arrays," Am J Pathol. Nov. 2004;165(5):1799-807.
Capodieci et al. "Gene expression profiling in single cells within tissue," Nat Methods. (2005) 2(9): 663-5.
Conze et al., "Single molecule analysis of combinatorial splicing," Nucleic Acids Res. (2010) 38(16): e163.
Femino et al., "Visualization of single RNA transcripts in situ," Science. (1998) 280(5363): 585-90.
Gavrilovic et al., "Automated classification of multicolored rolling circle products in dual-channel wide-field fluorescence microscopy," Cytometry A. (2011) 79(7): 518-27.
Geiss et al., "Direct multiplexed measurement of gene expression with color-coded probe pairs," Nat Biotechnol. (2008) 26(3): 317-25.
Gunderson et al. "Decoding randomly ordered DNA arrays." Genome research 14.5 (2004): 870-877.
Han et al., "Quantum-dot-tagged microbeads for multiplexed optical coding of biomolecules," Nat Biotechnol. (2001) 19(7): 631-5.
Itkovitz et al., "Validating Transcripts with Probes and Imaging Technology," Nat Methods. (2011) 8(4 Suppl): S12-S19.
Itkovitz et al., "Single-molecule transcript counting of stem-cell markers in the mouse intestine," Nat Cell Biol. (2011) 14(1): 106-14.
Lagunavicius et al., "Novel application of Phi29 DNA polymerase: RNA detection and analysis in vitro and in situ by target RNA-primed RCA," RNA. (2009) 15(5):765-71.
Larsson et al. "In situ detection and genotyping of individual mRNA molecules," Nat Methods. (2010) 7(5):395-397.
Levsky et al., "Fluorescence in situ hybridization: past, present and future," J Cell Sci. (2003) 116(Pt 14): 2833-8.
Levsky et al., "Single-cell gene expression profiling," Science. (2002) 297(5582): 836-40.
Maierhorfer et al., "Multicolor deconvolution microscopy of thick biological specimens," Am J Pathol. (2003) 162(2): 373-9.
Meade et al. "Multiplexed DNA detection using spectrally encoded porous SiO2 photonic crystal particles," Anal Chem. (2009) 81(7): 2618-25.
Raj et al., "Imaging individual mRNA molecules using multiple singly labeled probes," Nat Methods. (2008) 5(10): 877-879.
Sun et al., "Composite organic-inorganic nanoparticles as Raman labels for tissue analysis," Nano Lett. (2007) 7(2): 351-6.
Tsanov et al., "smiFISH and FISH-quant—a flexible single RNA detection approach with super-resolution capability," Nucleic Acids Res. (2016) 15;44(22): e165.
Wählby et al., "Sequential immunofluorescence staining and image analysis for detection of large Nos. of antigens in individual cell nuclein," Cytometry. (2002) 47(1): 32-41.
Weibrecht et al., "Simultaneous visualization of both signaling cascade activity and end-point gene expression in single cells," PLoS One. (2011) 6(5): e20148.
Wilson et al., "Encoded microcarriers for high-throughput multiplexed detection," Angew Chern Int Ed Engl. (2006) 18;45(37): 6104-17.
Zhao et al., "Advances of multiplex and high throughput biomolecular detection technologies based on encoding microparticles," Sci China Chem. (2011) 54(8):1185.

* cited by examiner

G

Remove BC 2
Interrogation
Probes cocktail

A

SEQUENCE LISTING

```
<160> NUMBER OF SEQ ID NOS: 10

<210> SEQ ID NO 1
<211> LENGTH: 95
<212> TYPE: DNA
<213> ORGANISM: Artificial Sequence
<220> FEATURE:
<223> OTHER INFORMATION: Padlock probe
```

<400> SEQUENCE: 1
agcctcgcct tgccttttc tacgattta ccagtggctt tgcgtctat ttagtggagc    60 ctaacgctag actatctttc gccccgcgag cacag                              95

<210> SEQ ID NO 2
<211> LENGTH: 30
<212> TYPE: DNA
<213> ORGANISM: Artificial Sequence
<220> FEATURE:
<223> OTHER INFORMATION: Template

<400> SEQUENCE: 2
ggcaaaggcg aggctctgtg ctcgcggggc                                    30

<210> SEQ ID NO 3
<211> LENGTH: 46
<212> TYPE: DNA
<213> ORGANISM: Artificial Sequence
<220> FEATURE:
<223> OTHER INFORMATION: SBH oligonucleotide

<400> SEQUENCE: 3
cacatgcgtc tatgtagtgg agccttagag agtagtactt ccgact                  46

<210> SEQ ID NO 4
<211> LENGTH: 49
<212> TYPE: DNA
<213> ORGANISM: Artificial Sequence
<220> FEATURE:
<223> OTHER INFORMATION: SBH oligonucleotide

<400> SEQUENCE: 4
cacatgcgtc tatatagtgg agccttgtag tacagcagca gcattgagg               49

<210> SEQ ID NO 5
<211> LENGTH: 47
<212> TYPE: DNA
<213> ORGANISM: Artificial Sequence
<220> FEATURE:
<223> OTHER INFORMATION: SBH oligonucleotide

<400> SEQUENCE: 5
cacatgcgtc tatttagtgg agccttcaat ctagtatcag tggcgca                 47

<210> SEQ ID NO 6
<211> LENGTH: 46
<212> TYPE: DNA
<213> ORGANISM: Artificial Sequence
<220> FEATURE:
<223> OTHER INFORMATION: SBH oligonucleotide

<400> SEQUENCE: 6
cacatgcgtc tatctagtgg agccttgggc cttattccgg tgctat                  46

<210> SEQ ID NO 7
<211> LENGTH: 20
<212> TYPE: DNA
<213> ORGANISM: Artificial Sequence
<220> FEATURE:
<223> OTHER INFORMATION: Detection probe
<220> FEATURE:
<221> NAME/KEY: misc_feature
<222> LOCATION: (1)..(1)
<223> OTHER INFORMATION: Cy3

```
<400> SEQUENCE: 7
agtcggaagt actactctct                                              20

<210> SEQ ID NO 8
<211> LENGTH: 23
<212> TYPE: DNA
<213> ORGANISM: Artificial Sequence
<220> FEATURE:
<223> OTHER INFORMATION: Detection probe
<220> FEATURE:
<221> NAME/KEY: misc_feature
<222> LOCATION: (1)..(1)
<223> OTHER INFORMATION: Cy5

<400> SEQUENCE: 8
cctcaatgct gctgctgtac tac                                          23

<210> SEQ ID NO 9
<211> LENGTH: 21
<212> TYPE: DNA
<213> ORGANISM: Artificial Sequence
<220> FEATURE:
<223> OTHER INFORMATION: Detection probe
<220> FEATURE:
<221> NAME/KEY: misc_feature
<222> LOCATION: (1)..(1)
<223> OTHER INFORMATION: AF488

<400> SEQUENCE: 9
tgcgccactg atactagatt g                                            21

<210> SEQ ID NO 10
<211> LENGTH: 20
<212> TYPE: DNA
<213> ORGANISM: Artificial Sequence
<220> FEATURE:
<223> OTHER INFORMATION: Detection probe
<220> FEATURE:
<221> NAME/KEY: misc_feature
<222> LOCATION: (1)..(1)
<223> OTHER INFORMATION: TexR

<400> SEQUENCE: 10
atagcaccgg aataaggccc                                              20
```

METHOD OF DETECTING TARGET NUCLEIC ACID MOLECULES

CROSS-REFERENCE TO RELATED APPLICATIONS

This application is a continuation of International Application No. PCT/EP2020/065090 filed on May 29, 2020, which claims benefit of United Kingdom patent application Nos. GB 1907764.3 filed May 31, 2019, GB 1907752.8 filed May 31, 2019, GB 1907779.1 filed May 31, 2019, and GB 1907772.6 filed May 31, 2019, and the disclosures of each of these applications are hereby incorporated herein by reference in their entirety for all purposes.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 202412008501SubSeqList.TXT, date recorded: Jul. 13, 2021, size: 2.59 KB).

The present invention relates to a method for reading or decoding a nucleotide barcode sequence. In particular, the invention provides a sequential barcoding and decoding scheme which utilises a sequencing-by-hybridisation (SBH) strategy to sequence and decode the barcode, and to differentiate the nucleotide barcode sequence from other nucleotide barcode sequences. The invention is based on novel designs for the barcode sequence and the detection probes which hybridise to the barcode sequence to sequence the barcode. In an extension of the method, the invention also includes a new coding scheme for providing a target nucleic acid with a detectable "colour" (or similar signal)-based code. Also disclosed herein are more general methods for detecting target nucleic acid molecules.

Nucleotide barcoding systems are used in a wide range of applications where it is desired to detect and/or quantify specific nucleic acid molecules, such as transcription profiling and sequencing methods, or indeed in any nucleic acid analysis method where it is desired to detect and differentiate multiple different nucleic acids, including for example in diagnostic applications. In short, the nucleic acid sequences that are to be detected or identified are each assigned a unique barcode sequence. At its simplest a barcode may be detected by a detection probe which is designed to hybridise specifically to a given barcode sequence. However, alternatively, various sequencing strategies may be employed to sequence, and thereby identify, the barcode sequence, including by SBH. Broadly, SBH involves the use of hybridisation probes which are designed to hybridise to, and detect, a specific base or a specific sequence to detect and assemble the sequence which is present in a target nucleic acid molecule. In a SBH strategy the barcode sequences can be decoded or "read" using complementary labelled detection probes, by observing which labelled detection probes hybridise to the barcode sequence. Typically, in SBH each detection probe is designed to sequence or "read" one base at a time; a set of 4 probes comprises a different base at the position complementary to the base to be sequenced and it is detected which of the set of probes for that position is hybridised. The sequences in the detection probe flanking the detection position may be complementary to the reference sequence for the target to allow the probe to hybridise to the target, or more typically for decoding a barcode they may be degenerate. Accordingly, a barcode may commonly, although not necessarily, comprise a continuous sequence of bases, each single base corresponding to a position of the barcode, and a series of detection probes are used to sequence (read) the individual bases of the barcode sequence. The identity of the barcode sequence, and therefore of the associated nucleic acid molecule can thus be determined. A discontinuous barcode, wherein the barcode positions are not contiguous, and/or a barcode where a barcode position may comprise more than one base, may similarly be read using a series of sets of detection probes designed to read each barcode position.

The barcode sequence may be provided directly within a target molecule, for example it may be linked directly to a target nucleic acid molecule, for example by ligation, or it may be incorporated, for example into an amplification product, e.g. by the use of a primer containing the barcode sequence, or it, or its complement, may simply be provided as part of a target molecule, e.g. where the target molecule is a probe or some other synthetic molecule. Alternatively, intermediate or "sandwich" probes which hybridise to the target nucleic acid molecule may be used indirectly to introduce, or provide, a barcode. These probes typically comprise a sequence complementary to a portion of their respective target nucleic acid molecules, and a separate, non-target complementary sequence, which contains the barcode.

These intermediate or sandwich probes may be in the form of so-called "L-probes". The L-probe is the simplest version of the sandwich probe design. It consists of two parts, a first part comprising the target nucleic acid recognition site, which binds the target nucleic acid molecule directly, and a second part which does not hybridise to the target molecule and which consequently forms a single-stranded overhang when the probe is hybridised, and which contains the barcode sequence, and thus a binding site for a detection probe. The probes may thus be thought of as forming an L shape when hybridised to the target nucleic acid molecule. The barcode may be a continuous sequence (e.g. a contiguous series of bases) or it may be represented by two or more separate binding sites for detection probes, which are separately provided in the overhang sequence.

As a modification of the L-probe, the sandwich probe may have a "U-probe" design wherein the target recognition site is flanked by two sequences which are non-target complementary sequences, and which contain sequences making up the barcode. Having two rather than one flanking sequence (as in the L-probe) allows coding capacity to be increased.

The coding capacity of a nucleotide barcoding system using continuous barcode sequences, i.e. the number of different barcode sequences that can be generated, and therefore the number of different nucleic acid sequences that can be distinguished, is limited by the length of the barcode sequence. For a system using barcode sequences that are n nucleotides in length, the number of possible barcode sequences is $4^n$. Accordingly, in applications where a high degree of multiplicity is required, that is to say, where it is necessary to distinguish between a large number of nucleic acid sequences, it is necessary to increase the length of the barcode sequence in order to assign each nucleic acid sequence a unique barcode. The use of longer barcode sequences can cause problems with the specificity of the decoding system, as off-site binding of detection probes becomes more common when the system comprises multiple lengthy barcode sequences which only differ by a single nucleotide.

In addition, the number of different barcode sequences that can be identified may be limited by the number of different labels that are available. If it is necessary to distinguish between a large number of nucleic acid sequences, it may not be feasible to have a differently labelled probe for each sequence. Accordingly, many barcoding methods use a limited pool of labels, and require multiple detection cycles in order to decode the barcode sequences. These methods thus involve repeatedly hybridising a labelled detection probe, imaging the sample to detect the label that has been hybridised, and removing the hybridised labelled detection probe so that the next cycle can begin. In this way, a specified sequence of labels can be detected, e.g. a sequence of colours which have been detected, forming a code made up of the labels (e.g. a "colour-code" made up of fluorophore labels) which distinguishes a particular (i.e. target) nucleic acid.

The process of removing or dehybridising the hybridised labelled detection probe once it has been imaged can be difficult, and thus this step often involves the use of high temperature and/or potentially toxic chemical agents such as formamide to denature or disrupt the hybrid between the barcode and the detection probe. However, these methods can damage the sample, and may also interfere with desired downstream reactions. Formamide stripping, for example, is known to damage proteins that are present in the sample. This can be particularly problematic if the decoding method is being used in situ, for example for transcription profiling of different cell types. The damage done by the formamide can affect epitope recognition of antibodies, and thus can disrupt any subsequent immunohistochemistry reactions which may be necessary. In addition, the use of high temperature means that the automation of the decoding method is much more difficult. This therefore makes the method more labour intensive, and thus more expensive.

In view of these issues, there is a desire for alternative methods of coding and decoding nucleotide barcode sequences, particularly cost-efficient methods which are suitable for high multiplicity scenarios, and which provide high specificity and accuracy without damaging the sample of target nucleic acid molecules which are being analysed.

The present inventors have developed a method of coding and decoding a nucleotide barcode sequence in a nucleic acid molecule to differentiate said nucleotide barcode sequence from other nucleotide barcode sequences. The method is based on a nucleotide barcode sequence design which comprises multiple sequential barcode positions, which can be interrogated separately, and sequentially. The nucleotide barcode sequence is essentially split into multiple sequential barcode positions, each of which comprises at least one barcode subunit. This sequential analysis of multiple barcode positions dramatically increases the coding capacity of the system. In a representative example, a nucleotide barcode sequence according to the present invention may comprise any one of 16 barcode subunit sequences at each barcode position. Accordingly, if n is the number of positions that are measured, the method of the present invention can encode $16^n$ different barcode sequences, relative to $4^n$ for the methods described above which use a simple continuous barcode sequence. This increase in coding capacity means that the method of the present invention can be applied to highly multiplexed situations, without requiring long barcode sequences, thus avoiding the aforementioned specificity problems. The increased multiplicity of the method also allows more nucleic acid molecules to be distinguished in parallel, in a shorter time than with the methods described above, thus reduce the time and costs involved. Even in situations where multiplicity is not a limiting factor, the significantly increased number of possible permutations of barcode sequences, means that the barcode sequences assigned to the nucleic acid sequences can be designed such that they are less similar to each other. This reduces off-target binding of detection probes, and therefore improves the specificity and accuracy of the method.

The present decoding method further involves multiple cycles of contacting the nucleotide barcode sequence with detection probes, and detecting a signal from the detection probe which has hybridised to the nucleotide barcode sequence (as discussed above). Importantly, according to the present invention the detection probes are designed such that they may act to remove, or to facilitate the removal of, a preceding detection probe by a process involving a strand displacement reaction. The strand displacement reaction may be initiated by a toehold exchange involving a subsequent detection probe which, when it hybridises to the barcode sequence at a subsequent barcode position, is able to invade the hybrid between the preceding detection probe and the nucleotide barcode sequence, such that the hybrid between the nucleotide barcode sequence and the previous detection probe is disrupted. The preceding detection probe may be displaced entirely by the subsequent detection probe, or it may be that the partial disruption of the hybrid is sufficient to subsequently lead to the dissociation of the previous detection probe from the nucleotide barcode sequence. The use of this strand displacement reaction avoids the use of damaging chemicals to remove hybridised detection probes, and provides an efficient and effective removal system. It further allows the method to be conducted at room temperature.

Accordingly, in one aspect, the present disclosure and invention provide a method of decoding a nucleotide barcode sequence in a nucleic acid molecule to differentiate said nucleotide barcode sequence from other nucleotide barcode sequences, wherein a nucleotide barcode sequence comprises multiple sequential barcode positions, each barcode position partially but not fully overlapping the adjacent barcode position in the sequence and each barcode position comprising at least one barcode subunit, wherein the barcode subunit(s) are selected from a panel of barcode subunits, such that the order of barcode positions (and therefore the order of barcode subunits) in each nucleotide barcode sequence defines a signal code sequence which comprises a signal code corresponding to each barcode position, and which is distinct from the signal code sequences of other nucleotide barcode sequences and identifies a given nucleotide barcode sequence, said method comprising:

(i) contacting the nucleic acid molecule with a first set of first detection probes for decoding the nucleotide barcode sequence at the first sequential barcode position and allowing the detection probes to hybridise to the nucleic acid molecule, wherein each detection probe in the set comprises a sequence complementary to a different barcode subunit within the panel and a reporter, such that each detection probe is capable of hybridising to and detecting a different barcode subunit at said first barcode position;

(ii) detecting a signal from the reporter of the first detection probe which has hybridized to the nucleotide barcode sequence at the first sequential barcode position;

(iii) identifying the signal code for the first barcode position from the signal detected in (ii);

(iv) contacting the nucleotide barcode sequence with a next set of subsequent detection probes for decoding the nucleotide barcode sequence at the next sequential barcode position and allowing the detection probes to hybridise to the nucleic acid molecule, wherein each detection probe comprises a sequence complementary to a different barcode subunit within the panel and a reporter, such that each detection probe is capable of hybridising to and detecting a different barcode subunit at said barcode position, and wherein the subsequent detection probe which hybridises to the barcode subunit at the next position is capable of hybridising (or more particularly, hybridises) to a sequence within the overlapping portion of the preceding barcode position, and thereby initiates a strand displacement reaction which displaces the hybridised preceding detection probe;

(v) detecting a signal from the reporter of the subsequent detection probe which has hybridized to the nucleotide barcode sequence at the next sequential barcode position;

(vi) identifying the signal code for the next barcode position from the signal detected in (v);

(vii) repeating steps (iv)-(vi) to identify signal codes for subsequent sequential barcode positions until sufficient signal codes have been identified to decode the nucleotide barcode sequence, wherein the first sequential barcode position can be any barcode position in the nucleotide barcode sequence.

A barcode subunit is an element of the barcode, i.e. an element of the barcode that is read (i.e. decoded); the barcode which is contained in (or provided by) the nucleotide barcode sequence is made up of the barcode subunits. In other words, the barcode subunits, and the order in which they are presented, together make up the barcode which is contained in the nucleotide barcode sequence. A barcode position may comprise more than one barcode subunit, and/or it may comprise a sequence which is not a barcode subunit sequence, e.g. a spacer sequence. Thus, whilst the barcode positions in the nucleotide barcode sequence are partially overlapping and follow one another sequentially in the barcode sequence, the barcode subunits need not be contiguous in sequence, although in one embodiment they may be.

A barcode position is a subsequence of the nucleotide barcode sequence. Each barcode position, although overlapping, is distinct from its immediate neighbour. A barcode position may be distinguished from an adjacent (i.e. neighbouring) barcode position by its sequence, although it is not necessary that a barcode subunit of a barcode position is distinct from a barcode subunit of an immediate neighbour. A barcode position may have barcode subunit which is distinct from an adjacent neighbour and/or a spacer sequence which is distinct from its adjacent neighbour.

A barcode position partially overlaps a neighbouring (i.e. adjacent) position. Thus a barcode position at an end of the barcode sequence overlaps one adjacent barcode position, whilst an internal barcode position (i.e. a barcode position which lies between end barcode positions) will partially overlap an adjacent barcode position on each side). Thus, an internal barcode position may be fully overlapped when both adjacent positions are considered, but it will not be fully overlapped by a single adjacent barcode position.

Where a barcode position comprises more than one subunit, an individual subunit may overlap an adjacent barcode position (or barcode subunit), as long as all the barcode subunits of a position do not overlap a single adjacent barcode position. Accordingly, each barcode position contains at least one barcode subunit that does not overlap with a single adjacent barcode position on one side (although different barcode subunits of a barcode position may overlap with the adjacent barcode positions (barcode subunits) on each side). Thus, where a barcode position comprises a single barcode subunit, the barcode subunits do not overlap. Where a barcode position consists only of barcode subunits and does not have a spacer sequence, each barcode position is distinct from another by at least one barcode subunit.

In a particular embodiment a barcode position comprises a barcode subunit flanked by spacer sequences. In other words, the barcode subunits are separated by spacer sequences. The spacer sequences of adjacent barcode positions may be overlapping. In such an embodiment the nucleotide barcode sequence can be seen as discontinuous barcode sequence, wherein the barcode subunits are not contiguous. An illustration of the arrangement of barcode positions (numbered) and barcode subunits in such a configuration is shown in FIG. 1A.

Accordingly, in one such embodiment, the present invention provides a method of decoding a nucleotide barcode sequence in a nucleic acid molecule to differentiate said nucleotide barcode sequence from other nucleotide barcode sequences, wherein a nucleotide barcode sequence comprises multiple sequential barcode positions, each barcode position comprising a first spacer sequence, a barcode subunit, and a second spacer sequence, wherein the second spacer sequence from each barcode position at least partially overlaps with the first spacer sequence of the adjacent barcode position in the sequence, and wherein each barcode subunit is selected from a panel of barcode subunits, such that the order of barcode subunits in each barcode sequence is distinct from that of other barcode sequences and identifies a given barcode sequence, said method comprising:

(i) contacting the nucleic acid molecule with a first set of first detection probes for decoding the nucleotide barcode sequence at the first sequential barcode position and allowing the detection probes to hybridise to the nucleic acid molecule, wherein each detection probe comprises a first flanking sequence complementary to at least a portion of the first spacer sequence of the first barcode position, a sequence complementary to a barcode subunit, a second flanking sequence complementary to at least a portion of the second spacer sequence of the first barcode position and a reporter, wherein each detection probe comprises a sequence complementary to a different barcode subunit within the panel, such that each detection probe is capable of hybridising to and detecting a different barcode subunit at said first barcode position;

(ii) detecting a signal from the reporter of the first detection probe which has hybridized to the nucleotide barcode sequence at the first sequential barcode position;

(iii) determining the identity of the first barcode subunit from the signal detected in (ii);

(iv) contacting the nucleotide barcode sequence with a next set of subsequent detection probes for decoding the nucleotide barcode sequence at the next sequential barcode position and allowing the detection probes to hybridise to the nucleic acid molecule, wherein each detection probe comprises a first flanking sequence complementary to at least a portion of the first spacer sequence of the subsequent barcode position, a sequence complementary to a barcode subunit, a second flanking sequence complementary to at least a portion of the second spacer sequence of the subsequent barcode position and a reporter, wherein each detection probe comprises a sequence complementary to a different barcode subunit within the panel, such that each detection probe is capable of hybridising to and detecting a different barcode subunit at said barcode position, and wherein the subsequent detection probe which hybridises to the barcode subunit at the next position hybridises to at least a portion of the second spacer sequence of the preceding barcode position, and thereby initiates a strand displacement reaction which displaces the hybridised preceding detection probe;

(v) detecting a signal from the reporter of the subsequent detection probe which has hybridized to the nucleotide barcode sequence at the next sequential barcode position;

(vi) determining the identity of the next barcode subunit from the signal detected in (v);

(vii) repeating steps (iv)-(vi) to decode subsequent sequential barcode positions until the identity of sufficient positions of the subunit barcode sequence has been determined to decode the nucleotide barcode sequence, wherein the first sequential barcode position can be any barcode position in the nucleotide barcode sequence.

In another embodiment, the barcode positions do not contain any spacer sequences, or indeed any other sequences. Thus in an embodiment the nucleotide barcode sequence comprises only (or consists of) barcode subunits. In such an embodiment, to ensure that the barcode positions are partially overlapping, it will be seen that each barcode position comprises more than one barcode subunit (i.e. at least 2 subunits). Thus, the barcode positions may overlap at a barcode subunit (or at least one subunit), but may also contain a barcode subunit (or at least one subunit) which does not overlap with an adjacent barcode position. In such an embodiment, the barcode sequence can be seen as a continuous barcode sequence where the barcode subunits are contiguous with one another. In such an embodiment a barcode position may be defined by a particular combination (e.g. pair) of subunits. An illustration of the arrangement of barcode positions (numbered) and barcode subunits in such a configuration is shown in FIG. 1B.

In such an embodiment, the invention provides a method of decoding a nucleotide barcode sequence in a nucleic acid molecule to differentiate said nucleotide barcode sequence from other nucleotide barcode sequences, wherein a nucleotide barcode sequence comprises multiple sequential barcode positions, each barcode position comprising a barcode subunit pair comprising a first barcode subunit and a second barcode subunit, wherein the second barcode subunit from each barcode position at least partially overlaps with the first barcode subunit of the adjacent barcode position in the sequence, such that the order of barcode subunit pairs in each nucleotide barcode sequence defines a signal code sequence which comprises a signal code corresponding to each barcode subunit pair, and which is distinct from the signal code sequences of other nucleotide barcode sequences and identifies a given nucleotide barcode sequence, said method comprising:

(i) contacting the nucleic acid molecule with a first set of first detection probes for decoding the nucleotide barcode sequence at the first sequential barcode position and allowing the detection probes to hybridise to the nucleic acid molecule, wherein each detection probe comprises a sequence that is complementary to a different barcode subunit pair and a reporter, such that each detection probe is capable of hybridising to and detecting a different barcode subunit pair at said first barcode position;

(ii) detecting a signal from the reporter of the first detection probe which has hybridized to the nucleotide barcode sequence at the first sequential barcode position;

(iii) identifying the signal code for the first barcode subunit pair from the signal detected in (ii);

(iv) contacting the nucleotide barcode sequence with a next set of subsequent detection probes for decoding the nucleotide barcode sequence at the next sequential barcode position and allowing the detection probes to hybridise to the nucleic acid molecule, wherein each detection probe comprises a sequence that is complementary to a different barcode subunit pair and a reporter, such that each detection probe is capable of hybridising to and detecting a different barcode subunit pair at said barcode position, and wherein the subsequent detection probe which hybridises to the barcode subunit at the next position hybridises to a sequence within the overlapping portion of the preceding barcode position, and thereby initiates a strand displacement reaction which displaces the hybridised preceding detection probe;

(v) detecting a signal from the reporter of the subsequent detection probe which has hybridized to the nucleotide barcode sequence at the next sequential barcode position;

(vi) identifying the signal code for the next barcode subunit pair from the signal detected in (v);

(vii) repeating steps (iv)-(vi) to identify signal codes for barcode subunit pairs at subsequent sequential barcode positions until sufficient signal codes have been identified to decode the nucleotide barcode sequence, wherein the first sequential barcode position can be any barcode position in the nucleotide barcode sequence.

Also disclosed herein are other aspects and embodiments, including alternative methods of decoding nucleotide barcode sequences and detecting target nucleic acid molecules. These will be described further below.

The methods presented above will now be discussed in more detail.

It will be understood that in step (vii) of the methods above steps (iv)-(vi) are repeated until sufficient signal codes have been identified to determine a signal code sequence. From the signal code sequence the nucleotide barcode sequence may be identified, or decoded. Thus, sufficient signal codes may be identified until a sufficient signal code sequence has been determined from which the nucleotide barcode sequence may be identified, and hence decoded. The methods herein thus involve a series of cycles which are performed sequentially to determine, or to create, a signal code sequence corresponding to (or representing) the nucleotide sequence barcode, and thereby to decode the nucleotide barcode sequence. Steps (i)-(iii) can be seen as the first cycle of the method. Each repetition of steps (iv)-(vi) can thus be seen as a further cycle of the method. It is not necessary that all barcode positions are read or decoded, to compile (or assemble) a complete signal code sequence, but in one embodiment they may be. In another embodiment, for example where there is a low number of barcodes present, it may not be necessary to decode a complete barcode sequence to be able to distinguish it and an incomplete number of cycles may suffice. Some barcodes in a sample may require a greater number of cycles to be distinguished over another.

In some embodiments, the step of identifying the signal code may directly identify the barcode subunit(s) at that position (i.e. the signal code may correspond directly to a particular barcode subunit(s) which may be present at that position). In other embodiments, a given signal code at one position may not act to identify a particular subunit at that position, and the identity of a series (i.e. a sequence) of signal codes (i.e. a signal code sequence, or a sufficient part thereof) may be needed to identify a given nucleotide barcode sequence. Thus, the method essentially "converts" a nucleotide barcode sequence into a signal code sequence, which identifies that particular nucleotide barcode sequence. A nucleotide barcode sequence may be assigned a signal code sequence corresponding to the barcode subunits present in that barcode. For example a nucleotide barcode sequence BC1-BC2-BC3-BC4-BC5-BC6 (wherein the BCx represents one or more barcode subunits which are present at a position of x=1-6 in the barcode sequence) may be assigned a colour code sequence B-R-Y-G-B-R (wherein B=blue, R=red, G=green and Y=yellow). It will be seen that the same colour (signal code) may need to be used for different subunits or different positions, but barcodes can be designed which give rise to unique signal code sequences which distinguish them from each other. To decode which nucleotide barcode sequence is present, detection probes may be used to read the barcode sequence at each position, and obtain a colour code sequence from which the nucleotide barcode sequence may be identified, or determined.

Since the first sequential barcode position can be any barcode position, it can be seen that the barcode sequence can be read (decoded) in either order. Thus, the first sequential barcode position can be the barcode position at, or closest to, the 5' or 3' end of the nucleic acid molecule. It can be the first barcode position or the last barcode position from the 5' end of the barcode sequence. Further, the first sequential barcode position could be an "internal" barcode position of the barcode sequence. The method may be performed starting from more than one barcode position, simultaneously or sequentially. In other words, the barcode may be read starting from different barcode positions. In such an embodiment, a barcode position may be read more than once. The method may be used to detect and distinguish a nucleotide barcode sequence from other barcode sequences which are present in a sample under test or investigation. Accordingly, the method may be performed on a sample comprising multiple different nucleotide barcode sequences, or more particularly a sample comprising multiple nucleic acid molecules containing different nucleotide barcode sequences. As used herein "multiple" or "multiplicity" means at least 2.

Since the sequential barcode positions each partially but not fully overlap the adjacent barcode position in the sequence, a barcode position thus comprises at least one overlapping region, which overlaps with an adjacent barcode position in the sequence and a non-overlapping region, which does not overlap with that adjacent barcode position in the sequence. Thus, relative to a (i.e. to one, or to a single) neighbouring (adjacent) barcode position, a given barcode position comprises a region which is identical or homologous in sequence (i.e. a common region). The barcode position comprises a further region which does not overlap and which may be different to the non-overlapping region of the adjacent position. The common region is able to hybridise to a common complementary region within both sets of detection probes for decoding each of the two barcode positions. In certain embodiments the non-overlapping region is not able to hybridise to a subsequent detection probe for decoding the next barcode position. However, in other embodiments the non-overlapping region is able to hybridise to a subsequent detection probe for decoding the next barcode position. Accordingly, in one embodiment, the different region cannot hybridise to a detection probe for the adjacent barcode position, but this is not a requirement. The different region may comprise a barcode subunit. The common region may comprise a barcode subunit (and hence that barcode subunit is shared between the two adjacent positions) or a spacer (which is shared).

In one embodiment, the non-overlapping (i.e. different) region of a given barcode position may be capable of hybridising to a subsequent detection probe for decoding the next barcode position. This embodiment is illustrated in FIG. 5, which shows a barcode sequence made up of 2 barcode positions, each comprising a barcode subunit (C or T) surrounded by spacer sequences (xxxxx or zzzzz). The first detection probe which is complementary to the first barcode position hybridises to the barcode sequence, and a signal is detected. The barcode sequence is then contacted with a second detection probe which comprises a sequence complementary to both the second barcode position and the first barcode position. Accordingly, the region of the second detection probe that is complementary to the second barcode position can act as a toehold, allowing the second detection probe to hybridise to the barcode sequence and remove the preceding detection probe via strand displacement. The extended sequence of the second detection probe ensures that the preceding detection probe is displaced entirely. It can therefore be seen that a detection probe for decoding a given barcode position may also comprise a sequence which is complementary to the preceding barcode position. Detection probes may comprise sequences complementary to multiple adjacent barcode positions. In such a design, the region of the subsequent detection probe that is complementary to the barcode subunit of the preceding detection probe may be degenerate at the site complementary to the preceding barcode subunit (as indicated by N in the second detection probe in FIG. 5. Thus, the subsequent detection probe may be synthesised such that all 4 bases are incorporated at this position (in other words, the subsequent detection probe may be a mixture which comprises probes with different nucleotides at the degenerate position). Such an embodiment is less preferred, due to the need to make longer, and more probes.

A barcode position thus provides a recognition site (i.e. a binding site, or hybridisation site) for a detection probe, and conversely a detection probe can be seen as comprising a corresponding or cognate (i.e. complementary) recognition site for that barcode position. The complementary recognition (binding) sites in adjacent barcode positions for their respective detection probes overlap partially. Accordingly, a subsequent detection probe for the next barcode position in the barcode sequence is able to hybridise to at least a portion of the binding site for the preceding detection probe, i.e. to a sequence in the overlapping portion of the barcode position to which the preceding detection probe has hybridised. This allows a toehold exchange reaction to take place, wherein the subsequent detection probe hybridises to the barcode sequence and is able to invade the hybrid between the preceding detection probe and the barcode sequence. By way of further explanation, the recognition site (complementary region) in a detection probe for a non-overlapping region of a barcode position (i.e. the region which is non-overlapping with an adjacent, e.g. the preceding, barcode position) can be seen to provide the detection probe with a toehold, by which it can bind to the nucleotide barcode sequence (or more particularly to the barcode position). This applies particularly in the case of a subsequent detection probe, which may bind to the next barcode position, at the non-overlapping region, whilst the preceding barcode position is occupied by a preceding detection probe. Conversely viewed, the non-overlapping (e.g. different) region of the subsequent barcode position provides a toehold (or more precisely a "toehold-complement") for the detection probe to hybridise. The methods may thus be seen to involve a toehold-mediated strand displacement reaction. As noted above, it is not necessary for the preceding detection probe to be entirely displaced by the subsequent detection probe. A toehold-mediated strand displacement reaction which results in displacement of a portion of the preceding detection probe may be sufficient to cause the preceding detection probe to dissociate from the barcode sequence.

Thus, the subsequent detection probe may undergo a toehold exchange reaction, which results in (or which may cause or initiate) displacement of the preceding probe. Accordingly, in other words, in step (iv) of the methods herein, the subsequent detection probe which hybridises to the barcode subunit at the next position is capable of hybridising to a sequence within the overlapping portion of the preceding barcode position, and mediates a toehold exchange reaction which initiates displacement of the hybridised preceding detection probe.

As indicated above, the method of the present invention may be viewed as a method of sequencing by hybridisation, wherein the nucleotide sequence barcode is decoded by a SBH reaction. The nucleic acid molecule, and more particularly the nucleotide sequence barcode may thus be viewed as a sequencing substrate. The detection probes may be viewed as sequencing probes in a SBH method.

The number of barcode positions in the nucleotide barcode sequence can be varied depending on the multiplicity that is required for a given application. For example, the nucleotide barcode sequence can comprise at least 2, 3, 4, 5, 6, 7, 8, 9, 10, or 20 or more barcode positions.

A barcode subunit may range in size from a single base to a longer sequence of bases, again depending on the precise nature of the method (e.g. whether spacers are used) and the complexity or multiplicity required. The size of a barcode subunit may therefore range from 1-20 bases for example, e.g. 1-15, 1-12, 1-10, 1-9, 1-8, 1-7, 1-6, 1-5, 1-4 or 1-3 bases. It will be understood that a barcode position needs to be of a size which permits an overlap with an adjacent barcode position, and which allows a detection probe to bind specifically to that barcode position. Where a barcode position comprises spacer sequences flanking the barcode subunit, the size of a barcode subunit may therefore be at the lower end of the range, e.g. 1-6, or fewer bases. Where a barcode position consists only of barcode subunits, a barcode subunit will typically be longer, e.g. from any one of 6, from 7, 8, 9 or 10, to any one of 12, 15, 18 or 20.

In an embodiment, a barcode position may have a size of 8-60 bases, e.g. from 8, 9, 10, 12, 15, or 18 bases to 16, 18, 20, 22, 25, 26, 28, 30, 40 or 50 bases.

Each barcode position within the nucleotide barcode sequence comprises at least one barcode subunit. The barcode subunit(s) at each barcode position may be selected from a panel of barcode subunits. A panel is simply a list, group or collection of barcode subunits which are used in the barcodes sequences. The barcode subunits which may be contained in, or which may form, the panel is not limited. The term "panel" does not imply any restriction on the number or type of barcode subunits. This, the panel need not comprise a limited number of barcode subunits which are reused (or repeated) in different barcode positions, or in different barcode sequences, although this may of course be the case (e.g. where a barcode subunit is a single base, or a small number of bases, e.g. 1-3). In other embodiments each barcode subunit in the panel may be unique. The size of the panel of barcode subunits can be varied depending on the multiplicity that is required. For instance, the panel of barcode subunits may contain at least 2, 3, 4, 5, 6, 7, 8, 9, 10, 15, 20, 30, 50 or 100 or more barcode subunits.

Each barcode subunit may be used multiple times in a single nucleotide barcode sequence, that is to say, a given barcode subunit may appear in multiple barcode positions in the same nucleotide barcode sequence. In addition, each barcode subunit may be used in multiple different nucleotide barcode sequences. Alternatively, it may be that each barcode subunit in a given nucleotide barcode sequence is unique, or further that each barcode subunit in each nucleotide barcode sequence is unique.

The barcode subunits in the nucleotide barcode sequence define a signal code sequence. The signal code sequence comprises a signal code corresponding to each barcode position within the nucleotide barcode sequence, and is distinct from the signal code sequences of other nucleotide barcode sequences. The signal code sequence is thus defined by, and can be used to identify, the nucleotide barcode sequence.

As noted above, a nucleotide barcode sequence may be designed with a sequence of barcode positions which are designed to yield a particular signal code sequence, or in other words to correspond to a particular signal code sequence, which can be decoded using detection probes designed to bind to the sequential barcode positions. The nucleotide barcode sequence may thus correspond to, or represent, a predetermined signal code sequence.

Each barcode position in every nucleotide barcode sequence is assigned a signal code. The signal code may be, but need not be, unique to a particular barcode position (or a particular barcode subunit). An individual signal code is in turn indicated by a given reporter. The reporter gives rise to the signal code. Accordingly, each nucleotide barcode sequence is assigned a corresponding signal code sequence, made up of the signal codes observed from the reporters on the detection probes that hybridise to each of the constituent barcode positions.

The available signal codes may be limited by the available reporters, which are available to give rise to signals which may be distinguished from one another. Accordingly, a given signal code may be assigned to multiple barcode positions in the same nucleotide barcode sequence, and/or to multiple barcode positions in different nucleotide barcode sequences. Further the same signal code may be assigned to different subunits, or subunit combinations. Each reporter may therefore be observed at multiple barcode positions in a single nucleotide barcode sequence, and/or at a given barcode position in multiple different nucleotide barcode sequences. It may therefore not be possible to determine the identity of a barcode subunit within a given barcode position solely from the signal detected from the detection probe which hybridises to that barcode position, as explained above.

Alternatively, it may be that each signal code in a given nucleotide barcode sequence is unique for that nucleotide barcode sequence.

The method of decoding a nucleotide barcode sequence in a nucleic acid molecule comprises a first step of contacting the nucleic acid molecule with a first set of first detection probes for decoding the first sequential barcode position. A detection probe is thus an oligonucleotide probe comprising a sequence, or domain, capable of hybridising to the barcode position. Each detection probe comprises a sequence which is complementary to a different barcode subunit, or combination of barcode subunits, from within the panel of barcode subunits (or in other words, each detection probe in the set comprises a sequence complementary to the different barcode subunit(s) within the panel which may be present at the first position). The complementary sequence may be viewed as a binding site, or binding domain (or recognition site) of the detection probe. Thus, a set of detection probes is designed to detect which of the possible subunit(s), which may be present at the interrogated position of a set of barcodes, is present at that position in a given barcode, or which possible subunits may be present, or to assign a particular signal code to the subunits(s) which are present at that position, from which the barcode may be decoded. A detection probe may accordingly be alternatively referred to as an interrogation probe, or a decoding probe.

In addition to the complementary sequence (i.e. binding domain), each detection probe comprises a reporter, which indicates a particular signal code, as outlined above. Accordingly, each detection probe is capable of hybridising to and detecting different barcode subunit(s) at the first sequential barcode position. Each detection probe may comprise a different reporter. Alternatively, some detection probes may comprise the same reporter.

As used herein, the term "reporter" refers to the region of the detection probe which is responsible for providing a signal which can be detected. The signal is typically provided by a detectable moiety. Accordingly a signal may include the signal detectable from the detectable moiety, and different detectable moieties may provide different signals which may be distinguished, e.g. by colour. It will be understood that absence of signal may also be detected, and the signal which is detected may be absence of signal. Accordingly in a detection probe set the reporter of one of probes may be the absence of reporter, or the reporter may be lacking a detectable moiety. Alternatively expressed, in the methods herein, each detection probe within a detection probe set may comprise a reporter or one of the detection probes may lack a reporter and the others may each comprise a reporter. In line with this, step (ii) may include detecting an absence of signal, or may alternatively be defined as detecting a signal from the reporter, or the absence of a signal.

The detectable moiety may be directly or indirectly linked to the reporter (or to the binding domain of the detection probe). The reporter may thus be directly or indirectly signal-giving. Different detection probe designs showing directly or indirectly linked reporters are shown in FIG. 3. In some embodiments, the detectable moiety is incorporated into the reporter region of the detection probe or conjugated to the binding domain. For example the reporter may be a label which is linked directly or via a linker to the binding domain, and this may include the absence of label, which is detected by absence of signal. Accordingly, in a set of detection probes, one of the probes may lack a label and the other probes in the set may be provided with labels. Whilst in one embodiment, the labels of the probes in a probe set may be distinguishable from one another, as explained above, in other embodiments different detection probes in the probe set may have the same label (as the signal code sequence which is detected from sequential detection probes may be used to decode the nucleotide barcode sequence). FIG. 3 depicts detection probe sets for decoding a discontinuous barcode sequence (as shown in FIG. 3A). The probe set shown in FIG. 3B shows detection probes directly provided with colorimetric labels, which serve as reporters.

Alternatively, the reporter may provide a signal indirectly, i.e. it may require the addition of further components to generate a signal. For instance, the reporter of the detection probe may be a domain capable of binding a species that comprises a detectable moiety. In a preferred embodiment, the reporter comprises a binding site for a reporter probe which comprises a detectable moiety. More particularly the reporter may comprise a binding site in the form of a nucleotide sequence comprising a region or domain to which a complementary reporter probe may hybridise. The nucleotide sequence will not be complementary, and will not be able to hybridise to the nucleotide barcode sequence (or more generally to the nucleic acid molecule in which the barcode sequence is contained).

Thus, the reporter may be in the form of an overhang region at one end of the detection probe, which is not complementary to the nucleotide barcode sequence, but comprises a binding site which is complementary to the sequence of a reporter probe. In this case, the reporter probe comprises a cognate sequence which is complementary to that of the binding site in the reporter, and a detectable moiety. In this format the detection probe may be seen to take the form (i.e. structure) of an L-probe. In some embodiments, the detection probe may comprise a reporter overhang region at both ends, such that two reporter probes can bind to each detection probe, in order to increase the strength of the signal provided. In this format the detection probe may be seen to take the form (i.e. structure) of a U-probe. L-probes are depicted for example in FIG. 2. Indirect detection probes with L- and U-probe configurations are further shown in FIGS. 3C and 3D, respectively.

The step (i) of contacting the nucleic acid molecule with a first set of first detection probes may therefore further comprise contacting the nucleic acid molecule with a set of reporter probes, cognate for the detection probes. By "cognate" is meant a reporter probe which corresponds to and is designed to bind to a particular detection probe. Each reporter probe in the set comprises a sequence which is complementary to that of the reporter probe binding site in a different detection probe. In one embodiment each reporter probe may comprise a detectable moiety. The detectable moiety may be different. In another embodiment, where absence of signal is to be detected, all but one of the reporter probes in the set comprises a detectable moiety and one of the reporter probes lacks may lack a detectable moiety. In another embodiment the reporter probe set may lack a reporter probe corresponding to one of the detection probes. Thus, a detection probe which "reports" by absence of signal may lack a binding site for a reporter probe. Embodiments which include detection of absence of signal are less preferred. The first set of first detection probes and the set of reporter probes may be added simultaneously or sequentially. In one embodiment, the first set of first detection probes may be contacted with the set of reporter probes before the detection probes are contacted with the nucleic acid molecule comprising the nucleotide barcode sequence (i.e. the reporter probes may be pre-hybridised to the detection probes).

The use of indirect "labelling" via reporter probes means that the detectable moieties can be re-used to provide a signal at multiple barcode positions. Although the detection probes will differ from each other in the sequences that hybridise to the nucleotide barcode sequence, the sequences of the reporter probe binding sites, i.e. the reporter overhang regions (and of the complementary reporter probes) may be conserved across different barcode positions. This means that although different detection probes are required for each barcode position, the direct reporter probes can be re-used for decoding multiple barcode positions. This significantly reduces the cost of the method.

Detectable moieties that may be used according to the methods herein, either in detection probes, or in reporter probes, include any moiety capable of providing a signal that can be detected, for example fluorescent molecules (e.g. fluorescent proteins or organic fluorophores), colorimetric moieties (e.g. coloured molecules or nanoparticles), particles, for example gold or silver particles, quantum dots, radioisotopes, chemiluminescent molecules, and the like. The detectable moiety may be viewed as a label, and any detectable label may be used. In particular, any spectrophotometrically or optically-detectable moiety may be used.

The detectable moiety may be distinguishable by colour, but any other parameter may be used e.g. size.

In a preferred embodiment, the reporter or the reporter probe comprises a fluorescent molecule, e.g. a fluorophore. Fluorescent molecules that may be used to label nucleotides are well known in the art. Exemplary fluorophores include ATT0425, Cy®3 (dye), Cy®5 (dye), Cy®7 (dye), and AF488 (Alexa Fluor® 488) (dye), though any suitable fluorophores may be used. Fluorophores have been identified with excitation and emission spectra ranging from UV to near IR wavelengths. Thus, the fluorophore may have an excitation and/or emission wavelength in the UV, visible or IR spectral range. The fluorophore may be a peptide, small organic compound, synthetic oligomer or synthetic polymer. In some embodiments, the fluorophore is a small organic compound.

As noted above, alternatively, the reporter or the reporter probe may comprise no detectable moiety. In this case, the signal that is reported is the absence of any detectable moiety, which is distinguishable from any number of distinct positively detectable moieties.

Where the reporter or reporter probe comprises a fluorophore, the signal code for each barcode position may be the colour of the fluorophore of the reporter/reporter probe of the detection probe that hybridises to that barcode position. Accordingly, each nucleotide barcode sequence has a corresponding signal code sequence which may comprise a specific sequence of colours, which is distinct from the sequence of colours that makes up the signal code sequence of every other nucleotide barcode sequence.

When the nucleic acid molecule comprising the nucleotide barcode sequence is contacted with the first set of detection probes, the detection probe with a sequence complementary to the barcode subunit(s) at the first sequential barcode position can hybridise to the nucleic acid molecule at said first sequential barcode position. A signal can then be detected from the reporter of the first detection probe which has hybridised to the nucleotide barcode sequence at the first sequential barcode position. It will be understood that the step of detecting the signal from the reporter includes detecting the signal from a reporter probe, if that is used. The signal may be detected by any suitable means known in the art for detecting the relevant detectable moiety. In some embodiments, the signal may be detected by imaging the sample of target nucleic acid molecules. In some embodiments, steps (ii) and (v) of detecting a signal from the reporter of a hybridised detection probe may comprise imaging the sample multiple times. For example, if the detectable moiety is a fluorophore, the signal may be detected using fluorescence microscopy to determine the identity of the fluorophore, or the absence of the fluorophore. It will be evident that other appropriate imaging techniques known in the art to identify signals from suitable detectable moieties may be used in the present methods to detect a signal from the reporter of a hybridised detection probe.

The step (ii) and/or step (v) of detecting a signal from the reporter of a detection probe may further comprise a step of removing the unhybridised detection probes, prior to detecting the signal. The removal of the unhybridised probes may improve the strength of the signal that is detected, or the signal to noise ratio. This removal step may be carried out be washing the nucleic acid molecule with an appropriate wash buffer. The step of washing the solid substrate may be repeated multiple times, e.g. 2, 3, 4, 5 or more times, as is necessary to obtain a clear signal from the reporter.

However, such a removal step is optional, and may not be necessary, or may not always be desirable or appropriate. For example, rather than detecting the signal as an endpoint measurement, the signal may be measured over time, e.g. as a series of measurements at spaced time points. Such a time-resolved measurement is described in WO 2017/222453, incorporated herein by reference. In such a procedure, images are taken while all the detection probes are present (excess or unhybridised detection probes are not removed).

The step of detecting a signal from the reporter of the first detection probe allows the signal code for the first sequential barcode position of the nucleotide barcode sequence to be identified. The steps of hybridising a detection probe to a barcode position, detecting a signal from said detection probe, and therefore identifying the signal code for said barcode position are then effectively repeated in order to identify signal codes for subsequent barcode positions. It is desirable to remove the preceding hybridised detection probe from the nucleotide barcode sequence before attempting to detect a signal from the subsequent detection probe. According to the present methods, this is achieved at least in part by a strand displacement reaction, which is initiated, or mediated, by the subsequent detection probe, which acts to disrupt the hybridisation of the previous detection probe (i.e. to disrupt the hybrid between the preceding detection probe and the nucleotide barcode sequence After the first cycle, the methods herein comprise a step of contacting the nucleotide barcode sequence with a next set of subsequent detection probes for decoding the next sequential barcode position. Again, each subsequent detection probe in the set comprises a sequence which is complementary to a different barcode subunit within the panel of barcode subunits (or more particularly to different barcode subunit(s) within the panel which may be present at the next position). Accordingly, each subsequent detection probe is capable of hybridising to and detecting a different barcode subunit, or a different combination of barcode subunits, at the next sequential barcode position. The subsequent detection probe which hybridises to the nucleotide barcode sequence at the next sequential barcode position is also capable of hybridising to a sequence within the overlapping portion of the preceding barcode position. By hybridising to a target barcode subunit at the next sequential position, the subsequent detection probe gains a toehold, and is able to invade the hybrid between the hybridised preceding detection probe and the nucleotide barcode sequence. This invasion disrupts the hybrid between the preceding detection probe and the nucleotide barcode sequence within the overlapping portion of the previous barcode position, and thus may lead to the displacement of the hybridised preceding probe.

Once the strand invasion by the subsequent detection probe has disrupted the hybrid between the preceding detection probe and the nucleotide barcode sequence within the overlapping portion of the previous barcode position, the preceding detection probe is only hybridised to the nucleotide barcode sequence at the non-overlapping region of the previous barcode position. This partial disruption of the hybrid may be sufficient to cause the preceding detection probe to dissociate from the nucleotide barcode sequence. In many cases, the remaining interactions between the preceding detection probe and the nucleotide barcode sequence are insufficient to maintain a stable hybrid. Once the subsequent detection probe has hybridised to the overlapping portion of the previous barcode position, the melting temperature of the hybrid between the preceding detection probe and the nucleotide barcode sequence is likely to be relatively low, and thus the preceding detection probe will dissociate relatively quickly.

However, in some cases, the preceding detection probe may remain hybridised to the nucleotide barcode sequence via interactions in the non-overlapping region of the previous barcode position. This may occur with longer barcode positions, where a greater number of interactions can subsist between the partially displaced detection probe and the nucleotide barcode sequence. In this case, it may be helpful or desirable to use an additional displacer probe in order to remove the preceding detection probe.

A displacer probe may be designed to have a sequence complementary to that of the detection probes, such that they can hybridise to the detection probes in order to mediate the necessary displacement reaction. A detection probe may therefore be designed such that two separate displacement reactions can be initiated in order to remove it from the nucleotide barcode sequence, one from either end of the hybrid between the detection probe and the nucleotide barcode sequence. Firstly, the subsequent detection probe can invade the hybrid by hybridising to the nucleotide barcode sequence at the overlapping region between the preceding barcode position and the subsequent barcode position to be read. In addition, an additional displacer probe can invade the hybrid at the opposite end by hybridising to the hybridised detection probe. In order to provide a toehold for a displacer probe to bind, a detection probe may comprise an overhang region (a so-called "displacer toehold overhang"), which does not hybridise to the nucleotide barcode sequence. If an overhang is present in order to provide a binding site for a reporter probe, such a displacer toehold overhang for the displacer probe would be separate to the "reporter overhang". In other words, the detection probe may be designed to have a U-probe configuration when hybridised to the nucleotide barcode sequence. Thus, in an embodiment, the detection probe may hybridise to the barcode position with 2 single-stranded overhangs, one for a reporter probe and the other for a displacer probe. Detection probes according to this design are shown in FIG. 3D. Accordingly, in some embodiments of the present invention, step (iv) further comprises contacting the nucleotide barcode sequence with a set of displacer probes for displacing the preceding set of detection probes. The displacer probes are designed to be cognate for the set of detection probes they are to displace. In the displacer probe set, each displacer probe may comprises a first domain comprising (or being) a displacer toehold binding region which is complementary to a toehold sequence in a displacer toehold overhang of a preceding detection probe, and a second domain comprising a sequence complementary to a sequence in the barcode position binding site (recognition site) of the detection probe it is designed to displace. Thus, once bound to the displacer toehold, the displacer probe may invade the hybrid between the detection probe and the nucleotide barcode sequence. A set of displacer probes will thus each contain a different second domain complementary to at least a part of the barcode position binding site of a different detection probe. In this respect, it may be desirable for the displacer probe to be complementary to a sequence in the barcode position binding site which is not complementary to a barcode subunit. Thus, such an embodiment using a displacer probe may particularly be envisaged for the method discussed above, wherein the nucleotide barcode position is discontinuous, and a barcode position comprises a barcode subunit flanked by spacers. More particularly, the second domain of a displacer probe may be complementary to (and may hybridise to) a portion of the barcode position binding site of the detection probe which hybridises to the first spacer of the barcode position. The first domain (displacer toehold binding region) may be the same or different in different displacer probes in the set. By corollary, the displacer toehold overhang region of a set of detection probes (or indeed all the sets of detection probes) may be common to all detection probes, or each detection probe may have a unique displacer toehold overhang region.

Once a signal has been detected from the reporter of the detection probe which has hybridised to the nucleotide barcode sequence, the nucleotide barcode sequence may be contacted with a set of displacer probes, which each comprise a sequence (second domain) complementary to that of a different detection probe. This may be done prior to, during or after contacting with the next set of subsequent detection probes. Preferably the nucleotide barcode sequence is contacted with the set of displacer probes prior to or during contacting with the next set of subsequent detection probes. The displacer probe with a sequence complementary to that of the detection probe which has hybridised to the nucleotide barcode sequence can invade the hybrid between the nucleotide barcode sequence and the detection probe and hybridise to the detection probe, displacing the nucleotide barcode sequence and thus assisting in the removal of the detection probe.

The methods may further comprise a step of washing the nucleotide barcode sequence with an appropriate wash buffer after a signal has been detected from a set of detection probes. This step of washing may be carried out in addition to the previously described step of washing the nucleotide barcode sequence once the detection probes have been added in order to remove any unhybridised detection probes or previous detection probes which have been partially displaced but have not fully disassociated from the nucleotide barcode sequence, prior to detecting a signal from the subsequent detection probe that has hybridised to the nucleotide barcode sequence. Washing the nucleotide barcode sequence in this manner means that the concentration of preceding detection probe is maintained at a low level, and thus minimises the possibility of the preceding detection probe re-hybridising to the nucleotide barcode sequence, or being replaced by another copy of the same detection probe, once it has dissociated.

The present method can be adapted to accommodate varying numbers of nucleotide barcode sequences by altering the number of barcode positions in each nucleotide barcode sequence, and/or the number of barcode subunits in the panel. If more barcode positions and/or barcode subunits are used in each nucleotide barcode sequence, then the total number of unique nucleotide barcode sequences possible, and thus the number of nucleic acid molecules that can be distinguished, will be higher. The method can therefore be adapted to systems with varying levels of multiplicity, by changing the number of barcode positions or the number of barcode subunits. In situations where the number of nucleic acid molecules to be distinguished is close to, or equal to the number of possible nucleotide barcode sequences that have been generated, it may be necessary to identify the signal code for each barcode position of each nucleotide barcode sequence in order to decode the nucleotide barcode sequences. Conversely, as noted above, in circumstances where a large number of barcode positions and/or barcode subunits are used, but relatively few nucleotide barcode sequences are to be distinguished, it may not be necessary to identify the signal code for each barcode position in order to identify a given nucleotide barcode sequence. Accordingly, the steps of the present method may be repeated until sufficient signal codes have been identified to decode the nucleotide barcode sequence. A schematic reaction scheme showing the process of decoding a barcode sequence using cycles of hybridisation, imaging and displacement of detection probes is shown in FIG. 4.

As further noted above, the first sequential barcode position, i.e. the barcode position that is read first, can be any barcode position in the nucleotide barcode sequence. The nucleotide barcode sequence can thus be read in either direction, i.e. from 5' to 3' or from 3' to 5'. The nucleotide barcode sequence may also be read in both directions, either sequentially or simultaneously. The nucleotide barcode sequence can be read beginning at any position. It is not necessary for the first sequential barcode position to be one of the two terminal barcode positions, i.e. either the barcode position that is closest to the 5' end of the nucleotide barcode sequence, or the barcode position that is closest to the 3' end of the nucleotide barcode sequence. The non-terminal barcode positions may be referred to as internal barcode positions. If the first barcode position is not one of the two terminal barcode positions, then it may be necessary to repeat the method of the present invention from more than one starting point or in more than one direction, in order to identify the signal code for each barcode position in the nucleotide barcode sequence.

As indicated above, in one embodiment the method may be for decoding a nucleotide barcode sequence which is discontinuous, and in particular wherein each barcode position comprising a first spacer sequence, a barcode subunit, and a second spacer sequence (i.e. wherein each barcode position comprises a barcode subunit flanked by first and second spacers respectively). Such a barcode sequence and the design of detection probes for decoding it is shown in FIG. 3. Further, FIG. 4 shows the steps in the operation of such a method. The second spacer sequence of each barcode position at least partially overlaps with the first spacer sequence of the adjacent barcode position in the sequence. In a preferred embodiment, the second spacer sequence of each barcode position fully overlaps with the first spacer sequence of the adjacent barcode position, such that the second spacer sequence of one barcode position forms the first spacer sequence of the adjacent barcode position. Accordingly, the terminal barcode positions in this embodiment have one overlapping region comprising a spacer sequence, and a non-overlapping region comprising a barcode subunit and a spacer sequence. The non-terminal (or internal) barcode positions comprise two overlapping regions, each comprising a spacer sequence, and a non-overlapping region comprising a barcode subunit.

In this embodiment, the spacer sequences between each barcode subunit within a given nucleotide barcode sequence are different. In other words, within a nucleotide barcode sequence, the spacer sequences are specific, or particular, for a given barcode position. However, the spacer sequences are common for all nucleotide barcode sequences (i.e. the spacers are common between different nucleotide sequences). In other words, all nucleotide barcode sequences have the same spacer sequences in each of the corresponding barcode positions. Thus, in the nucleotide barcode sequences in such an embodiment, each barcode position has a combination of first and second spacer sequences which is unique to that position, and different to that of other positions. A barcode position may be defined and distinguished by its spacer sequences. The spacer sequences at each position are the same in different nucleotide barcode sequences. Accordingly, different nucleotide barcode sequences vary only in the barcode subunit sequences. This means that the flanking sequences in the detection probes complementary to the spacer sequences in the barcode positions are conserved. The detection probes in a set have particular flanking regions that are common to each probe in the set (for a particular barcode position). The flanking regions of probes in a set are different to those of other sets. The hybridisation of the flanking sequences of the detection probes to the corresponding spacer sequences in the nucleotide barcode sequence guides the order in which the nucleotide barcode sequence is read, and ensures that each detection probe hybridises at the correct barcode position.

In such an embodiment, the binding site (complementary region) in the detection probe (particularly in a subsequent detection probe) for the second spacer sequence can be seen to provide a toehold for a subsequent detection probe to bind, whilst the preceding barcode position is occupied by a preceding detection probe.

The length of the spacer sequences can vary. In some embodiments the spacer sequences may be from about 2 to about 100 nucleotides in length, including from about 2 to about 50 nucleotides in length, e.g. from about 2 to about 40 nucleotides in length, such as from about 2 to about 30 nucleotides in length, from about 2 to about 20 nucleotides in length, from about 4 to about 15 nucleotides in length, from about 4 to about 10 nucleotides in length, from about 4 to about 8 nucleotides in length, and so on. In some embodiments the spacer sequences may be 6 nucleotides in length. The spacer sequences at different positions within a given nucleotide barcode sequence may all be the same length, or they may be different lengths at each position.

The barcode subunit at each barcode position is selected from a panel of barcode subunits. As discussed above, the size of the panel of barcode subunits can be varied depending on the multiplicity that is required. For instance, the panel of barcode subunits may contain at least 2, 3, 4, 5, 6, 7, 8, 9, 10, 20, 30, 40 or 50 or more barcode subunits.

The length of the barcode subunit sequences can also vary. In some embodiments, the barcode subunit sequences may be 1, 2, 3, 4, 5, 6, 7, 8, 9, 10 or more nucleotide(s) in length. Where the barcode subunit sequences are 2 nucleotides in length, the first and second nucleotides in each barcode subunit sequence may be the same or different. The barcode subunit sequences may be made up solely of the four conventional nucleotides i.e. nucleotides comprising one of the four bases found in DNA; adenine, guanine, cytosine and thymine (A, T, C and G). Alternatively, the barcode subunit sequences may comprise non-conventional nucleotides such as uracil, or non-naturally occurring nucleotides, as are known in the art.

The length of the barcode subunits determines the number of different possible different subunits that can be generated and therefore provides an upper limit on the size of the panel. In a preferred embodiment, the barcode subunit sequences are 3 nucleotides in length, and thus there are 64 different possible barcode subunit sequences.

The barcode subunit sequences that make up the panel are all different from each other, and therefore each barcode subunit must comprise at least 1 mismatch relative to every other barcode subunit. In some embodiments, each barcode subunit may comprise 2, 3, 4, 5 or more mismatches relative to every other barcode subunit. In a more preferred embodiment, barcode subunits are three nucleotides in length, and each barcode subunit has at least 2 bases which are mismatched relative to every other sequence. Alternatively put, no barcode subunit in the panel is distinguishable from another barcode subunit by only a single base substitution.

In this case, where the barcode subunit sequences are 3 nucleotides in length and each barcode subunit comprises at least 2 mismatches relative to every other barcode subunit, there are 16 different possible barcode sequences. A list of all possible triplet combinations (4 possible sets) is provided in the table below.

TABLE 1

All possible sets of triplets with a minimum of 2 bases mismatch. Per set (column) there are 16 such triplets with 2 mismatches against the other triplets.

| Set 1 | Set 2 | Set 3 | Set 4 |
|---|---|---|---|
| 'AAA' | 'AAC' | 'AAG' | 'AAT' |
| 'ACC' | 'ACA' | 'ACT' | 'ACG' |
| 'AGG' | 'AGT' | 'AGA' | 'AGC' |
| 'ATT' | 'ATG' | 'ATC' | 'ATA' |
| 'CAC' | 'CAA' | 'CAT' | 'CAG' |
| 'CCA' | 'CCC' | 'CCG' | 'CCT' |
| 'CGT' | 'CGG' | 'CGC' | 'CGA' |
| 'CTG' | 'CTT' | 'CTA' | 'CTC' |
| 'GAG' | 'GAT' | 'GAA' | 'GAC' |
| 'GCT' | 'GCG' | 'GCC' | 'GCA' |
| 'GGA' | 'GGC' | 'GGG' | 'GGT' |
| 'GTC' | 'GTA' | 'GTT' | 'GTG' |
| 'TAT' | 'TAG' | 'TAC' | 'TAA' |
| 'TCG' | 'TCT' | 'TCA' | 'TCC' |
| 'TGC' | 'TGA' | 'TGT' | 'TGG' |
| 'TTA' | 'TTC' | 'TTG' | 'TTT' |

This design of barcode subunit sequences with at least 2 mismatches makes it easier to discriminate between the different barcode sequences and therefore reduces off-site binding of the detection probes. In turn, this results in a method with reduced overall error rate and improved specificity, relative to methods where the different barcode subunit sequences differ by only a single nucleotide. However, barcode subunits of a single base are not precluded.

As noted earlier, each barcode subunit may be used multiple times in a single nucleotide barcode sequence, that is to say, a given barcode subunit may appear in multiple barcode positions in the same nucleotide barcode sequence. In addition, each barcode subunit may be used in multiple different nucleotide barcode sequences.

In this embodiment, the nucleic acid molecule comprising the nucleotide barcode sequence is contacted with a first set of first detection probes for decoding the first sequential barcode position. Each first detection probe comprises a first flanking sequence complementary to at least a portion of the first spacer sequence of the first barcode position, a sequence complementary to a barcode subunit, a second flanking sequence complementary to at least a portion of the second spacer sequence of the first barcode position. Each first detection probe comprises a sequence complementary to a different barcode subunit within the panel, such that each detection probe is capable of hybridising to and detecting a different barcode subunit at said first barcode position. In this embodiment, the set of detection probes will typically contain at least as many members as the panel of barcode subunits, such that there is a complementary detection probe for each barcode subunit. In some embodiments, the first flanking sequence and/or the second flanking sequence may be complementary to the entire sequence of the corresponding spacer sequence i.e. the first flanking sequence may be complementary to the entire sequence of the first spacer sequence, and/or the second flanking sequence may be complementary to the entire sequence of the second spacer sequence.

Alternatively, the flanking sequences may be shorter than the corresponding spacer sequences, i.e. the first flanking sequence may be shorter than the first spacer sequence and/or the second flanking sequence may be shorter than the second spacer sequence. Detection probes having flanking sequences which are shorter than the corresponding spacer sequences have increased rates of discrimination and reduced rates of off-site binding, as the sequence complementary to a barcode subunit makes up a bigger proportion of the total length of the detection probe, and thus binding to a barcode position comprising a mismatching barcode subunit is less favourable.

When the nucleic acid molecule comprising the nucleotide barcode sequence is contacted with the first set of detection probes, the detection probe with the sequence complementary to the barcode subunit at the first sequential barcode position can hybridise to the nucleic acid molecule at said first sequential barcode position. A signal can then be detected from the reporter of the first detection probe which has hybridised to the nucleotide barcode sequence at the first sequential barcode position. The detection probes may each comprise a different reporter, such that each barcode subunit directly corresponds to a single reporter. As indicated above, the reporter may be such that absence of signal is reported (i.e. the reporter may be absent or may lack a detectable moiety). Alternatively, multiple detection probes may comprise the same reporter. In this case, multiple cycles of hybridisation of detection probes may be required to decode each barcode position.

In a representative example, each barcode position may comprise a barcode subunit selected from a panel of 16 barcode subunits. The barcode position could therefore be decoded using a single set of 16 detection probes, each comprising a sequence complementary to a different barcode subunit, and a different reporter. The nucleotide barcode sequence would be contacted with the set of detection probes, washed to remove unhybridised detection probes, and then a signal would be detected from the hybridised detection probe. The identity of the signal would then provide the identity of the barcode subunit present at that barcode position.

Alternatively, the same barcode position could be decoded in 2 stages, using 16 detection probes divided into 2 sets of 8 probes each. Each detection probe would comprise a sequence complementary to a different barcode sequence, and a reporter selected from 8 possible reporters, such that each reporter is present in 2 probes. The detection probes would then be divided into two sets, such that each set comprises 8 detection probes with 8 different reporters. The nucleotide barcode sequence would be contacted with a first set of 8 detection probes, and washed so as to remove any unhybridised detection probes. An attempt would then be made to detect a signal from any potential hybridised detection probe. If a signal is detected, the identity of the barcode subunit at the barcode position can be determined, based on the identity of the reporter that is observed. If no signal is detected, then the nucleotide barcode sequence would be contacted with a second set of 8 detection probes, and washed so as to remove any unhybridised detection probes. A signal would then be detected from the hybridised detection probe, and thus the identity of the barcode subunit present at that barcode position could be determined. It will be understood that in such an embodiment, the first set of probes would not include a reporter which reports absence of signal.

It will be evident that this principle of decoding a barcode position in stages using smaller sets of detection probes could be extended. For example, a barcode position comprising 1 of 16 possible barcode subunits could be decoded in 3 stages using 16 detection probes divided into 4 sets of 4 probes each.

This method of decoding a barcode position may be necessary when the number of barcode subunits in the panel is greater than the number of different reporters that are available. However, it may also be used in circumstances where this is not the case, as it can provide a greater signal to noise ratio. For example, it may be easier to detect a signal from a hybridised detection probe when a barcode position comprising 1 of 16 possible barcode subunits is decoded in stages using detection probes comprising only 4 different reporters, than when it is decoded using detection probes comprising 16 different reporters. Accordingly, this method is particularly useful in high density applications, where a large number of nucleotide barcode sequences are present in a small sample.

An alternative method for decoding a barcode position where the number of barcode subunits in the panel is greater than the number of different reporters that are available may involves the use of displacer probes to remove hybridised detection probes. Displacer probes are described above in the context of assisting removal of hybridised probes which have been read. However, they may also be used in a different context, to extend coding capacity. By detecting a first signal from a hybridised detection probe, using an appropriate displacer probe to potentially remove said hybridised detection probe, and attempting to detect a subsequent signal from a potentially hybridised detection probe, the number of barcode subunits which can be distinguished by a set of detection probes with a limited number of different reporters is increased.

In a representative example, using this method a barcode position comprising 1 of 16 possible barcode subunits can be decoded with a set of 16 detection probes comprising only 8 different reporters and a set of 16 corresponding displacer probes. The detection probes are designed such that each detection probe comprises a sequence complementary to a different barcode subunit and a reporter selected from 8 possible reporters, wherein each reporter is present in 2 detection probes. As outlined above, the displacer probes each comprise a sequence complementary to a different detection probe. The nucleotide barcode sequence may be contacted with the set of 16 detection probes, and washed to remove the unhybridised detection probes. A first signal may then be detected from the detection probe that has hybridised to the nucleotide barcode sequence. Given that the detection probes are designed such that each reporter corresponds to only 2 barcode subunits, the identity of this signal may be used to determine that the barcode subunit present at the given barcode position must be 1 of 2 specific barcode subunits. The nucleotide barcode sequence may then be contacted with a displacer probe complementary to 1 of the said 2 barcode subunits and washed. An attempt may then be made to detect a subsequent signal from the reporter of a potential hybridised detection probe. If the nucleotide barcode sequence was contacted with a displacer probe complementary to the hybridised detection probe, then the displacer probe will invade the hybrid between the nucleotide barcode sequence and the hybridised detection probe and thus mediate the displacement of the detection probe. In this case, a subsequent signal will not be detected, as there will be no detection probe hybridised to the nucleotide barcode sequence.

Conversely, if the nucleotide barcode sequence was contacted with a displacer probe that was not complementary to the hybridised detection probe, then the strand displacement reaction will not occur, the detection probe will remain hybridised, and a subsequent signal, the same as the first signal, will be detected. It is therefore possible to determine the identity of the barcode subunit at the given barcode position based on the first signal detected in combination with the presence or absence of a subsequent signal, i.e. the first signal in combination with the subsequent disappearance or maintenance of said signal, following the addition of the relevant displacer probe.

In one embodiment, the detection probes and the barcode subunit panel are designed such that each barcode subunit in the panel corresponds to a single specific reporter. Each reporter then corresponds to one (and only one) of the barcode subunits in the panel, which means that the signal detected from the reporter allows the identity of the barcode subunit at a given barcode position to be determined. It can be seen that, in this embodiment, given that each reporter corresponds to only a single barcode subunit, it is possible to determine the identity of a given barcode subunit based on the signal from a single detection probe.

Once the identity of a barcode subunit at a given barcode position has been determined, the nucleotide barcode sequence is then contacted with a next set of subsequent detection probes for decoding the next sequential barcode position. Again, each subsequent detection probe comprises a first flanking sequence complementary to at least a portion of the first spacer sequence of the next sequential barcode position, a sequence complementary to a barcode subunit, and a second flanking sequence complementary to at least a portion of the second spacer sequence of the next sequential barcode position. Each subsequent detection probe is therefore capable of hybridising to and detecting a different barcode subunit. The subsequent detection probe which hybridises to the barcode subunit at the next sequential barcode position hybridises to a sequence within the overlapping region of the preceding barcode position and thereby invades the hybrid between the hybridised preceding detection probe and the nucleotide barcode sequence, to displace the hybridised preceding probe.

The hybridisation of the subsequent detection probe thus constitutes a strand displacement reaction, wherein the hybridised preceding detection probe is displaced from the nucleotide barcode sequence. In this strand displacement reaction, the sequence complementary to the subsequent barcode subunit, and the second flanking sequence of the subsequent detection probe act as a toehold, hybridising to the nucleotide barcode sequence and allowing the first flanking sequence to invade the adjacent hybrid formed between the preceding detection probe and the nucleotide barcode sequence at the overlapping region between the preceding barcode position and the barcode position that is being read. This strand invasion by the first flanking sequence of the subsequent detection probe disrupts the hybridisation between the second flanking sequence of the preceding detection probe and the nucleotide barcode sequence, and thus promotes the displacement of the preceding detection probe. As discussed above, this partial invasion of the hybrid between the nucleotide barcode sequence and the preceding detection probe may be sufficient to cause the preceding detection probe to dissociate from the nucleotide barcode sequence. If this is not the case, and the preceding detection probe remains hybridised to the nucleotide barcode sequence despite the displacement of the second flanking sequence, then an additional displacer probe can be used. As hereinbefore described, each displacer probe comprises a sequence complementary to a different barcode subunit. When the displacer probes are used to displace a hybridised detection probe, following the detection of a signal from the reporter of said probe, the nucleotide barcode sequence may be contacted with the specific displacer probe comprising a sequence complementary to the hybridised detection probe, or with a whole set of displacer probes each comprising a sequence complementary to a different barcode subunit.

The detection probes used in this embodiment may be designed so as to promote this strand displacement reaction. In particular, it may be desirable to design the detection probes such that the first flanking sequence of each subsequent detection probe has a higher affinity for the spacer sequence in the overlapping region between the preceding barcode position and the barcode position that is being read than the second flanking sequence of the preceding detection probe. In a preferred embodiment, the first flanking sequence of each detection probe has a higher affinity for the first spacer sequence of the corresponding barcode position than the second flanking sequence of the detection probe has for the second spacer sequence of the corresponding barcode position. This increased affinity will drive the invasion of the hybrid between the nucleotide barcode sequence and the preceding detection probe by the first flanking sequence of the subsequent detection probe and therefore favour the invasion of the hybrid between the nucleotide barcode sequence and the preceding detection probe by the subsequent detection probe. If the preceding detection probe is more readily displaced then the method of decoding can be completed more quickly.

Accordingly, the detection probes used in the present invention may have an asymmetric design. In one embodiment, the first flanking sequence of each detection probe may be longer than the second flanking sequence. In one embodiment, the first flanking sequence of each detection probe is the same length as the spacer sequences, such that the first flanking sequence of each detection probe can hybridise to the entire length of the complementary first spacer sequence of the relevant barcode subunit. In particular, the first flanking sequence of subsequent detection probes can hybridise to the entire length of the second spacer sequence of the preceding barcode position. The second flanking sequence of each detection probe may be shorter than the first flanking sequence by at least 1, 2, 3, 4, 5, or more nucleotides. In addition, the second flanking sequence of each detection probe may be shorter than the spacer sequences by at least 1, 2, 3, 4, 5, or more nucleotides. In one representative embodiment, the first flanking sequence of each detection probe is 6 nucleotides in length. In one representative embodiment, the second flanking sequence of each detection probe is 4 nucleotides in length.

Alternatively, the strand displacement reaction may be promoted by varying the lengths of successive detection probes. By increasing the length of successive detection probes (and successive corresponding spacer sequences), the sequential displacement of each probe by the next is favoured. In one embodiment, the detection probes for successive barcode positions may increase in length by 2 nucleotides. For instance, for a system with 5 sets of detection probes, sets 1 to 5 may comprise probes having lengths of 14, 16, 18, 20, and 22 nucleotides, respectively.

Further, as noted above and shown in FIG. 5, a subsequent detection probe may have an extended binding site, which comprises also a complementary region capable of hybridising to the non-overlapping region of the preceding barcode position.

As further indicated above, also provided herein is a method of decoding a continuous nucleotide barcode sequence in which barcode subunits are overlapping. Such a method is depicted in FIG. 2, which shows such a barcode sequence design and successive detection probes for decoding it. FIG. 6 also shows the operation of 2 cycles of such a method. In such a method each barcode position comprises a barcode subunit pair comprising a first barcode subunit and a second barcode subunit, wherein the second barcode subunit from each barcode position at least partially overlaps with the first barcode subunit of the adjacent barcode position in the sequence. The order of barcode subunit pairs in each nucleotide barcode sequence defines a signal code sequence which comprises a signal code corresponding to each barcode subunit pair, and which is distinct from the signal code sequences of other nucleotide barcode sequences and identifies a given nucleotide barcode sequence.

In this embodiment, there are no spacer sequences between the barcode subunits. In a preferred embodiment, the second barcode subunit from each barcode position fully overlaps with the first barcode subunit of the adjacent barcode position, such that the second barcode subunit of one barcode position forms the first barcode subunit of the adjacent barcode position. In this case, the terminal barcode positions comprise an overlapping region comprising one barcode subunit, and a non-overlapping region comprising a second barcode subunit, whilst the non-terminal (or internal) barcode positions have two overlapping regions, each comprising a barcode subunit, and no non-overlapping regions. Effectively, adjacent barcode positions have one different barcode subunit and one common barcode subunit.

Each barcode subunit may be used multiple times in a single nucleotide barcode sequence, or may be used in multiple different nucleotide barcode sequences. In one embodiment, each nucleotide barcode sequence is completely unique, i.e. each barcode subunit is only used once and only appears in a single nucleotide barcode sequence.

The order of the barcode subunit pairs in each nucleotide barcode sequence defines a signal code sequence which comprises a signal code corresponding to each barcode subunit pair. The signal code sequence for a given nucleotide barcode sequence is distinct from the signal code sequences of other nucleotide barcode sequences, and thus can identify said nucleotide barcode sequence. Accordingly, in the practice of such a method, nucleotide barcode sequences may be designed to yield unique signal code sequences which can be used to differentiate the nucleotide sequence barcode.

Each barcode subunit pair in every nucleotide barcode sequence may be assigned a signal code, and each individual signal code may in turn be indicated by a given reporter. Accordingly, each nucleotide barcode sequence is assigned a corresponding signal code sequence, made up of the signal codes observed from the reporters on the detection probes that hybridise to each of the constituent barcode positions.

A given signal code may be assigned to multiple barcode subunit pairs in the same nucleotide barcode sequence, and/or to multiple barcode subunit pairs in different nucleotide barcode sequences. Each reporter may therefore be observed at multiple barcode positions in a single nucleotide barcode sequence, and/or at a given barcode position in multiple different nucleotide barcode sequences. As indicated above, it may therefore not be possible to determine the identity of the barcode subunit pair within a given barcode position solely from the signal detected from the detection probe which hybridises to that barcode position, but rather the signal code sequence needs to read in order to decode the nucleotide barcode sequence.

In this method, the nucleic acid molecule comprising the nucleotide barcode sequence is contacted with a first set of first detection probes for decoding the first sequential barcode position. Each detection probe comprises a sequence that is complementary to a different barcode subunit pair and a reporter, such that each detection probe is capable of hybridising to and detecting a different barcode subunit pair at said first barcode position. The detection probes may further comprise a displacer toehold overhang region, as hereinbefore described.

Once a signal has been detected from the reporter of the first detection probe which has hybridised to the nucleotide barcode sequence at the first sequential barcode position, and the signal code for the first barcode subunit pair has been identified, the nucleotide barcode sequence is contacted with a next set of subsequent detection probes for decoding the next sequential barcode position. The subsequent detection probe which hybridises to the barcode subunit at the next sequential barcode position is capable of hybridising to a sequence within the overlapping region between the preceding barcode position and the barcode position that is being read. Accordingly, when the subsequent detection probe hybridises to the nucleotide barcode sequence, it invades the hybrid between the hybridised preceding detection probe and the nucleotide barcode sequence, and thus initiates a strand displacement reaction which disrupts the hybrid between the preceding detection probe and the nucleotide barcode sequence and therefore displaces the preceding detection probe.

It will be seen that a subsequent detection probe hybridises to a barcode subunit at the next sequential position that is different to those of the preceding position. It is also capable of hybridising to the barcode subunit which is common in the preceding barcode position (occupied by the preceding detection probe). Once hybridised to the different barcode subunit, the subsequent detection probe may therefore hybridise to the common subunit, to displace (or at least to initiate the displacement of) the preceding detection probe. In other words, a toehold exchange occurs.

Accordingly, in such an embodiment the binding site (the complementary region) of a detection probe (particularly in a subsequent detection probe) for the second subunit of a subunit pair (first and second being defined relative to the direction in which the barcode sequence is decoded) can be seen to provide a toehold for a subsequent detection probe to bind, whilst the preceding barcode position is occupied by a preceding detection probe.

As described above, the steps of hybridising a detection probe to a barcode position, detecting a signal from said detection probe, and therefore identifying the signal code for said barcode position are then effectively repeated in order to identify signal codes for subsequent barcode positions. The preceding hybridised detection probes may be removed from the nucleotide barcode sequence once a signal has been detected from their reporters via a strand displacement reaction. If necessary, additional displacer probes may be used, as hereinbefore described. The steps of the method are repeated until signal codes have been identified in respect of a sufficient number of barcode positions to decode the nucleotide barcode sequence.

A barcode subunit in such a method may be of any length permitting specific hybridisation of a detection probe. For example it may be at least 8 bases long, more particularly at least 9 or 10 bases long. For example it may be 8-20, 8-15, 8-12, 9-20, 9-18, 9-15, or 9-12 bases long. In an embodiment it may be 10 bases long.

As discussed above, the decoding process of the methods herein can be seen to involve the conversion of a nucleotide barcode sequence into a signal code sequence which identifies the barcode sequence. This can be seen particularly to apply to the method described above for decoding a continuous barcode sequence made up of pairs of barcode subunits which overlap in one barcode subunit. In a situation where there are multiple barcode subunits, and particularly multiple unique barcode subunits, the available reporters have to be "re-used" in order to read the barcode. Thus, a unique signal code sequence is needed to distinguish the nucleotide barcode sequences. This can be viewed from the converse, in that to distinguish multiple different target nucleic acid molecules in a sample, the target nucleic acids are each assigned a unique signal code sequence (e.g. a unique colour code sequence, e.g. made up of the colours yellow, green, blue and red). A nucleotide barcode sequence can be designed to correspond to each unique signal code sequence and the target nucleic acid molecules in a sample can each be provided with a distinct nucleotide barcode sequence. The barcode sequence corresponds to, or represents the signal code sequence. The barcode subunits of that sequence may be unique (but need not be). Different pairs of barcode subunits may be "read" by different detection probes carrying the same reporter to yield the same signal code. Thus, individual pairs of subunits cannot be distinguished by the signal code they yield, but the sequence of barcode subunits in the sequence barcode may be designed to yield a particular, unique signal code sequence. The barcode sequence may accordingly be interrogated using detection probes that match to that barcode sequence. In other words, detection probes cognate to, or unique to, the subunit pair at each position may be used, in sequence, to interrogate each position sequentially and obtain the signal code sequence. In this sense, it can be seen that the method involves an interrogation to see if a particular signal code sequence can be detected from a nucleotide barcode sequence.

In FIG. 7, a decoding scheme involving barcode pairs is shown. This general decoding scheme allows a target sequence to be decoded using a barcode comprising 6 barcode positions. Each barcode position comprises two different subunits, each selected from a set of 4 potential subunits. Each subunit is assigned a differently coloured label, as shown in FIG. 7. This scheme relies on each detection L-probe having 2 adjacent sequences. The first of these sequences is complementary to the first barcode subunit in the relevant barcode position, which is common with the preceding detection L-probe, whilst the second sequence is complementary to the second barcode subunit in the position, which is common with the next detection L-probe. The detection probes each further comprise a detectable label in the form of a fluorophore which corresponds to the second barcode subunit to which they are complementary.

The method of decoding comprises first contacting the barcode sequence with a set of probes comprising sequences complementary to subunits which make up the first barcode position. In this scheme, there are 4 possible detection L-probes for the first position, each comprising a sequence complementary to a pair of barcode subunits assigned the same coloured label (i.e. AF, BG, CH, DI). The first detection probe which comprises a sequence complementary to the barcode sequence hybridises at the first barcode position, and can then be detected. The signal detected from the label of the detection probe that has hybridised to the first barcode position can be used to determine the identity of the two barcode subunits in the first barcode position.

This information also provides the identity of the first barcode subunit in the second barcode position (as the positions overlap). The signal detected from the detection probe hybridised to the barcode sequence at the first barcode position can therefore be used to determine which detection probes are necessary to investigate the identity of the second barcode position. For example, if a yellow signal from Cy®3 (dye) is observed following the first contacting step, this indicates that the first barcode position comprises subunits AF. In this example, the next of step of the scheme would involve contacting the nucleotide barcode sequence with detection probes each comprising a first sequence (binding/recognition site) complementary to the sequence of subunit F, and a second sequence (binding/recognition site) complementary to one of subunits J, K, L or M. The second sequence of the subsequent detection probe which is complementary to the barcode sequence (i.e. the binding site that is complementary to the second subunit of the second barcode position that is present) can hybridise directly to the barcode and act as a toehold, mediating the displacement of the preceding detection probe by the first sequence of the subsequent detection probe, which is complementary to the sequence of subunit F (i.e. by the binding site in the second detection probe that is complementary to the first subunit of second barcode position). The second detection probe can then be detected, and the identity of the second barcode position can be determined. This process is then repeated to investigate the subsequent barcode positions. Accordingly, it is only necessary to contact the barcode sequence with 4 detection probes at each decoding cycle.

In total, the scheme requires 4 possible detection L-probes for the first barcode position, and 16 possible detection L-probes for each subsequent position (one for each combination of two sequence parts selected from a possible 4 in each subunit). Thus, the total amount of detection L-probes needed is 4+16*5=84 detection L-probes for a universal decoding scheme.

The entire binding region for this decoding scheme will be 70 bp long if a hybridization length of 20 bp, with an overlap of 10 bp, is utilized. A 70 bp binding region is fairly long, but is of feasible length to be used as a barcode, for example within a hybridisation probe such as a padlock probe. If desired, the length can be reduced by shortening the hybridization length of the detection L-probes from 20 bp to 14 bp for example. The 14 bp design would only require a total hybridization length of 49 bp.

As can be seen from the above, in such a method, the first detection probe may recognize a pair of subunits both decoding the same colour. The second detection probe also recognizes two subunits, which act as a pair in order to allow the probe fully to hybridize. The binding sites in the detection probes for the two respective barcode subunits may be viewed as corresponding to these subunits (in effect, the detection probe has corresponding "subunits"). The difference between the first and the second detection probes is that in the second detection probe the signal code is encoded in only one subunit and the other subunit is the displacer, effectively displacing the first detection probe by encoding for the signal of the first detection probe. Accordingly, in such a method, involving a barcode having barcode positions having subunit pairs in which one of the subunits overlaps with an adjacent position, only the second barcode subunit can be seen to provide, or encode, the signal code. Analogously, only the corresponding second subunit of a detection probe can be seen to provide the signal code which is decoded. In such a scheme, the second subunit of the detection probe, which acts as the toehold of a subsequent detection probe, provides the signal code which contributes to the signal code sequence (i.e. which is specific for the signal code of that barcode position, to which the detection probe is directed). This subunit, which provides the toehold of the detection probe, is the sequence which can bind to the barcode sequence without impedance, and which is specific for the signal code of that barcode position; the first common (overlapping) subunit of a subsequent detection probe is specific to the toehold of the preceding detection probe. In effect, the second subunit of the barcode position, and the corresponding second subunit which provides the toehold of the detection probe, is the "coding" portion, which yields or provides the signal code.

The main advantage of the design utilizing the decoding scheme outlined in FIG. 7 is the lack of stripping the tissue sections between each decoding cycle. As the stripping of tissue section is generally performed using 100% formamide, this design is safer to perform and carries less chance of damaging the tissue section and its morphology. High levels of formamide have also been shown to damage the epitopes used in immunostaining. Reducing the use of high levels of formamide in the in situ sequencing procedure allows it to be fully compatible with subsequent immunostaining to identify morphology and/or protein levels of interest to verify a knockdown/out in situ, for example.

The method for interrogation of paired subunits as described above represents such a method wherein a linear barcode sequence of multiple sequential barcode positions is sequentially interrogated to yield a signal code sequence. However, an alternative method is also provided and disclosed herein, in which a linear barcode sequence of multiple sequential barcode positions, each corresponding to and yielding a signal code, is not required. The principle of the method is that a signal code may be generated by a series of sequential exchanges of detection probes, each yielding a signal. The detection probes are exchanged by sequential toehold-mediated displacement reactions. It is not necessary, however, for each detection probe to have a unique binding site. A signal code sequence may be provided instead by repeatedly interrogating the same two barcode positions in turn, one to the other and back again, using detection probes provided with different reporters, which yield distinguishable signals (including absence of signal, or alternatively termed a blank or "dark" reporter). In such a method rather than detection probes which sequentially displace themselves in one direction, the detection probes are sequentially displaced in both a forward and reverse direction. The number of binding sites for the detection probes is reduced to two, and the nucleotide barcode sequence distinguishing each nucleic acid molecule is therefore simplified. It can be defined instead as a detection tag, or detection site comprising two binding sites. Each separate nucleic acid molecule in the sample will have a unique barcode sequence (or alternatively termed "detection tag"). It comprises only two barcode positions (or detection probe binding sites), and only two different barcode subunits. Each barcode position comprises one different barcode subunit and one common subunit which is shared by the other position (in effect the whole barcode is made up only of two subunits, one of which is unique to one barcode position, and the other of which is shared). Thus the two barcode positions overlap in a barcode subunit, as described above, which allows a subsequent detection probe binding to one of the two barcode positions to displace a preceding detection probe hybridised to the other barcode position. The barcode sequence may be interrogated by a set of detection probes unique for that barcode. The set of detection probes is cognate for that barcode sequence and is designed to be used in sequence to generate a particular signal code sequence. This method thus relies on using a particular set of detection probes in sequence. The detection probes in a set are provided for use in a particular order, to generate a pre-determined signal code sequence. In this way, the barcode can be used to create a signal code sequence using the detection probes. The detection probes may be designed and provided with reporters as described for the other methods above (e.g. provided directly with reporters, or indirectly, by having reporter overhangs which bind reporter probes etc.).

Accordingly in another aspect, the present disclosure and invention can be seen to provide a method of decoding a nucleotide barcode sequence in a nucleic acid molecule, wherein the nucleotide barcode sequence corresponds to a specific signal code sequence that may be derived by interrogating the nucleotide barcode sequence with sequential detection probes each yielding a signal and the signals together make up the signal code sequence, and wherein the nucleotide barcode sequence comprises at least two adjacent barcode positions, each barcode position comprising a barcode subunit pair comprising a first barcode subunit and a second barcode subunit, wherein the second barcode subunit from each barcode position at least partially overlaps with the first barcode subunit of the adjacent barcode position in the sequence, said method comprising:

(i) contacting the nucleic acid molecule with a first detection probe for generating a signal code for the first position of the signal code sequence, and allowing the detection probe to hybridise to the nucleic acid molecule, wherein the detection probe comprises a recognition sequence that is complementary to the barcode subunit pair that is present at the first barcode position and a reporter;

(ii) detecting a signal from the reporter of the first detection probe which has hybridized to the nucleotide barcode sequence at the first barcode position;

(iii) identifying the signal code for the first position of the signal code sequence from the signal detected in (ii);

(iv) contacting the nucleotide barcode sequence with a subsequent detection probe for generating a signal code for the next position of the signal code sequence, and allowing the detection probe to hybridise to the nucleic acid molecule, wherein the detection probe comprises a recognition sequence that is complementary to the barcode subunit pair that is present at the adjacent barcode position, and a reporter, and wherein the subsequent detection probe which hybridises to the barcode subunit at the adjacent position hybridises to a sequence within the overlapping portion of the preceding barcode position (more particularly to a sequence in the second barcode subunit of the preceding barcode position), and thereby initiates a strand displacement reaction which displaces the hybridised preceding detection probe;

(v) detecting a signal from the reporter of the subsequent detection probe which has hybridized to the nucleotide barcode sequence at the adjacent barcode position;

(vi) identifying the signal code for the next position of the signal code sequence from the signal detected in (v);

(vii) repeating steps (iv)-(vi) to identify signal codes for subsequent signal code sequence positions until sufficient signal codes have been identified to decode the nucleotide barcode sequence, wherein detection probes for identifying the subsequent signal codes in the signal code sequence have (a) recognition sequences that are complementary to barcode subunit pairs that are present at subsequent sequential barcode positions in a nucleotide barcode sequence comprising multiple sequential adjacent barcode positions, or (b) recognition sequences that are complementary to the barcode subunit pairs that are present at the first and second barcode positions of a nucleotide barcode sequence comprising two adjacent barcode positions, and a reporter;

wherein the first barcode position can be any barcode position in the nucleotide barcode sequence.

By "specific" is meant that the signal code sequence is specific for that nucleotide barcode sequence, that is, it distinguishes from other nucleotide barcode sequences. The signal code sequence is distinct from the signal code sequences of other nucleotide barcode sequences and identifies a given nucleotide barcode sequence.

It will be seen that a method comprising step (vii)(a) as defined above corresponds to the method described above for decoding a continuous nucleotide barcode sequence comprising multiple sequential barcode positions in which each barcode position comprises a barcode subunit pair comprising a first barcode subunit and a second barcode subunit, and barcode subunits between adjacent barcode positions in the sequence are overlapping. In such a method, the subsequent detection probes displace preceding detection probes in one direction (forward or reverse), and a linear sequence of barcode positions can be read.

A method comprising step (vii)(b) on the other hand represents an alternative method which, as explained above, reads the same two barcode positions back and forth using different detection probes in sequence, which displace each other in alternating forward and reverse directions, to generate the signal code sequence. A schematic example of such a method is outlined in FIG. 8A.

A variation of such a method is shown in FIG. 8B. In this embodiment, the detection probes may hybridise not only to a barcode position in the barcode sequence, but also to a general region present in the nucleic acid molecule, outside the barcode sequence. Thus, the nucleic acid molecule may comprise general regions flanking the barcode sequence. The general regions are common to different nucleic acid molecules. The use of such general (or common) regions allows barcode sequences to be shortened. The general, or common, region together with a barcode position may thus together provide, or constitute, the binding site for a detection probe. In a further variation, the use of such common regions facilitates a modification to the "back-and-forth" decoding method, wherein additional displacer probes are used to assist in the displacement and removal of a preceding detection probe. This is described further below, and exemplified in Example 4 (see also FIGS. 14 to 18). The common region can be used to provide a binding site, or a part thereof, for a displacer probe. In particular, rather than using displacer probes which comprise a portion (domain) which is specific for, or complementary to, a barcode position, the displacer probe can be designed to have a domain which is complementary to the common region (as well as a domain complementary to a toehold sequence in a detection probe). In this way, a separate set of displacer probes for each barcode sequence do not need to be designed.

Detection probes are used in sequence, and are provided with reporters to yield a signal code which is specific for a particular barcode sequence.

The method may be carried out in multiplex to decode different nucleotide barcode sequences. Thus, the method may be performed on a sample comprising multiple different nucleic acid molecules, each comprising a different nucleotide barcode sequence. The method may differentiate a nucleotide barcode sequence from other nucleotide barcode sequences. In such a method, each barcode sequence will be decoded by its own series, or sequence, of detection probes. In other words, each nucleotide barcode sequence will have a matching (or, alternatively defined, cognate or dedicated) series (or set) of detection probes for decoding it. The probes will be used sequentially (e.g. in a set series or sequence) for each nucleotide barcode sequence, to derive, step-wise, a sequence of signal codes, to yield the signal code sequence, and thereby identify, or decode, the barcode sequence. Thus, each barcode sequence has a unique sequence of detection probes, and this will yield (or encode) a unique signal code sequence, which identifies the nucleotide barcode sequence and hence a target nucleic acid molecule (which ultimately may correspond to a particular gene, or other analyte target). When multiple nucleotide sequence barcodes are decoded together in a sample (e.g. in parallel, on a sample), the sample containing the barcodes is (or more particularly the nucleic acid molecules comprising the barcodes are) contacted with a set of detection probes for decoding a barcode position (i.e. a first or subsequent position), wherein each detection probe in the set is capable of hybridising to and detecting a particular barcode subunit pair which may be present at that barcode position. In an embodiment, each detection probe in the set may be capable of hybridising to and detecting a different barcode subunit pair at that barcode position. Thus, the set of detection probes used in each cycle (i.e. to derive a signal code for a signal code position) may comprise detection probes for decoding multiple different barcode sequences that may be present. Whilst the sequence of detection probes is unique to a particular barcode sequence, individual members of that sequence may be found in the detection probe sequences for decoding different barcode sequences. Thus, detection probes may be "shared" between detection probe sets (sequences) for decoding different nucleotide barcode sequences.

In a particular embodiment of this aspect there is provided a method of decoding a nucleotide barcode sequence in a nucleic acid molecule, wherein the nucleotide barcode sequence corresponds to a specific signal code sequence that may be derived by interrogating the nucleotide barcode sequence with sequential detection probes each yielding a signal and the signals together make up the signal code sequence, and wherein the nucleotide barcode sequence comprises first and second adjacent barcode positions, each barcode position comprising a barcode subunit pair comprising a first barcode subunit and a second barcode subunit, wherein the second barcode subunit from the first barcode position at least partially overlaps with the first barcode subunit of the second barcode position, said method comprising:

(i) contacting the nucleic acid molecule with a first detection probe for generating a signal code for the first position of the signal code sequence, and allowing the detection probe to hybridise to the nucleic acid molecule, wherein the detection probe comprises a recognition sequence that is complementary to the barcode subunit pair that is present at the first barcode position and a reporter;

(ii) detecting a signal from the reporter of the first detection probe which has hybridized to the nucleotide barcode sequence at the first barcode position;

(iii) identifying the signal code for the first position of the signal code sequence from the signal detected in (ii);

(iv) contacting the nucleotide barcode sequence with a subsequent detection probe for generating a signal code for the next position of the signal code sequence, and allowing the detection probe to hybridise to the nucleic acid molecule, wherein the detection probe comprises a recognition sequence that is complementary to the barcode subunit pair that is present at the second barcode position, and a reporter, and wherein the subsequent detection probe which hybridises to the barcode subunit at the adjacent position hybridises to a sequence within the overlapping portion of the preceding barcode position (more particularly to a sequence in the second barcode subunit of the preceding barcode position), and thereby initiates a strand displacement reaction which displaces the hybridised preceding detection probe;

(v) detecting a signal from the reporter of the subsequent detection probe which has hybridized to the nucleotide barcode sequence at the adjacent barcode position;

(vi) identifying the signal code for the next position of the signal code sequence from the signal detected in (v);

(vii) repeating steps (iv)-(vi) to identify signal codes for subsequent signal code sequence positions until sufficient signal codes have been identified to decode the nucleotide barcode sequence, wherein in repeated steps the detection probes for identifying the subsequent signal codes in the signal code sequence respectively have recognition sequences that are complementary to the barcode subunit pairs that are present at the first and second barcode positions of the nucleotide barcode sequence such that detection probes successively hybridise to and displace preceding detection probes from the first and second barcode positions;

wherein the first barcode position can be the 5' or the 3' barcode position in the nucleotide barcode sequence.

The methods described above involve assigning a signal code sequence to a given nucleotide barcode sequence, and in turn to a given nucleic acid molecule, and determining that signal code sequence in order to detect or identify the nucleotide barcode sequence, and hence the nucleic acid molecule.

Viewed from another aspect, the above methods can therefore be seen as, or alternatively defined as, a method of detecting a nucleic acid molecule, wherein the method comprises:

(a) assigning a unique signal code sequence to the nucleic acid molecule, wherein the signal code sequence is specific to that molecule;

(b) providing the nucleic acid molecule with a nucleotide barcode sequence that corresponds to the signal code sequence, wherein the signal code sequence may be derived by interrogating the nucleotide barcode sequence with sequential detection probes each yielding a signal and the signals together make up the signal code sequence, and wherein the nucleotide barcode sequence comprises at least two adjacent barcode positions, each barcode position comprising a barcode subunit pair comprising a first barcode subunit and a second barcode subunit, wherein the second barcode subunit from each barcode position at least partially overlaps with the first barcode subunit of the adjacent barcode position in the sequence;

(c) performing steps (i) to (vii) as defined above to generate a signal code sequence to decode the nucleotide barcode sequence and detect the nucleic acid molecule.

The disclosures herein in relation to any of the first set of methods presented above for decoding a nucleotide barcode sequence, and the detection probes and how they are used etc., may be applied analogously to the alternative methods discussed above.

These decoding and nucleic acid molecule detection methods involving detection probes displacing each other back and forth at adjacent barcode positions may be applied more generally to detect a nucleic acid molecule. In this case, the detection probes act by interrogating a target nucleotide sequence within the nucleic acid molecule. Accordingly, in one aspect the present invention provides a method of detecting a nucleic acid molecule, wherein the method comprises:

(a) assigning a unique signal code sequence to the nucleic acid molecule, wherein the signal code sequence is specific to that molecule, wherein the signal code sequence may be derived by interrogating a target nucleotide sequence within the nucleic acid molecule with a sequence of detection probes, each detection probe yielding a signal and the signals together make up the signal code sequence, and wherein the target nucleotide sequence comprises first and second domains, each domain comprising a first subunit and a second subunit, wherein the second subunit of the first domain at least partially overlaps with the first subunit of the second domain in the target nucleotide sequence;

(b) contacting the nucleic acid molecule with a first detection probe for generating a signal code for the first position of the signal code sequence, and allowing the detection probe to hybridise to the nucleic acid molecule, wherein the detection probe comprises a recognition sequence that is complementary to the first and second subunits of the first domain and a reporter;

(c) detecting a signal from the reporter of the first detection probe which has hybridized to the nucleic acid molecule at the first domain;

(d) identifying the signal code for the first position of the signal code sequence from the signal detected in (c);

(e) contacting the nucleic acid molecule with a subsequent detection probe for generating a signal code for the next position of the signal code sequence, and allowing the detection probe to hybridise to the nucleic acid molecule, wherein the subsequent detection probe comprises a recognition sequence that is complementary to the first and second subunits of the second domain, and a reporter, and wherein the subsequent detection probe hybridises to a sequence in the second subunit of the preceding domain, and thereby initiates a strand displacement reaction which displaces the hybridised preceding detection probe;

(f) detecting a signal from the reporter of the subsequent detection probe which has hybridized to the nucleic acid molecule at the adjacent domain;

(g) identifying the signal code for the next position of the signal code sequence from the signal detected in (f);

(h) repeating steps (e)-(g) to identify signal codes for subsequent signal code sequence positions until sufficient signal codes have been identified to detect the nucleic acid molecule, wherein in repeated steps the detection probes for identifying the subsequent signal codes in the signal code sequence respectively have recognition sequences that are complementary to the subunits that are present at the first and second domains of the nucleotide barcode sequence such that detection probes successively hybridise to and displace preceding detection probes from the first and second barcode positions;

wherein the first barcode position can be the 5' or the 3' barcode position in the nucleotide barcode sequence.

The method may be performed in multiplex to detect multiple different nucleic acid molecules present in a sample, analogously to the multiplex detection methods disclosed above for decoding or detecting nucleic acid molecules comprising barcodes. Each target nucleic acid molecule to be detected may be detected by its own series, or sequence, of detection probes. In other words, each nucleic acid molecule will have a matching (or, alternatively defined, cognate or dedicated) series (or set) of detection probes for detecting it.

The target nucleotide sequence interrogated by such a method may be a target sequence within a DNA or RNA molecule by means of which that the nucleic acid molecule under test (i.e. being detected) may be distinguished from other nucleic acid molecules. In other words, it may be a target sequence which is specific to that molecule, and identifies that molecule. The target sequence may be provided artificially within the nucleic acid molecule, that is it may be added or incorporated into the molecule, as a detectable sequence for detecting the molecule. In other words, it may be a tag sequence, or a nucleotide barcode sequence, such as those described above in the barcode decoding methods disclosed herein. In some embodiments, the target sequence may be included within a nucleic acid molecule used as a probe (or part of a probe) for the detection of a target analyte. For example, the nucleic acid molecule comprising the target nucleotide sequence may be linked to a binding partner having affinity for a target analyte for the detection of that analyte. In such an embodiment, the nucleic acid molecule constitutes a detectable moiety (e.g. tag or barcode-containing molecule) which allows the binding of the binding partner to its target analyte to be detected. Such a binding partner may for example be used to detect a non-nucleic acid analyte, e.g. a protein. The binding partner may be any affinity binding partner, including particularly a non-nucleic acid binding partner e.g. a protein or proteinaceous molecule. An example of such a binding partner is an antibody. In such an embodiment, detection of the nucleic acid molecule, via the target sequence, indicates the presence and location of the antibody, and therefore the presence and location of the analyte to which the antibody is bound.

Alternatively, the target sequence may be a sequence which occurs naturally in the molecule to be detected (i.e. it can be a native sequence). Thus, a specific sequence which occurs in a target nucleic acid molecule, or in its complement, may be selected as the target nucleotide sequence. One may thus select adjacent target sequences, which have an overlapping region, and which are designated as first and second domains according to the method set out above. Each domain has two (first and second) subunits. The overlapping region may be designated as one subunit of the first and second domains, and the non-overlapping regions of the first and second domains represent the other subunit of the respective domains. Accordingly, the target nucleotide sequence may be a specific target sequence which is present in a native genomic DNA or in a naturally occurring RNA molecule, or in a cDNA or amplification product generated therefrom. In a particular embodiment, the nucleic acid molecule may be detected in situ in a cell or tissue sample. The cell sample may be a cell culture.

In some embodiments, a given nucleic acid molecule may comprise multiple target nucleotide sequences, each of which can be assigned the same signal code sequence, and interrogated by separate sets of detection probes.

It will be understood that any of the "back and forth" detecting or decoding methods disclosed herein may involve the use of displacer probes to assist in the displacement of a preceding detection probe. Thus, they may be performed using detection probes in the form of U-probes. Such a method using 2-site detection probe displacement is termed "2-LSD" herein. The use of displacer probes is described above.

As outlined above, such U-probes may be designed to hybridise to a given barcode position, or domain within a target nucleotide sequence, with 2 single-stranded overhangs, one for a reporter probe and the other for a displacer probe. Accordingly, a given detection probe may be displaced from both sides simultaneously; on one side by the subsequent detection probe hybridising to the overlapping region shared between the detection probe binding sites; and on the other side by the displacer probe hybridising to the displacer probe overhang. This double displacement reaction is extremely efficient, and thus allows for detection probes to be switched quickly between sequencing cycles, without the need for chemical stripping (or any of the damage to the sample that is associated therewith).

In some embodiments, the displacer probe overhang (i.e. the displacer toehold overhang) used in the detection probes may be common for all detection probes capable of hybridising to a given binding site. The use of such detection probes with "back and forth" is particularly advantageous, as such methods involve the use of only 2 detection probe binding sites, and thus it can be seen that only 2 displacer probe overhangs will be present across all of the detection probes (one for each binding site). Accordingly, a single displacement probe can be used to simultaneously displace detection probes bound to an equivalent barcode position from all of the RCPs within a given sample simultaneously (together with the displacement mediated by the subsequent detection probes). This further increases the efficiency of the method as a whole, and reduces the cost of the method, as fewer different probes are required.

To facilitate a common displacer probe overhang to be used in the detection probes, a common region may be provided adjacent to each of the two barcode positions in a "back and forth" barcode (see FIG. 14, and Example 4, for example). The common region and the barcode position (comprising first and second barcode subunits) together provide a binding site for a detection probe. A displacer probe is designed to bind to the common displacer probe overhang of the detection probes and to the common region adjacent to a barcode position. By being able to bind to the common region, invasion is facilitated of the hybrid between the barcode sequence and a hybridised detection probe. In this way, there is a generic or common toehold region in all the detection probes which binds to the first barcode position, and a different generic common toehold region in all the detection probes which binds to the second barcode position. Similarly, there is a generic common region which allows binding of the displacer probe adjacent to the first barcode position, and a different generic or common region adjacent to the second barcode position. Thus only 2 displacer probes need to be provided, one for use with each of the detection probes used for interrogating the first barcode position, and another for use with each of the detection probes used for interrogating the second barcode position in any barcode sequence, that is for any target.

In all methods and embodiments herein the detection probes may comprise naturally occurring nucleotides and may thus be in the form of a DNA or RNA oligonucleotide probe. However, they may alternatively, or additionally, comprise artificial or synthetic nucleotides (i.e. nucleotide analogues), and hence the detection probe may comprise, or may be composed of, any nucleic acid. Thus, the detection probes may be DNA, RNA, PNA, LNA, GNA and/or TNA.

The present methods and embodiments may further involve contacting the nucleic acid molecule with an anchor probe. As used herein, the term "anchor probe" refers to a probe comprising a sequence complementary to an anchor probe binding region, which is present in all target nucleic acid molecules, and a reporter, such as a detectable label, such that it can be detected. Suitable reporter arrangements are disclosed herein in relation to detection probes. The detection of the anchor probe via the reporter confirms the presence of the target nucleic acid molecule.

The target nucleic acid molecule may be contacted with the anchor probe prior to, concurrently with or after being contacted with the first set of detection probes. In some embodiments, the target nucleic acid molecule may be contacted with the anchor probe during multiple decoding cycles. In some embodiments, multiple different anchor probes comprising different sequences and/or different reporters may be used to confirm the presence of multiple different target nucleic acid molecules. The use of multiple anchor probes is particularly useful when using a large number of target nucleic acid molecules, as it allows for optical crowding to be reduced, and for target nucleic acid molecules to be more clearly resolved.

It will be evident that the present methods of decoding a nucleotide barcode sequence, and the nucleotide barcode sequence designs described herein may be applied to any scenario where it is desired to detect, quantify and/or locate a number (i.e. multiplicity) of target nucleic acid molecules. The method may be used for in situ applications to detect or assess gene expression, including for example in situ sequencing. In addition, the method may be applied in vitro to distinguish a set of target nucleic acid molecules, for example following an amplification reaction. The target nucleic acids may be probe molecules, or may be, or may be derived from, target nucleic acid molecules present in any sample under investigation. The nucleic acid molecules which comprise the nucleotide barcode sequences may thus similarly comprise or consist of any nucleic acid, but typically they will comprise DNA or RNA. In some embodiments, the nucleic acid molecules may comprise cDNA. In other embodiments they may comprise amplicons of target molecules under test (e.g. analyte nucleic acid molecules) or probes.

As indicated above, a barcode sequence may be provided directly within a nucleic acid molecule, for example it may be linked directly to a nucleic acid molecule, for example by ligation (for example an adaptor containing a barcode sequence may be ligated to a set of nucleic acid molecules under test), or it may be incorporated, for example into an amplification product, e.g. by the use of a primer containing the barcode sequence, or it, or its complement, may simply be provided as part of a nucleic acid molecule, e.g. where the molecule is a probe or some other synthetic molecule.

Alternatively, a probe which hybridises to a nucleic acid molecule under test may be used indirectly to introduce, or provide, a barcode. These probes typically comprise a sequence(s) complementary to a portion of their respective target nucleic acid molecules, and a separate, non-target complementary sequence, which contains the barcode.

Thus, by way of example, a hybridisation probe may be designed to hybridise specifically to a nucleic acid molecule under test. The nucleic acid molecule under test may be e.g. an analyte nucleic acid molecule present in a sample, or a cDNA or an amplicon thereof, or it may be an oligonucleotide molecule which is provided as a proxy for an analyte under test (for example a protein or other analyte in a sample may be detected by an antibody or other analyte-specific binding partner, which is provided with an oligonucleotide, and the hybridisation probe may be designed to hybridise to that oligonucleotide in order to detect the antibody, and hence the analyte; similarly an oligonucleotide molecule may be generated as part of an analyte detection assay, e.g. an extension or ligation product may be generated as the result of a proximity assay). Analogously, rather than a nucleic acid molecule being the target for a probe which contains the barcode sequence, the barcode sequence may be included with the nucleic acid molecule. Thus, a binding partner for an analyte (e.g. an antibody) may be provided with a nucleic acid molecule containing a barcode sequence, as described above. In other words, a conjugate may be provided comprising a binding partner (e.g. an antibody) for detecting an analyte, and a nucleic acid molecule comprising a barcode sequence linked, directly or indirectly, to the binding partner.

Such a hybridisation probe may be a padlock probe, and different padlock probes for different analyte or test nucleic acids may be provided with different barcode sequences, for example in the backbone part of the padlock between the target binding sites of the padlock.

Amplification of such a padlock probe by rolling circle amplification (RCA) will produce a concatemeric nucleic acid product (termed an RCP; rolling circle product) which comprises multiple repeat complementary copies of the padlock sequence (and hence of the barcode sequence) linked in tandem. Such RCPs may represent nucleic acid molecules which may be subject to the present methods. An RCP will contain multiple repeat copies of a barcode sequence, to which the detection probes described herein may be directed. (Technically, the RCP will contain complements of the barcode sequence contained in the padlock probe, but these may be regarded as the barcodes which are the target of the present methods; the terms "barcode" or "barcode sequence" etc. are thus used herein to refer to include complementary copies of a given barcode sequence. Thus, a probe can be provided with barcode which is copied as a homologous or complementary copy into a target molecule to be detected, etc.).

Moreover, each nucleic acid molecule may be targeted by multiple hybridisation probes, each providing a different barcode sequence. The use of multiple hybridisation probes thus allows for several barcode sequences to be provided for the same nucleic acid molecule. The barcode sequences can then be decoded with separate sets of detection probes, either at the same time or sequentially. This is useful for reducing optical crowding in dense samples with either a large number of different nucleic acid molecules or a large number of copies of the same nucleic acid molecule. The multiple hybridisation probes may each hybridise to the same site or to separate sites on the nucleic acid molecule.

Rather than incorporating a barcode directly into a padlock probe, the multiple repeat padlock complementary sequences which are contained in the RCP may themselves be hybridised to intermediate or sandwich probes and these intermediate or sandwich probes may be provided with a barcode nucleotide sequence. Thus a padlock probe may be provided with a tag sequence, the complement of which is capable of hybridising to an intermediate or sandwich probe (i.e. the tag sequence may be identical to, or homologous to, a sequence contained in the binding site of the intermediate/sandwich probe).

These intermediate or sandwich probes may be in the form of so-called "L-probes" or U-probes, as discussed above, which may contain one or two overhang regions which contain a barcode sequence. Indeed, a barcode-containing sandwich/intermediate L-probe or U-probe need not be limited to those for detecting RCPs and consequently a sandwich/intermediate probe for use in any nucleic acid based detection assay or method may be used as a subject nucleic acid molecule in the present methods.

As noted above, also disclosed herein are alternative methods of detecting a target nucleic acid molecule. In one embodiment the present invention provides a method of detecting a target nucleic acid molecule, wherein the target nucleic acid molecule is detected using a padlock probe specific for said target molecule which is circularised upon hybridisation to a target sequence in the target nucleic acid molecule and which is provided with a nucleotide barcode sequence to identify the padlock probe, and wherein the circularised padlock probe is amplified by rolling circle amplification (RCA) to produce a rolling circle product (RCP), the RCP containing multiple complementary copies of the nucleotide barcode sequence, characterised in that the method comprises:

(a) assigning a unique signal code sequence to the target nucleic acid molecule, wherein the signal code sequence is specific to that molecule;

(b) providing the padlock probe with a nucleotide barcode sequence such that a RCP is formed comprising multiple complementary copies of the nucleotide barcode sequence that each corresponds to the signal code sequence, wherein the signal code sequence may be derived by interrogating the complementary copies of the nucleotide barcode sequence with sequential detection probes each yielding a signal and the signals together make up the signal code sequence;

(c) contacting the RCP with a first detection probe for generating a signal code for the first position of the signal code sequence and allowing the detection probe to hybridise to the RCP at the complementary copies of the nucleotide barcode sequence, wherein the detection probe comprises a recognition sequence complementary to the nucleotide barcode sequence and a reporter;

(d) detecting a signal from the reporter of the first detection probe which has hybridized to the RCP;

(e) identifying the first signal code for the first position in the signal code sequence for the RCP from the signal detected in (d);

(f) removing the first detection probe from the RCP;

(g) contacting the RCP with a subsequent detection probe for generating a signal code for the next position of the signal code sequence, and allowing the detection probe to hybridise to the nucleic acid molecule at the complementary copies of the nucleotide barcode sequence, wherein the detection probe comprises a recognition sequence complementary to the nucleotide barcode sequence and a reporter;

(h) detecting a signal from the reporter of the subsequent detection probe which has hybridized to the RCP;

(i) identifying the signal code for the next position in the signal code sequence for the RCP from the signal detected in (g);

(j) removing the subsequent detection probe from the RCP;

(k) repeating steps (g)-(j) to identify signal codes for subsequent signal code positions until sufficient signal codes have been identified to identify the nucleotide barcode sequence and thereby to detect the nucleic acid molecule.

All of the disclosures provided above, for example, those in relation to detection probes, reporters, the detection of signals, and the identification of signal codes etc., may be applied to this method of detecting a target nucleic acid molecule. In particular, the removal of the detection probes, i.e. steps (f) and (i) may be effected by any suitable means disclosed herein or known in the art (Xiao and Guo, 2018, Front Cell Dev Biol, 6-42; Peng, 2017, Sequential Color Display for Highly Multiplexed in situ Single-Molecule Detection, Dissertation for Doctor of Philosophy, Stanford University; Duose et al, 2012, Nucleic Acids Research, 3289-3298). Such means may include the use of formamide buffers, or displacement probes, or simply equilibrium kinetics wherein unbound preceding detection probes are washed away and a subsequent detection probe is added in excess, and may displace a preceding bound probe.

The method may be for detecting multiple different nucleic acid molecules present in a sample, wherein each different nucleic acid molecule is assigned a different signal code sequence and is detected using a specific padlock probe with a different nucleotide barcode sequence. In some embodiments, a different set of subsequent detection probes is provided for each different nucleic acid molecule, each different set of detection probes yielding a different signal code sequence.

In some embodiments, the target nucleic acid molecule is detected in situ in a tissue sample.

Further details regarding this method are provided in Example 3 and FIGS. 10 to 13.

The invention will now be described in more detail in the following non-limiting Examples. In addition, a set of drawings is presented in which:

FIG. 1 shows in (A) a schematic representation of a discontinuous barcode sequence, wherein each barcode position comprises a barcode subunit flanked by spacer sequences, and wherein one spacer of a barcode position overlaps the spacer of an adjacent barcode position; and in (B) a schematic representation of an alternative, continuous barcode design wherein each barcode position comprise two barcode subunits, and one subunit of the pair overlaps (i.e. is common with) a barcode subunit of an adjacent barcode position. The barcode positions depicted are numbered 1-5.

FIG. 2 shows detection probes designed to hybridise to the sequential barcode positions of a two distinct continuous nucleotide barcode sequences of the format depicted in FIG. 1(B). The subunits of the barcode positions are indicated by the letters A to G beneath the barcodes. Y, G, B and R respectively indicate the colours yellow, green, blue and red depicted as the colorimetric detectable labels of the detection probes.

FIG. 3 shows (A) the design of a discontinuous barcode sequence of the format depicted in FIG. 1 (A), showing barcode subunits (BC1-BC4) each flanked by spacer sequences. (B) shows direct detection probes, directly provided with colorimetric labels; (C) shows indirect detection probes in the form of L-probes with one overhang for binding a reporter probe provided with a colorimetric label; and (D) shows indirect detection probes in the form of U-probes with 2 overhangs, one of which is depicted to bind the labelled reporter probes. The probes in (D) have an asymmetric design wherein the second flanking region is shorter than the first.

Figure 1:
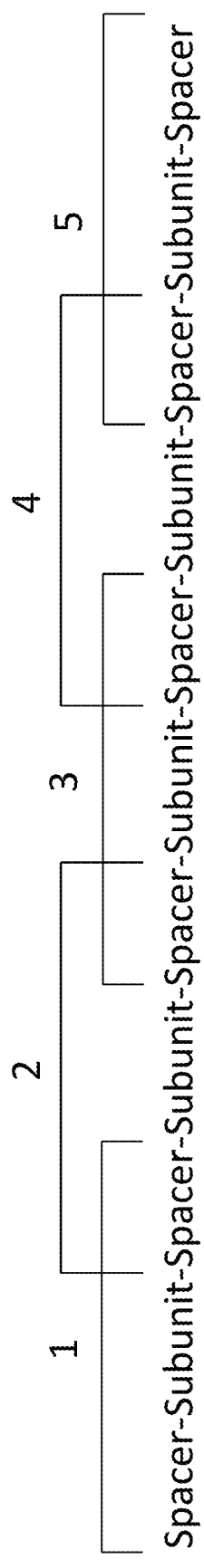
Figure 1:
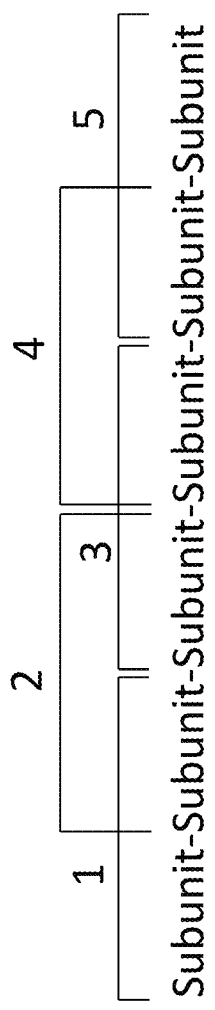
Figure 2:
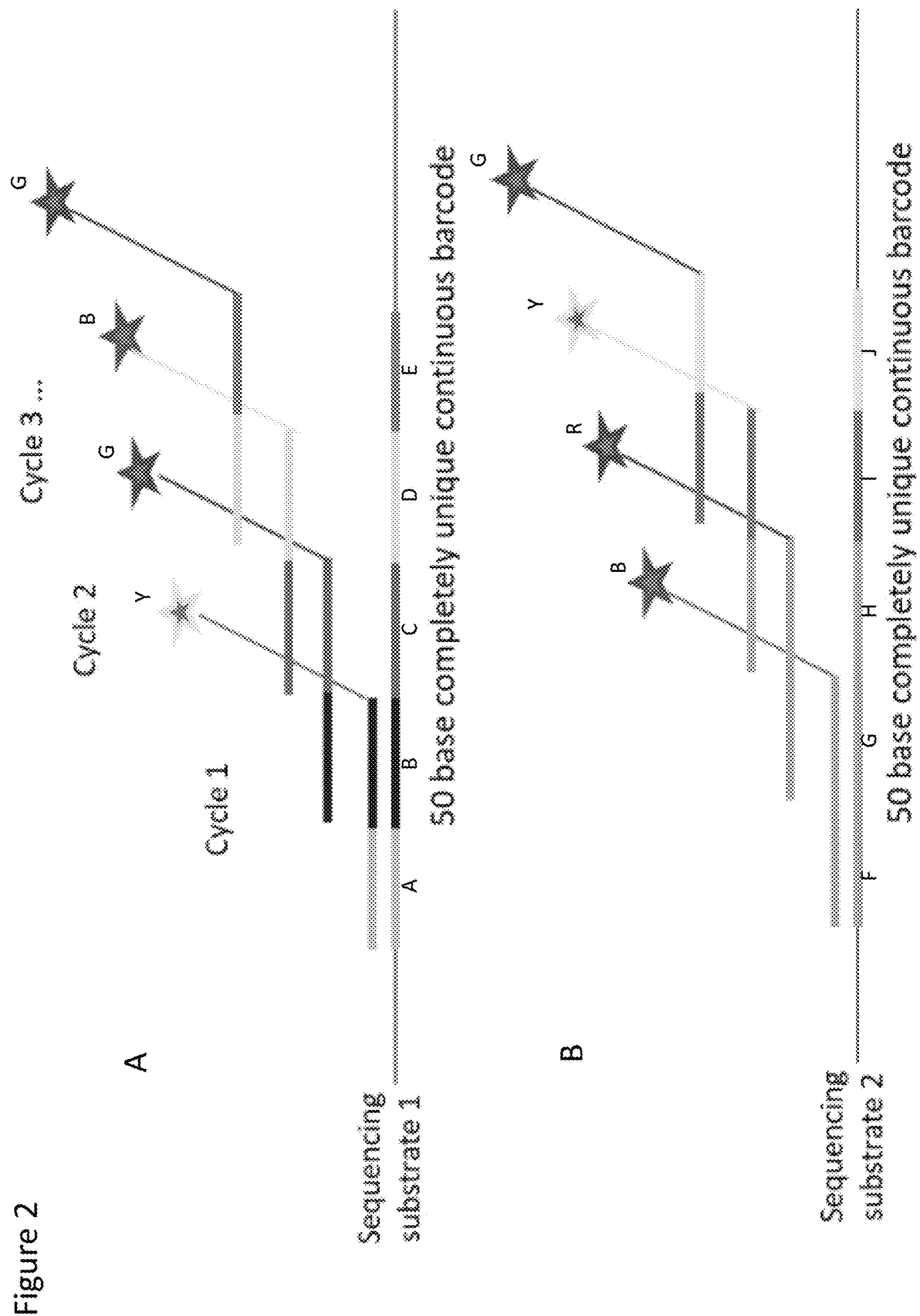
Figure 3:
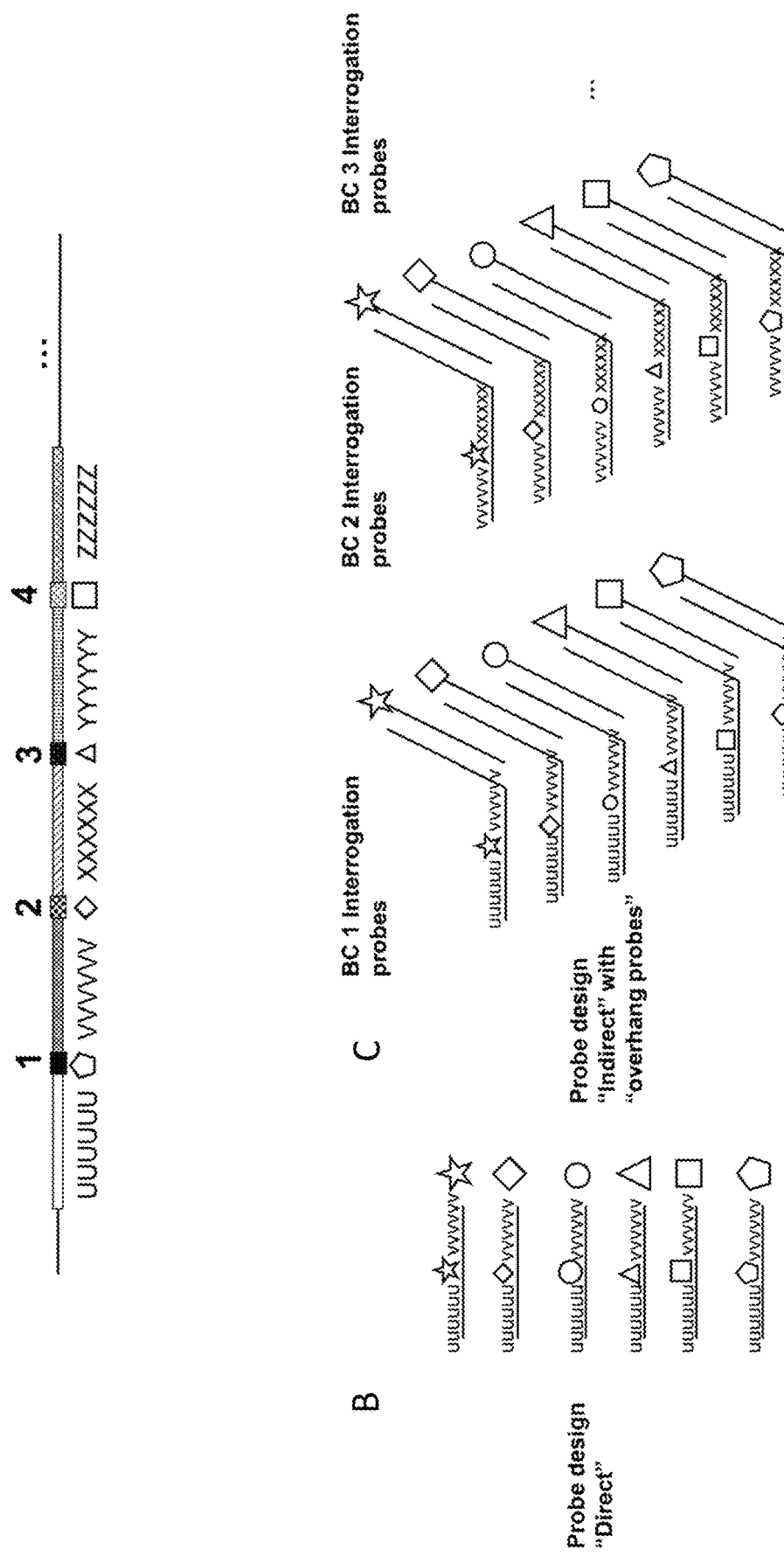
Figure 3:
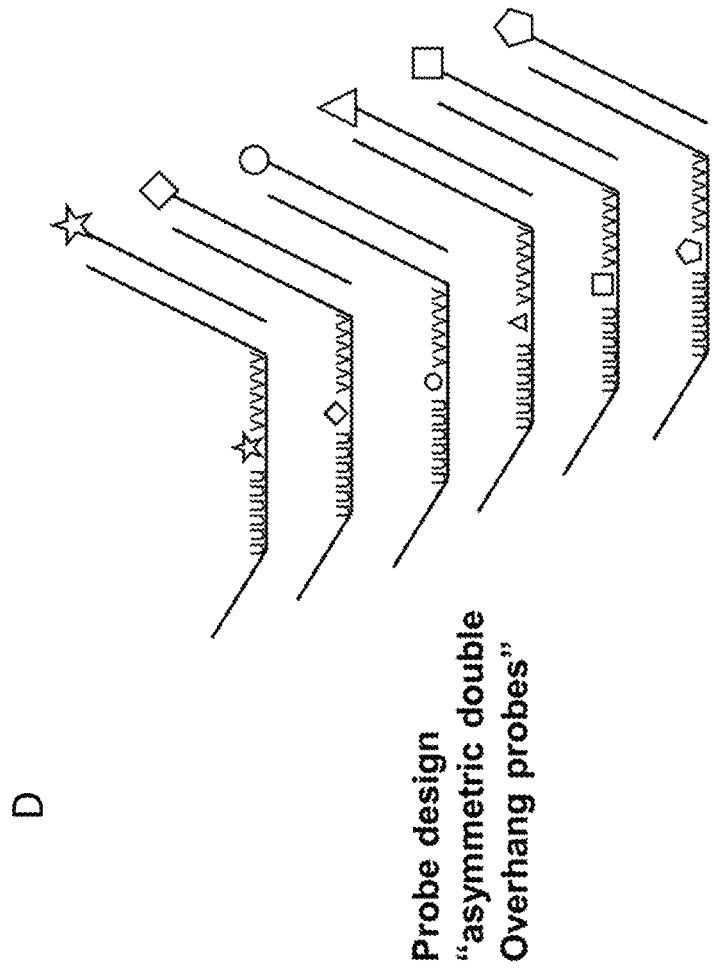
Figure 4:
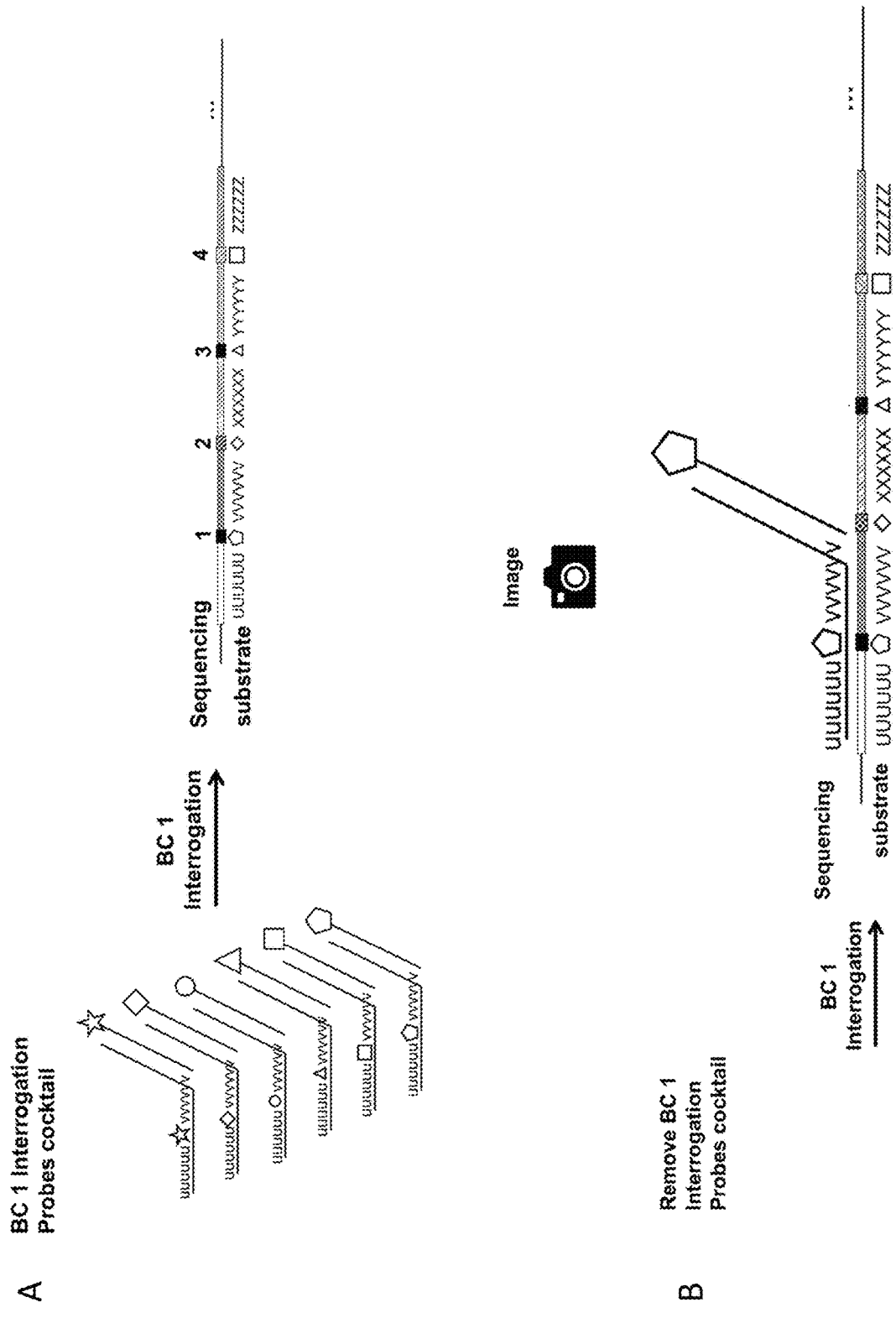
FIG. 4 shows a reaction scheme for interrogation of the discontinuous barcode sequence of FIG. 3, using detection probes as depicted in FIG. 3 (B).
Figure 4:
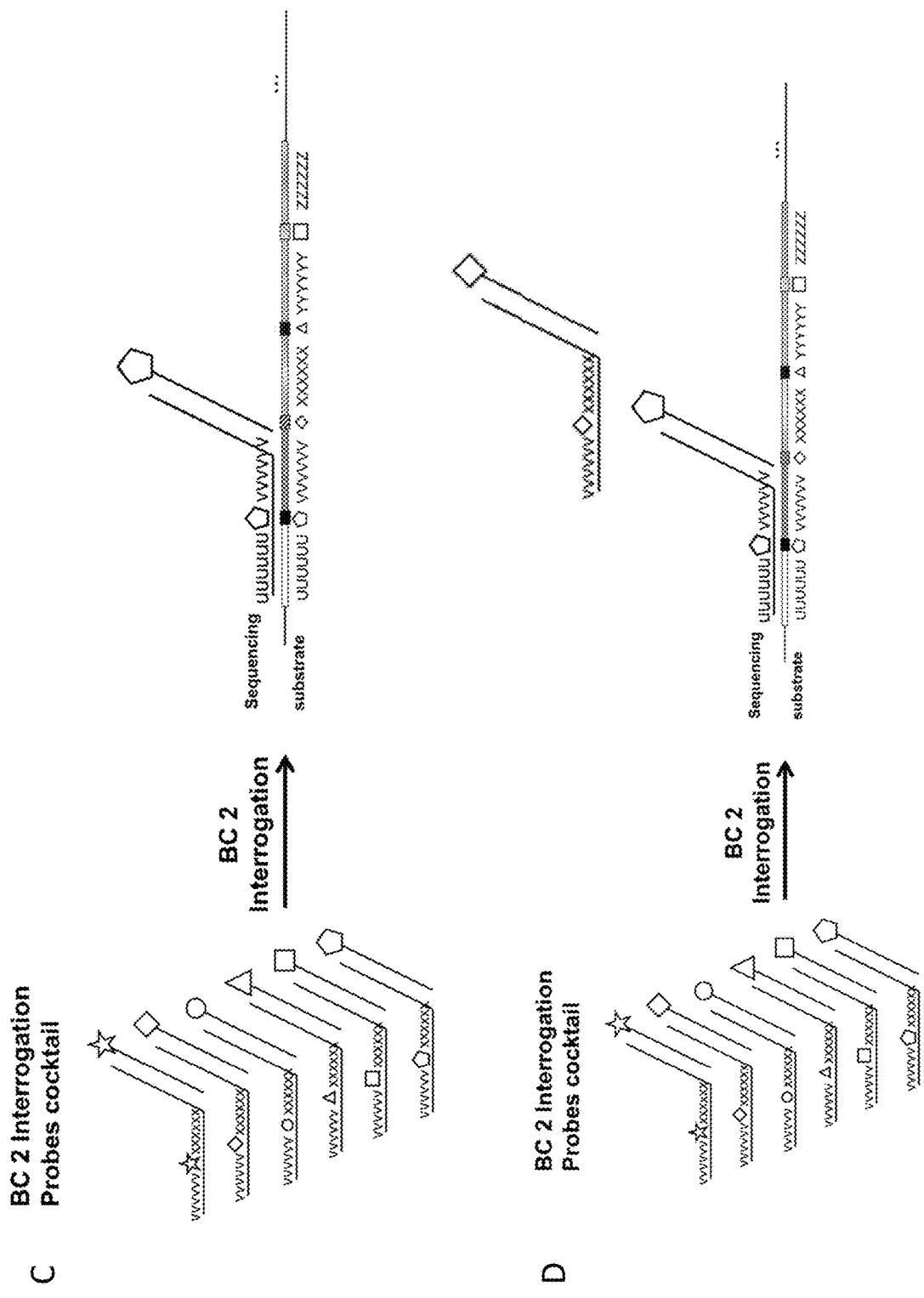
Figure 4:
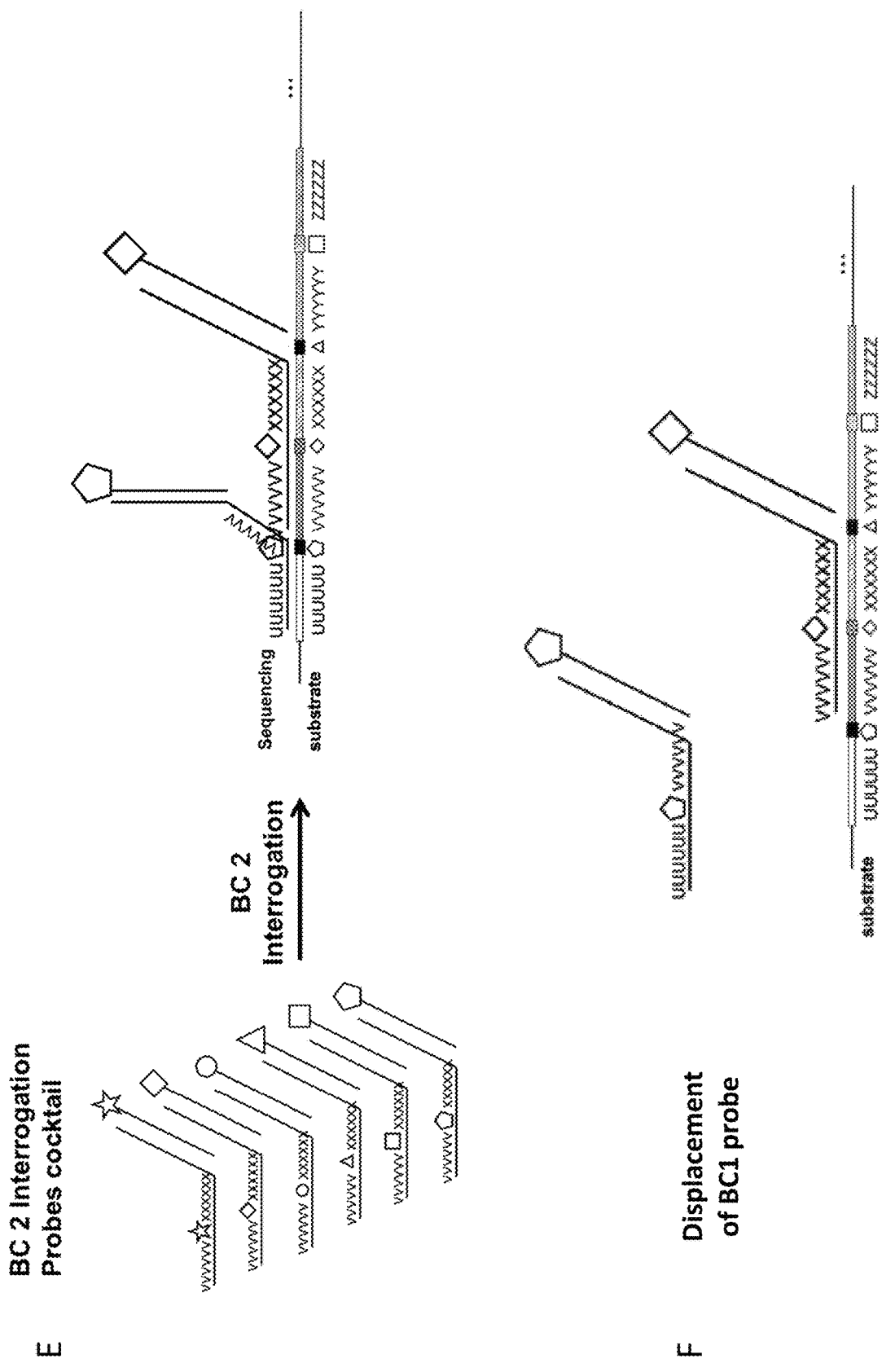
Figure 4:
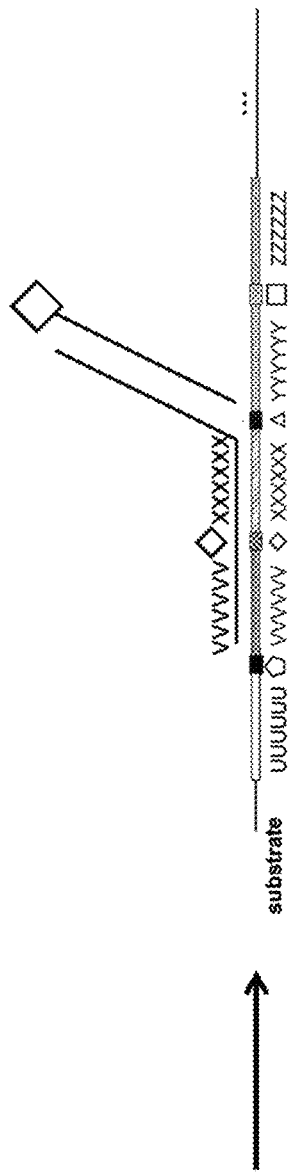
Figure 5:
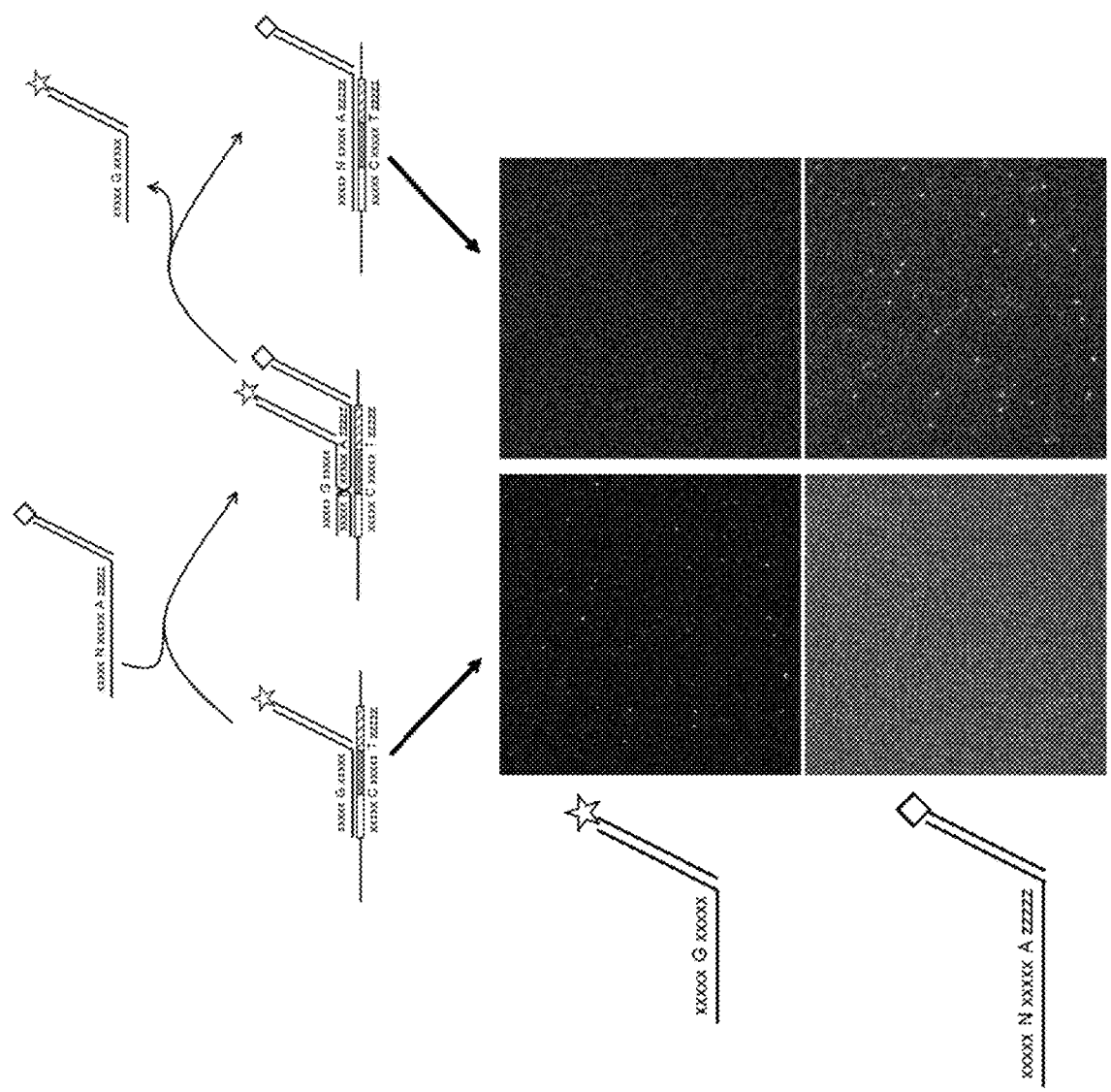
FIG. 5 shows an alternative detection probe design for a discontinuous barcode sequence of the format of FIG. 1(A) wherein a subsequent detection probe has an extended first flanking sequence, which extends into the barcode position and first spacer sequence of the preceding barcode position.
Figure 6:
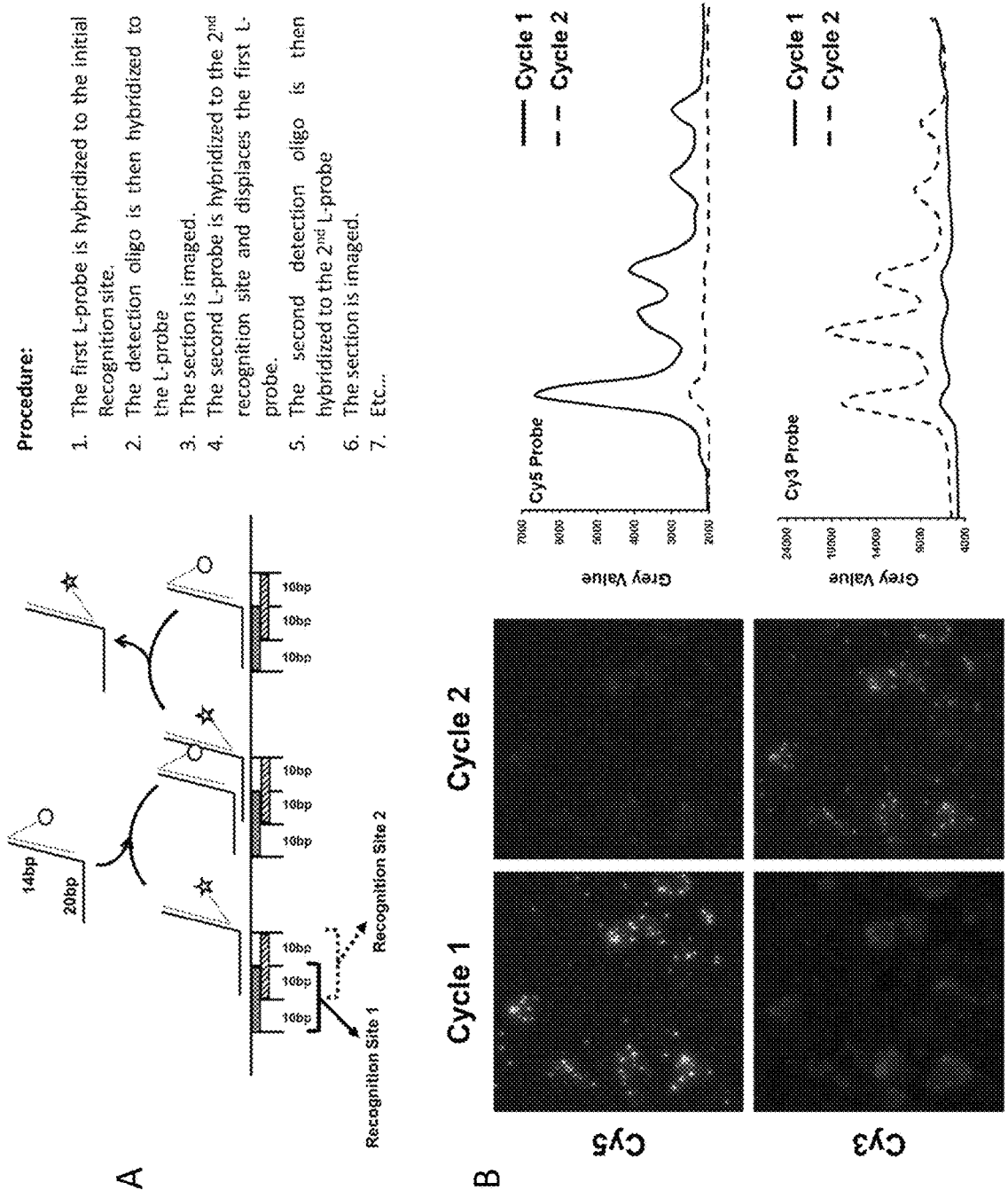

FIG. 6 schematically depicts in (A) the operation of a method for decoding a continuous barcode sequence of the format shown in FIG. 1(B). In (B) the results of such a method performed in Example 2 are presented, showing fluorescent microscopy images of detection probes hybridised to a RCP target.

Figure 7:
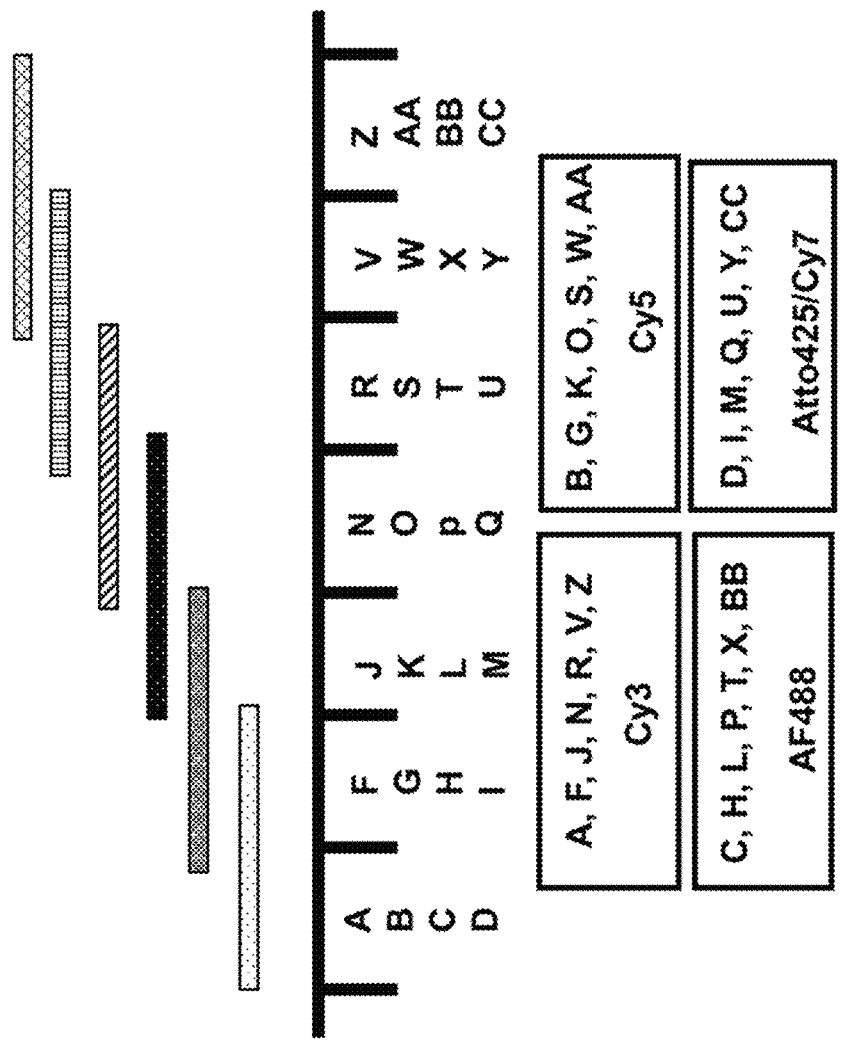

FIG. 7 schematically depicts a decoding scheme for decoding a continuous barcode sequence of the format shown in FIG. 1(B).

Figure 8:
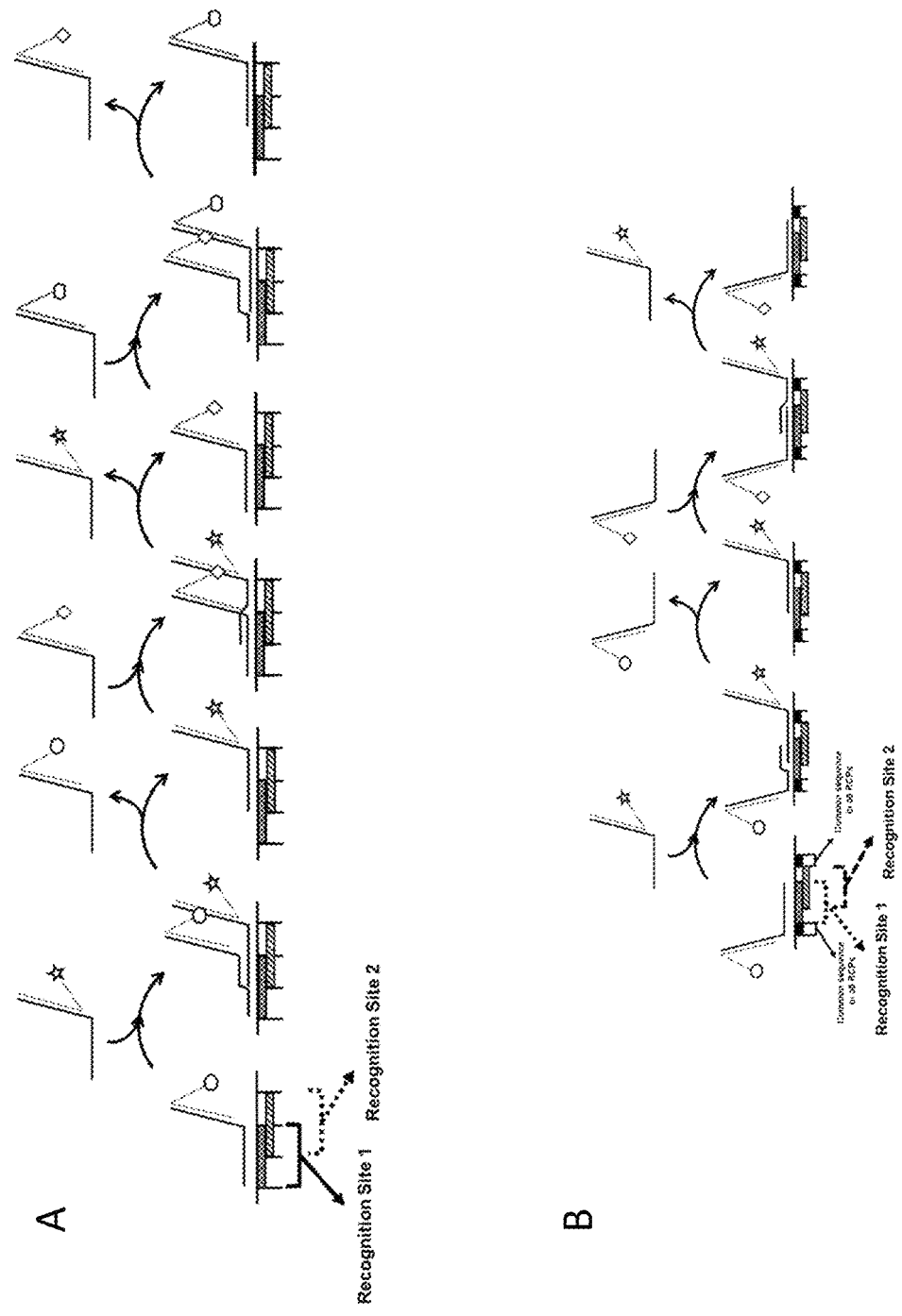

FIG. 8 shows in (A) and (B) two alternative methods which involve reading the same two barcode positions back and forth using different detection probes in sequence, which displace each other in alternating forward and reverse directions, to generate the signal code sequence.

Figure 9:
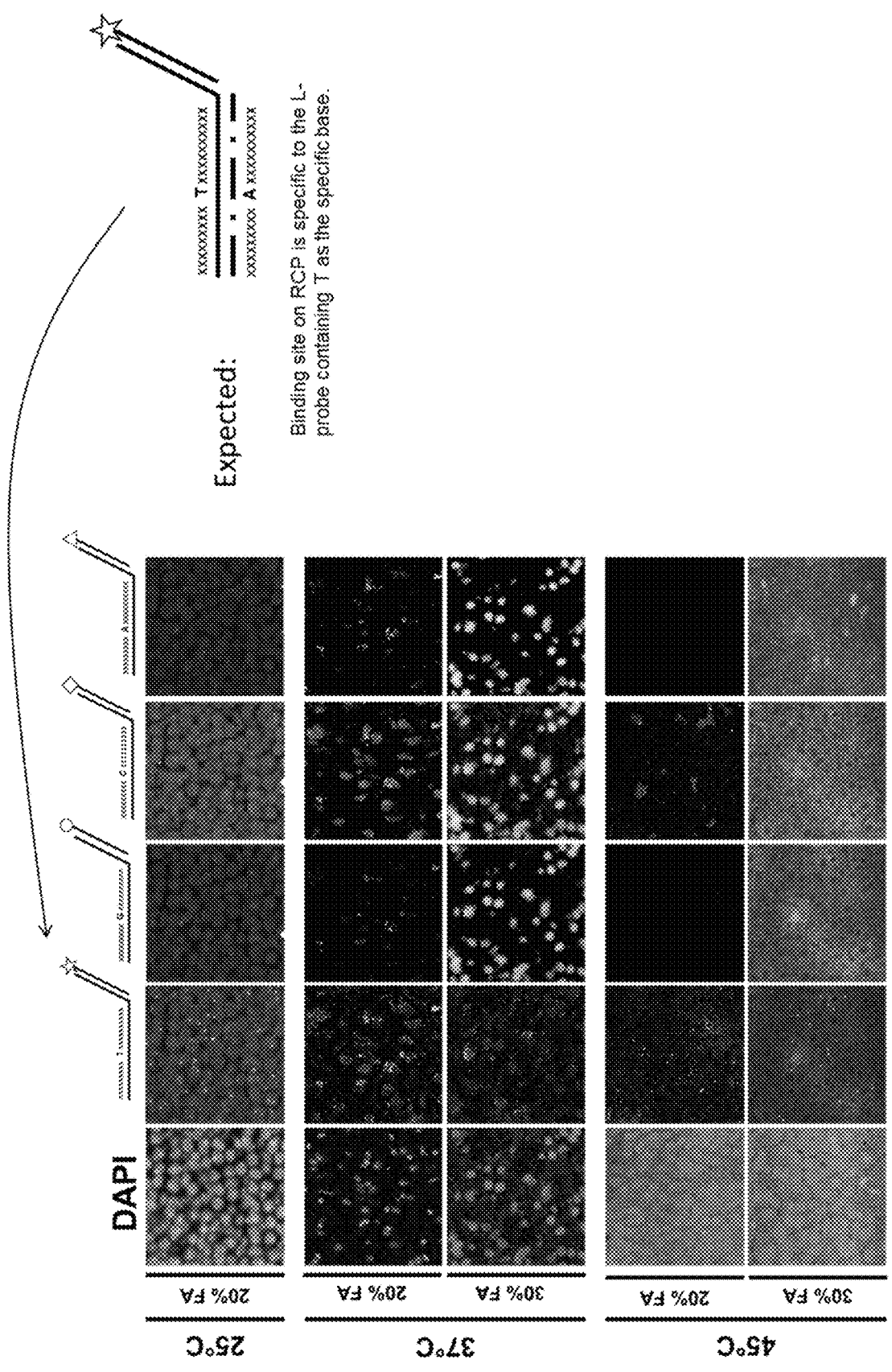

FIG. 9 shows fluorescent microscopy images obtained following the hybridisation of a set of detection probes to an RCP under various conditions. As shown, each detection probe comprises a different nucleotide at the position corresponding to the barcode subunit, and a different reporter. % FA indicates formamide concentration.

Figure 10:
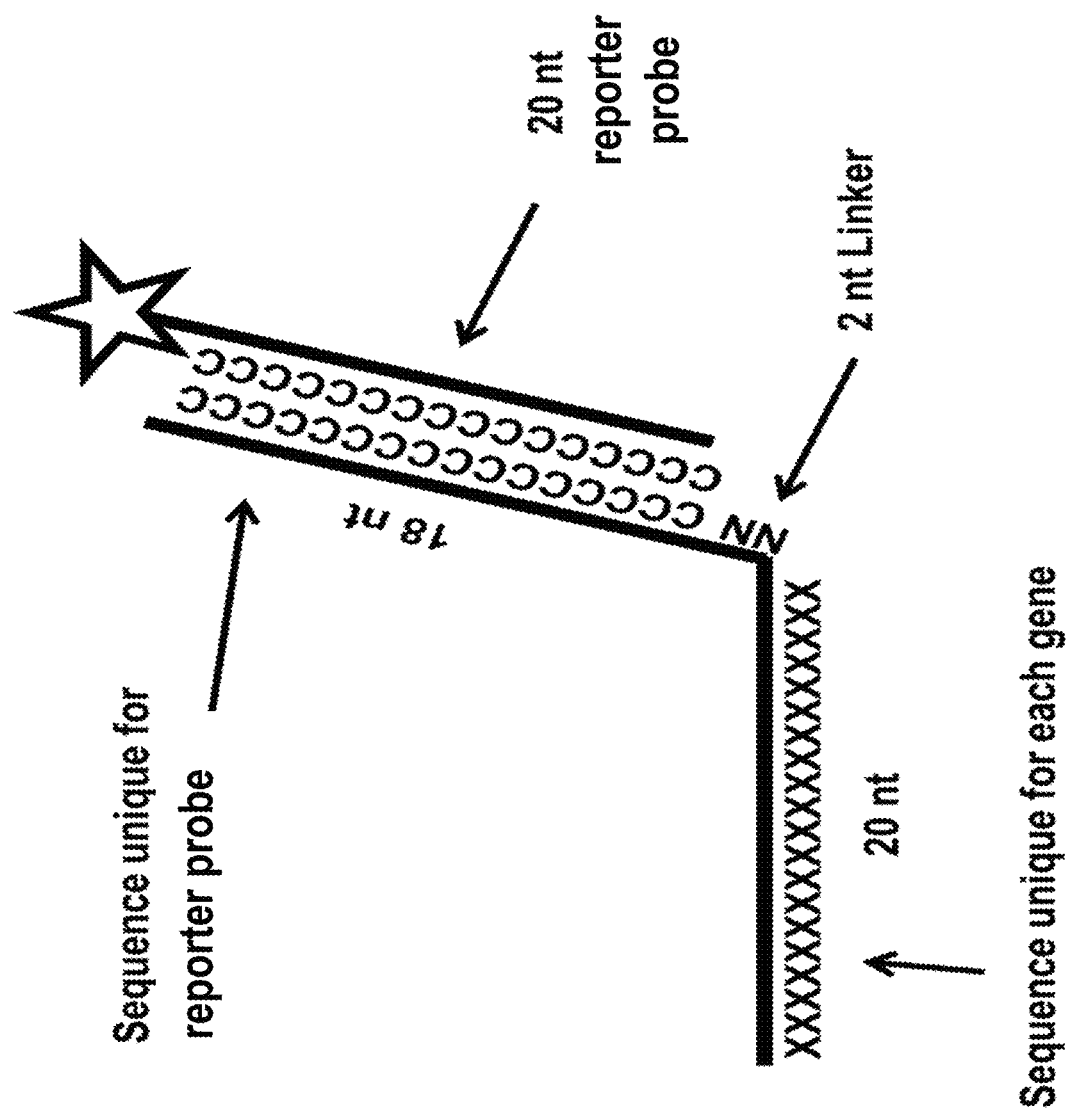

FIG. 10 shows the design of an L-shaped detection probe (L-probe) suitable for detecting a target nucleic acid molecule comprising a sequence unique for a gene to be detected, a linker, and a sequence unique for a reporter probe. A complementary reporter probe comprising a detectable label can then bind to the L-probe at the reporter probe binding region.

Figure 11:
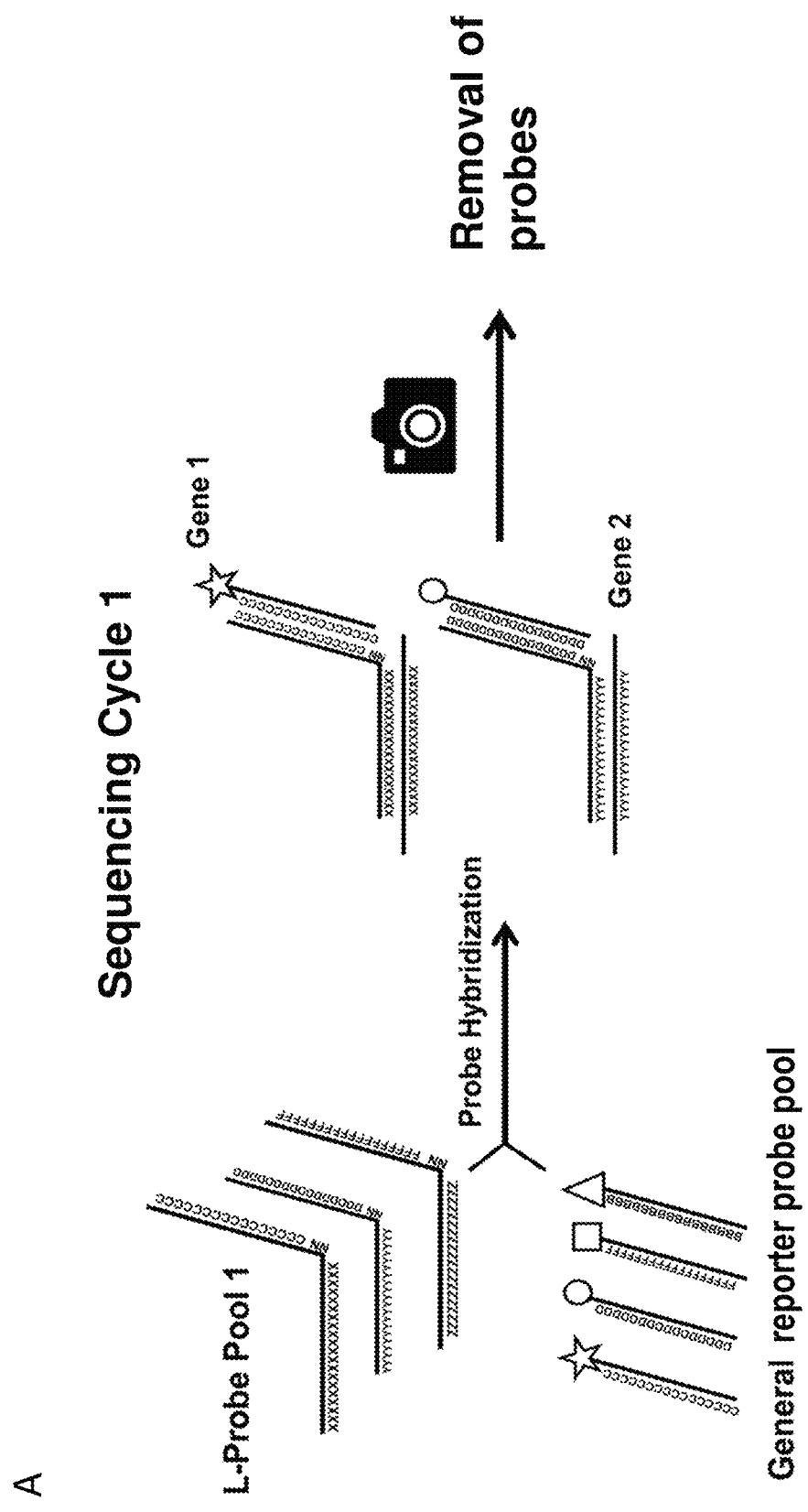
Figure 11B:
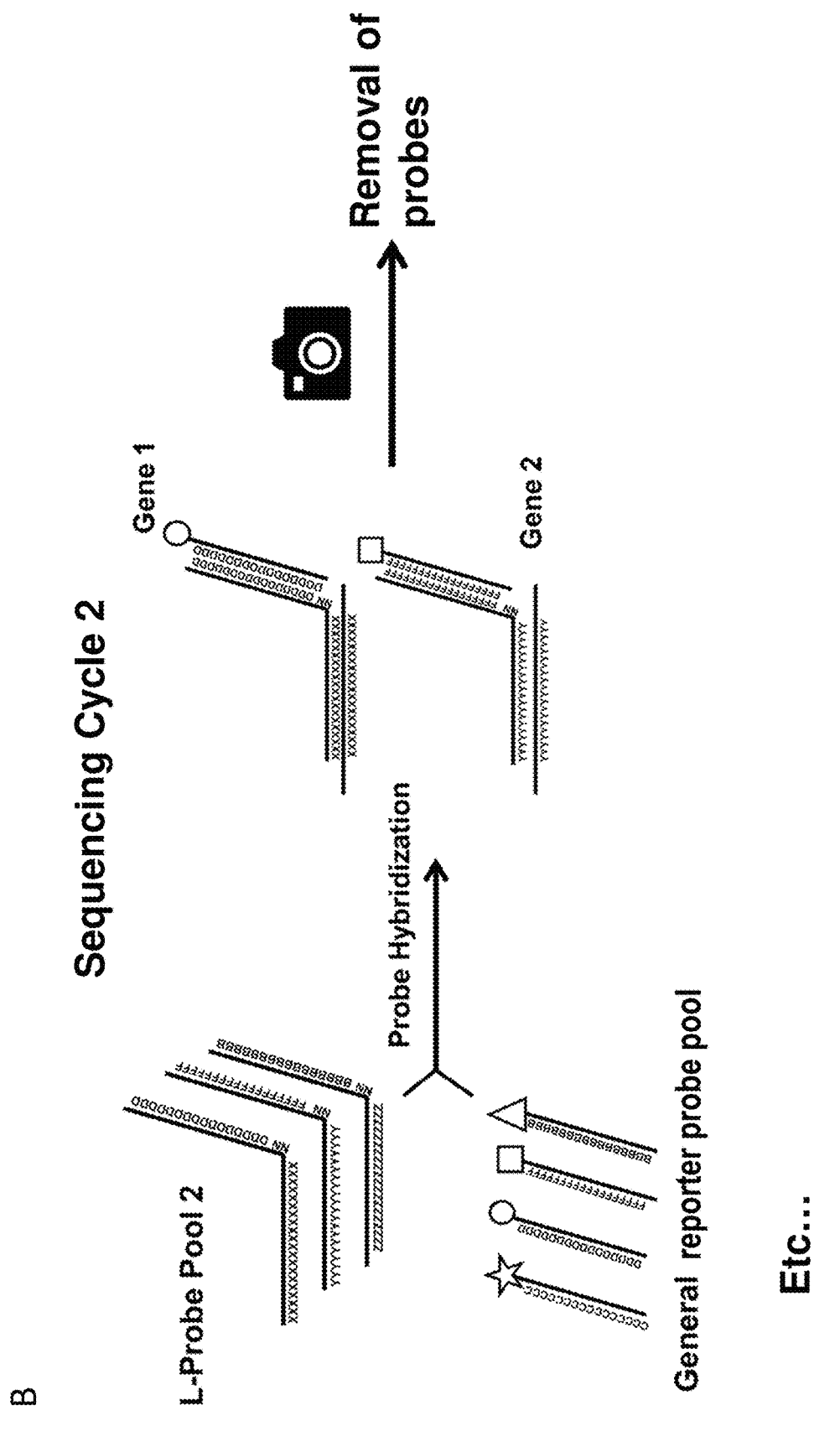

FIG. 11 shows in (A) and (B) the first 2 cycles of a reaction scheme designed to detect target nucleic acid molecules comprising genes 1 and 2. In each cycle, pools of L-shaped detection probes (L-probes) and reporter probes are hybridised (directly and indirectly, respectively) to the target nucleic acid molecules, before the probes are imaged and removed.

Figure 12:
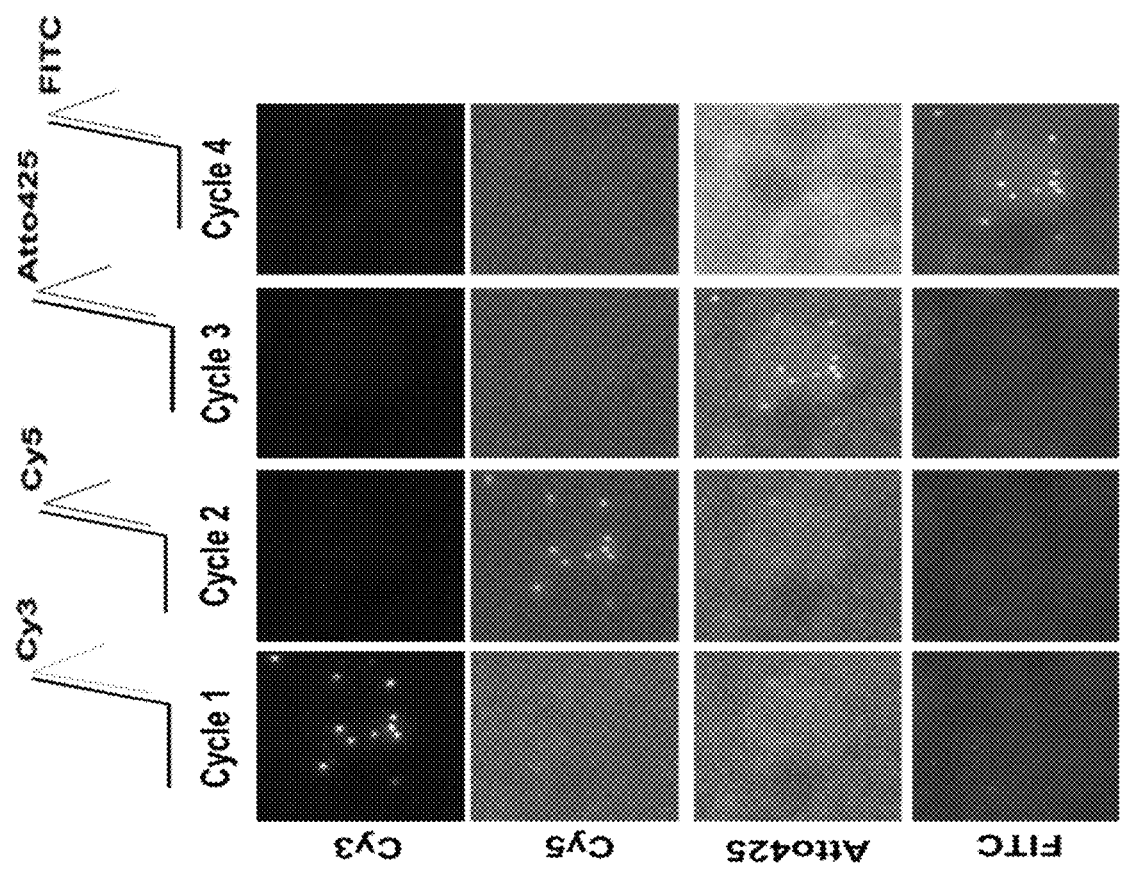

FIG. 12 shows the signals detected from 4 cycles of a reaction carried out according to the scheme in FIG. 11. In cycle 1, an L-probe with a sequence complementary to a Cy®3 (dye) reporter probe is hybridized to the target nucleic acid molecule, and a Cy®3 (dye) signal can be observed. These probes are then removed, and L-probe with a sequence complementary to a Cy®5 (dye) reporter probe is hybridized in cycle 2. A Cy®5 (dye) signal can then be observed. This process is repeated with Atto425 and FITC reporter probes in cycles 3 and 4, respectively.

Figure 13:
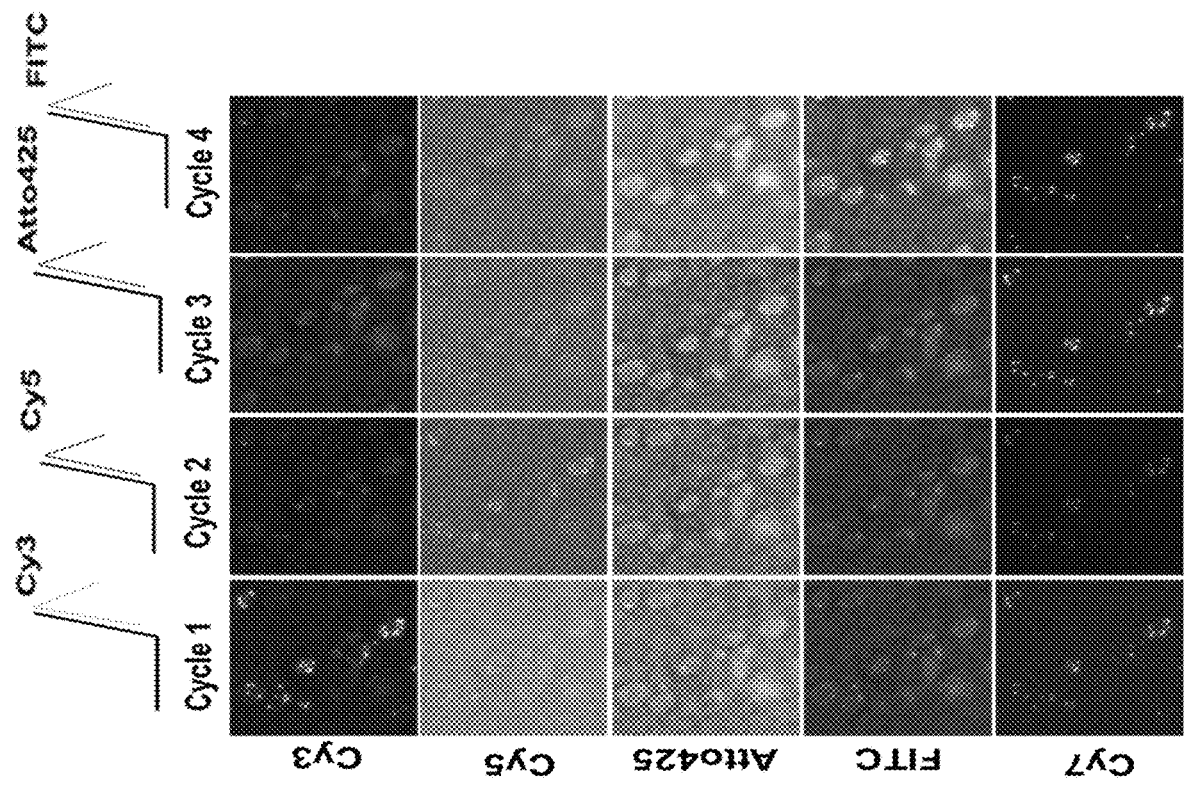

FIG. 13 shows the signals detected from 4 cycles of a reaction carried out according to the scheme in FIG. 11. The L-probes are hybridised in the same order as in FIG. 12. In this experiment, an "anchor probe", comprising a sequence complementary to a specific recognition site present in all RCPs, and a Cy®7 (dye) fluorophore was also used as a positive control. At each cycle, the anchor probe was hybridised to the RCPs in addition to the detection probes, imaged and removed.

Figure 14:
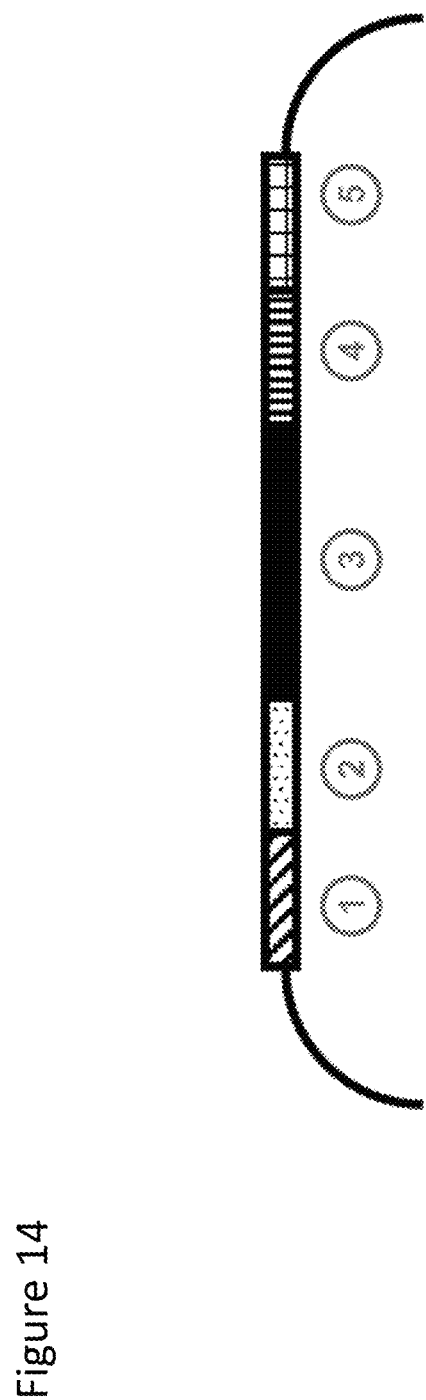

FIG. 14 shows a schematic of the design of the barcode sequence of a padlock probe to be used in the 2-LSD method. The various regions within this padlock are necessary to allow the 2-LSD mechanism and detection probes to properly bind and displace each other. (1) and (5) represent 5 bp regions which are different to each other but are common to all padlock probes (regardless of target). (2) and (4) represent 5 bp regions which are unique to each binding site in the barcode sequence of the padlock. (3) represents a 10 bp region which is common to both binding site 1 and binding site 2. This is necessary to facilitate one detection probe displacing the other detection probe through strand displacement. Binding site 1 is a 20 bp sequence made up of sequences (1), (2) and (3). Binding site 2 is a 20 bp sequence made up of sequences (3), (4) and (5).

Figure 15:
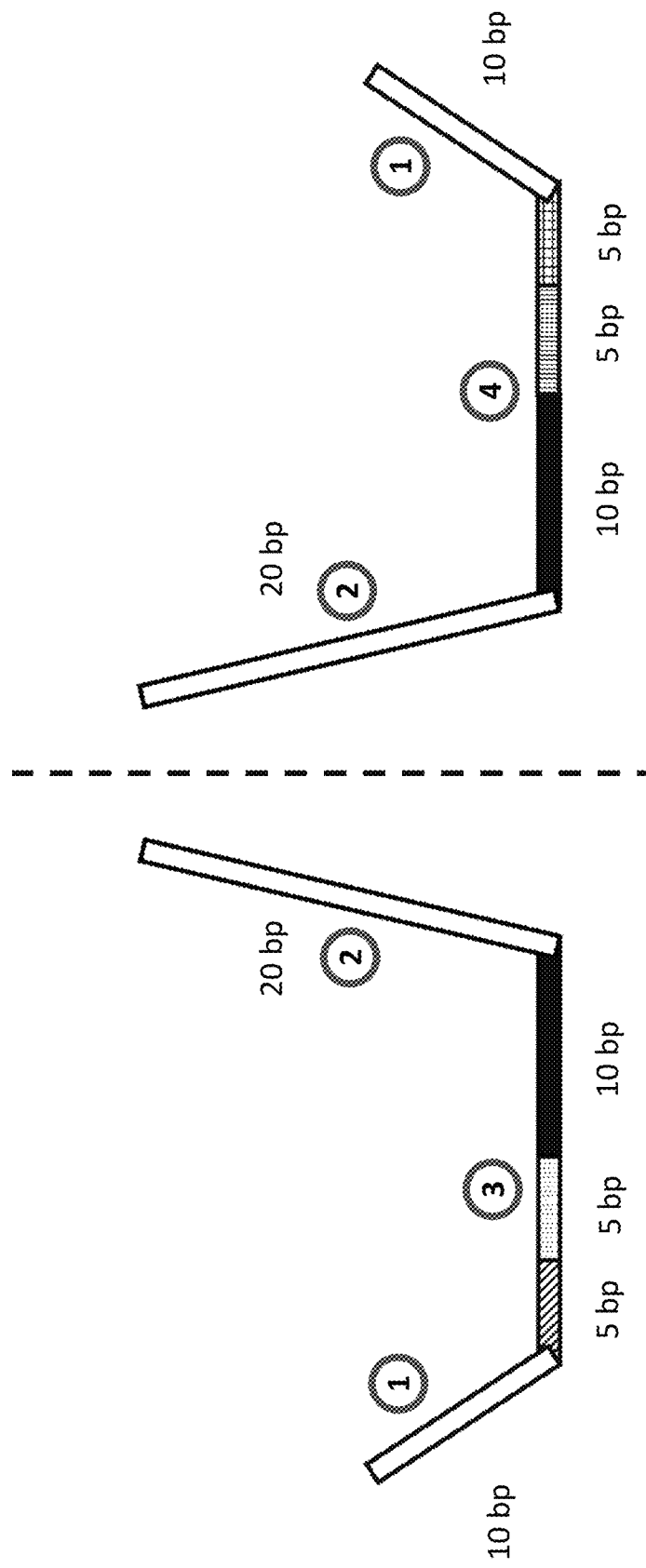

FIG. 15 shows the 2-LSD detection probe design. It outlines the main design features of the detection probe used in the 2-LSD method, including the toehold region. Left: detection probe that will bind to binding site 1, Right: detection probe that will bind to binding site 2. (1) represents the displacer toehold overhang, to which the displacer probe binds and initiates displacement. (2) represents the reporter probe binding site, to which the reporter probe binds in order to allow detection of the detection probe. (3) and (4) represent RCP binding regions, which are complementary to binding sites 1 and 2, respectively.

Figure 16:
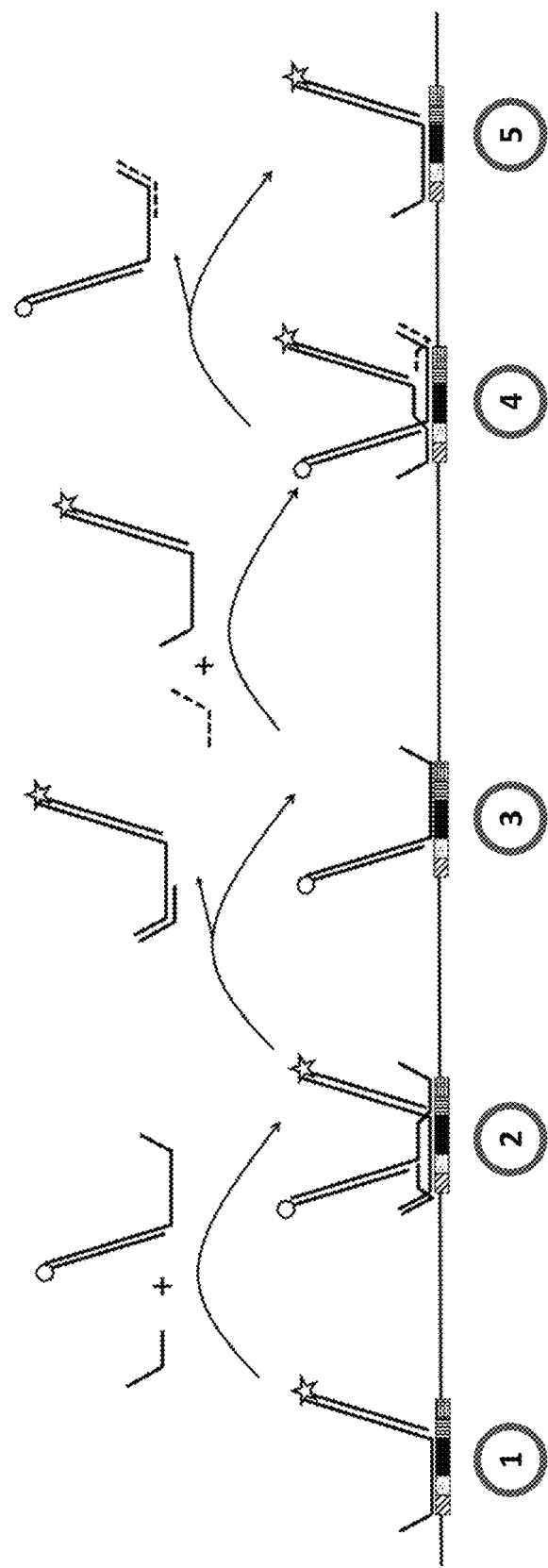

FIG. 16 shows a workflow for the 2-LSD method through three cycles of sequencing, including the "back-and-forth" approach with dual displacement. In (1), the first detection probe hybridises to binding site 1. In (2), the second detection probe is added, along with the first displacer probe. The second detection probe hybridises to binding site 2, and the first displacer probe hybridises to the displacer toehold overhang of the first detection probe. This initiates the displacement of the first detection probe. In (3), the first detection probe is fully displaced, leaving the second detection probe fully hybridised to binding site 2. In (4), a third detection probe is added, along with the second displacer probe. The third detection probe hybridises to binding site 1, and the second displacer probe hybridises to the displacer toehold overhang of the second detection probe. This initiates the displacement of the second detection probe. In (5), the second detection probe is fully displaced, leaving the third detection probe fully hybridised to binding site 1.

Figure 17:
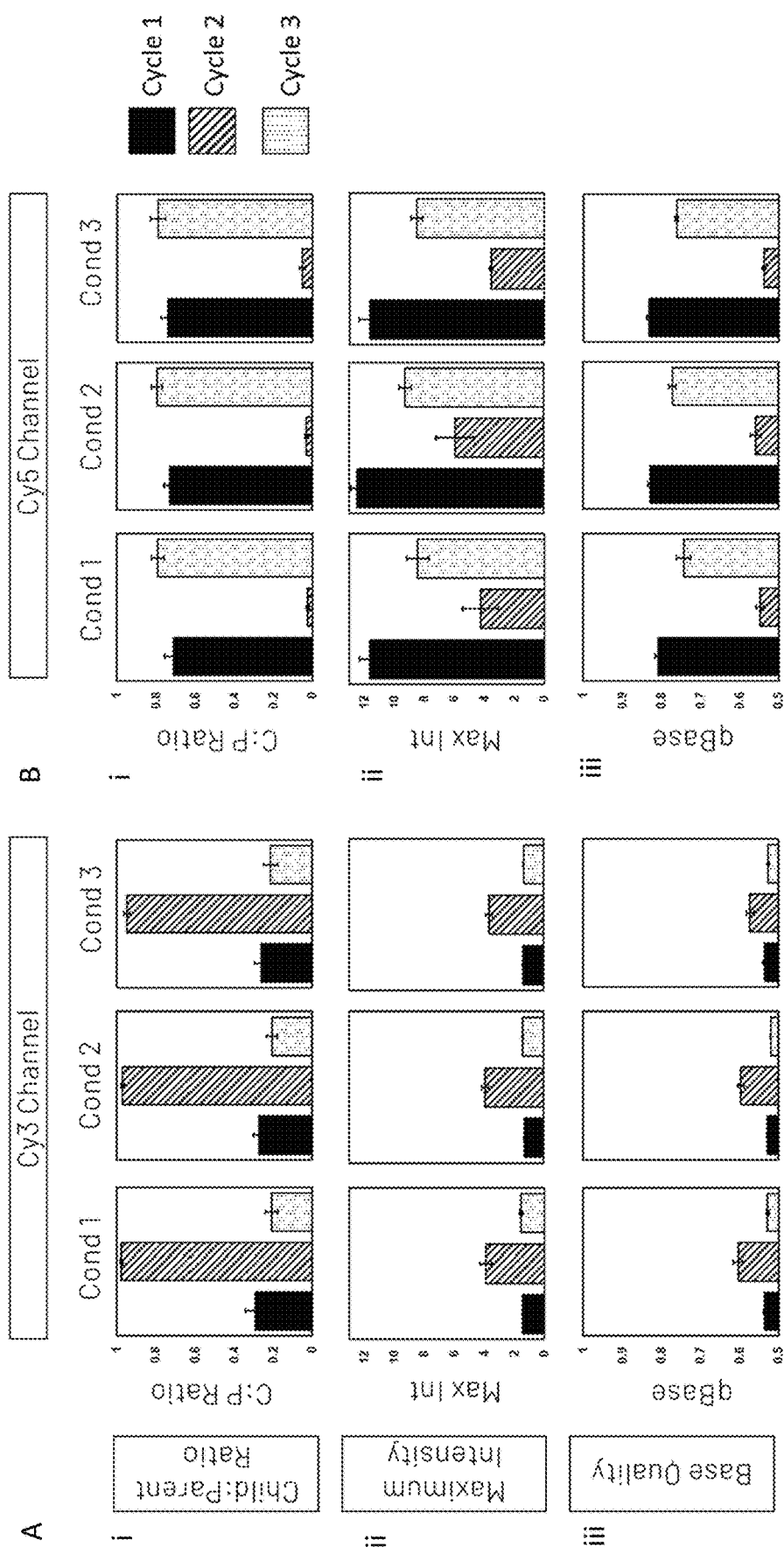

FIG. 17 shows the results of an experiment to optimise the displacement buffer. The 2-LSD method was applied to displace a Cy®5 (dye) detection probe with a Cy®3 (dye) detection probe, and subsequently to displace the Cy®3 (dye) detection probe with a Cy®5 (dye) detection probe, using 3 different displacement buffers. Both the Cy®3 (dye) (A) and Cy®5 (dye) (B) channels were detected. The child:parent ratio (A & B i), maximum intensity (A & B ii) and quality of the detected RCP signal (A & B iii) were quantified. These were used to determine the efficiency of detection probe displacement. N=5. The displacement buffer conditions were as follows: Cond 1: 5×SSC+0.05% Tween® (nonionic detergent)+20% Formamide; Cond 2: 2.5×SSC+ 0.05% Tween+20% Formamide; Cond 3: 2.5×SSC+20% Formamide.

Figure 18:
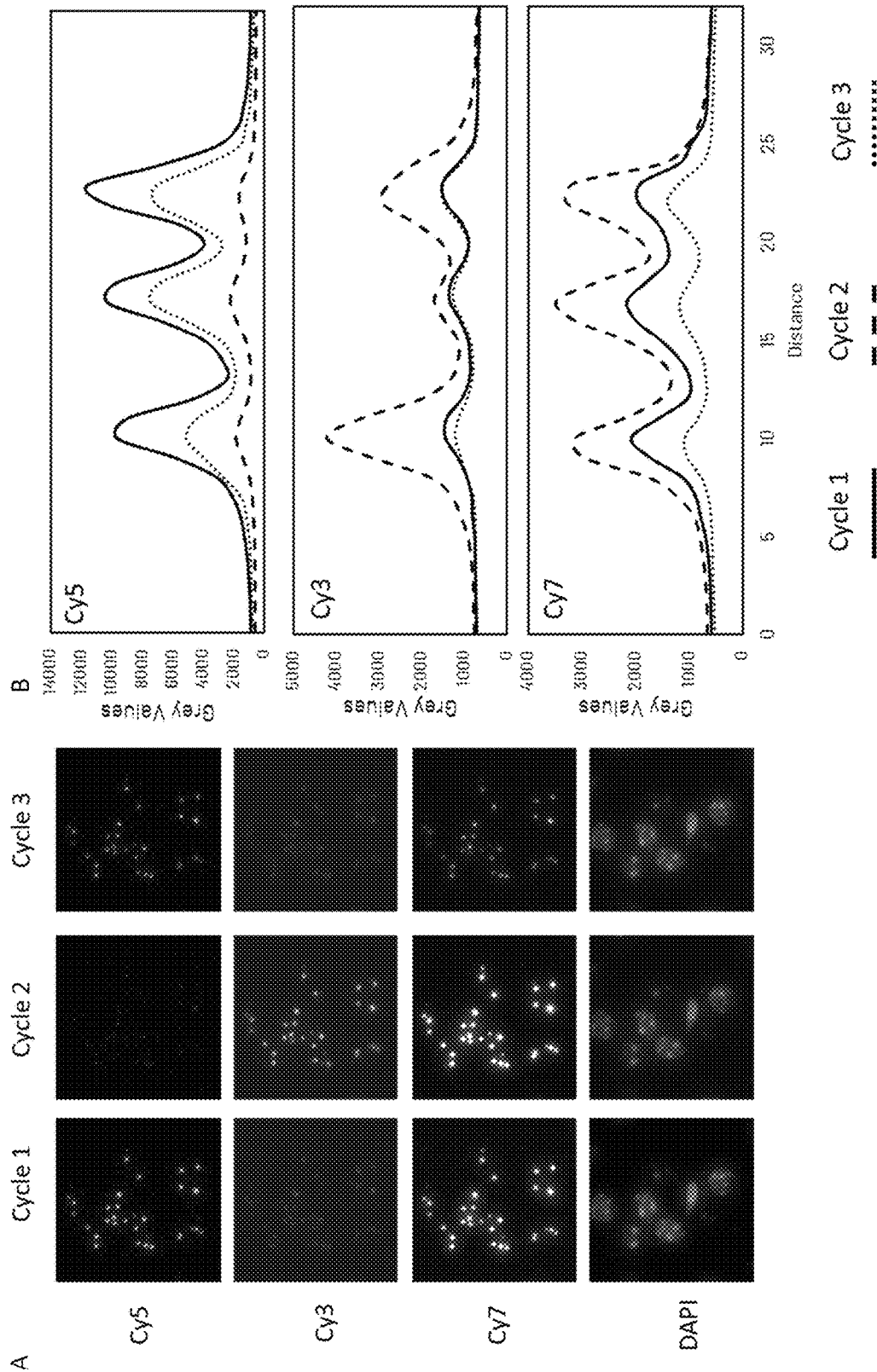

FIG. 18 shows the results of a 2-LSD experiment through 3 sequencing cycles. (A) shows microscope images of the Cy®5 (dye), Cy®3 (dye), Cy®7 (dye) and DAPI signals throughout the 3 cycles sequencing cycles. (B) shows line plots across 3 RCPs in the Cy®3 (dye), Cy®5 (dye) and Cy®7 (dye) channels, indicating the signal strength of those three RCPs in these channels through the 3 cycles.

EXAMPLES

Example 1—Sequencing by Hybridization to Detect a Discontinuous Barcode Sequence General Principle A first detection probe hybridizes to and decodes a first barcode subunit. A second detection probe then hybridizes in such a way that it displaces a part of the first detection probe. Each probe in the set of second probes used to interrogate the second barcode subunit comprises a common toehold region complementary to a sequence adjacent to the barcode subunit, to which it can hybridize very rapidly. The detection probe that is complementary to the second barcode subunit can then also hybridize to the overlapping part of the probe to which the first probe has bound and in this way can displace the first probe very efficiently. There is virtually no need for washing or formamide treatment which makes the method faster, cheaper and easier. The first probe, even though it still has the some affinity to the target is in minority (in much lower concentration) and hence, has a very little chance to hybridize and displace the second probe again and will eventually dissociate. The affinity of the second set of probes could even be increased by giving it one or two bases longer hybridization sequences in the toehold region.

The scheme works with barcode subunits that are individual bases (A, G, C and T) or duplets (AA, CC, GG, TT) or a mix of bases (AT, CG, TA, GC) or—preferably—triplets where at least two bases within the triplets are unique (two bases mismatch discrimination) to ensure high specificity.

Padlock probes can be provided with a barcode sequences with single base barcode subunits flanked by common spacer sequences in order to prove the principle. In this example a padlock probe against Actb was produced, with a single base difference in the middle of a common barcode sequence. RCA products were generated in vitro or in situ, inside fixed mouse brain tissue sections and were then interrogated with a set of probes targeting that single base barcode position. The barcodes were effectively decoded by a sequencing by hybridisation reaction using the detection probes.

Methods

RCA Generation In Vitro

Initial circular templates for rolling circle amplification were generated by performing a padlock probe ligation reaction templated by a single-stranded DNA template. The ligation of padlock probes was performed with a mix composed of 10 nM padlock probe (PO4-AGCCTCGCCTTTTGCCTTTTCTACGATTT-TACCAGTGGCTTTTGCGTCTATTTAGTGGAGC CtaacgctagaCTATCTTTCGCCCCGCGAGCACAG, SEQ ID NO: 1), 30 nM template (GGCAAAGGCGAGGCTCTGTGCTCGCGGGGC, SEQ ID NO: 2), T4 ligase reaction buffer (66 mM Tris-HCl (pH 7.5), 10 mM DTT, 10 mM $MgCl_2$), 0.2 µg/µl BSA, 0.68 mM ATP) and 1 U T4 ligase in a final volume of 50 µl. The mixture was incubated at 37° C. for 15 min followed by 65° C. for 2 min. Resulting circles from this reaction were diluted to 10 pM in mQ $H_2O$ and thereafter amplified by a target-primed RCA reaction, for which a mixture comprising 5 pM ligated circles, 0.2 µg/µl BSA, φ29 polymerase reaction buffer (Thermo Fisher), 125 µM dNTPs and 0.4 U/µl φ29 polymerase (Thermo Fisher) was used to amplify the abovementioned dilution of circles. The RCA reaction was incubated at 37° C. for 3 h and 65° C. for 2 min for heat inactivation.

10 µL of the resulting RCA reaction was then applied to positively charged microscope slides (Superfrost™, (coated glass slides) Thermo Fisher), covered with a 20×20 mm coverslip and incubated at room temperature for 15 min to allow RCA products to bind to the positively charged surface of the microscope slide. The coverslip was then removed, the slide washed in PBS twice and the RCA products were then subjected to sequencing by hybridization mix.

RCA Generation In Situ, Inside Fixated Mouse Brain Tissue Sections:

Mouse strain C57BL/6 at 30 days age (P30) was euthanized and the olfactory bulb was dissected via cryosectioning. Cryosectioning was performed on ThermoFisher cryostat, at 10 μm thickness. Sections were then adhered onto ThermoFisher Superfrost™ glass slides and stored at −70 C until processing.

Slides were first removed from −70° C. storage and left to thaw at room temperature (RT) for 5 min. Fixation step was conducted by incubating slides in 3.7% PFA in 1×DEPC-PBS (KI Substrat, MIK3125-1L) at RT for 5 min. The slides were then washed in 1×DEPC-PBS for 1 min to ensure PFA removal, before permeabilization in 0.1M HCl (KI Substrat, MIK-1282-500-1) in DEPC H2O for 5 min at RT. Following, the slides were then washed twice in 1×DEPC-PBS before dehydrating with ethanol series in 70% and 100% ethanol for 2 min each respectively. The slides were subsequently air dried at RT for 5 min before applying a Secure Seal™ chamber (Grace Bio-Labs) (adhesive enclosures) to each section. The sections were then rehydrated with 1×DEPC-PBS-T (KI Substrat, MIK1437-1L). To perform sample preparation the Cartana Neurokit was used (Cartana, Sweden). For reverse transcription 43.75 ul of Reaction Mix 1 (RM1), 1.25 ul of Enzyme 1 and 5.00 ul of Enzyme 2 were mixed together and added to each tissue section in a SecureSeal™ chamber (adhesive enclosure) mounted on top of the tissue slides. Samples were incubated overnight at 37 C. RM1 was then removed from the SecureSeal™ chambers (adhesive enclosures) and a post fixation solution containing 3.7% PFA in 1×DEPC-PBS was added to the samples and incubated at room temperature for 30 min. After post fixation, the samples were washed twice in 1×DEPC-PBS-T. For probe ligation, 36.0 ul of Reaction Mix 2 (RM2), 4.0 ul of Enzyme 3, 5.0 ul of Enzyme 4 and 100 nM of the Padlock probe (SEQ ID 1) were mixed and added into each SecureSeal™ chambers (adhesive enclosures) and incubated at 37 C for 30 min followed by at 45 C for 60 min. RM2 was then removed and samples were washed twice with 1×DEPC-PBS-T, after which the samples were ready for the in situ sequencing by hybridization reaction.

In Situ Sequencing by Hybridization of RCPs Immobilized on Glass Slides or in Tissue Sections In order to interrogate the first barcode subunit of the probe 100 μl of a SBH mix containing 2×SSC, 20% or 30% Formamide and SBH-oligonucleotide G (CACA TGCGTC-TATGTAGTGGAGCC TT AGAGAGTAGTACTTCCGACT, SEQ ID NO: 3), SBH-oligonucleotide A (CACA TGCGTCTATATAGTGGAGCC TT GTA GTA CAG CAG CAG CAT TGA GG, SEQ ID NO: 4), SBH-oligonucleotide T (CACA TGCGTCTATTTAGTG-GAGCC TT CAA TCT AGT ATC AGT GGC GCA, SEQ ID NO: 5), SBH-oligonucleotide C (CACA TGCGTC-TATCTAGTGGAGCC TT GGG CCT TAT TCC GGT GCT AT, SEQ ID NO: 6) and SBH-detection oligonucleotides Cy®3 (dye)—AGTCGGAAGTACTACTCTCT (SEQ ID NO: 7), Cy®5 (dye)—CCTCAATGCTGCTGCTGTAC-TAC (SEQ ID NO: 8), AF488 (Alexa Fluor® 488) (dye)—TGCGCCACTGATACTAGATTG (SEQ ID NO: 9), and TexR (Texas Red®) (dye)—ATAGCACCG-GAATAAGGCCC (SEQ ID NO: 10) was used. The SBH-oligonucleotides represent detection probes according to the present disclosure and invention. The detection oligonucleotides represent reporter probes as defined herein. The sequencing reaction was incubated for 30 min at 25° C., 37° C. or 45° C. The sequencing mix was then removed and the tissue sections were washed in PBS-T 0.05% twice. Subsequently, the tissue sections were mounted with mounting medium and a cover slip and imaged using 20× objective Zeiss microscope (Axio Z2).

Results

The first barcode subunit comprised A at the specific position that was being interrogated, and thus it was expected that the detection probe comprising T at the corresponding position would hybridise to the barcode subunit. The results are shown in FIG. 9. It can be seen that, at a range of temperatures and formamide concentrations, fluorescence is observed from the detection probe comprising T at the relevant position, and not from the other detection probes. It was therefore demonstrated that barcode subunits which differ by a single base can be interrogated and distinguished successfully using the present system. The methods are particularly effective at higher temperatures and formamide concentrations (i.e. 30% formamide and 37 or 45° C.).

Example 2—Linear Strand Displacement (LSD)

The LSD method represents the decoding of a continuous barcode sequence having sequential overlapping barcode positions, as described herein. The design of the LSD methods allows sequential toehold exchanges to be carried out in order to displace detection probes, thereby generating a decoding scheme that results in the identification of target nucleic acid molecules (e.g. genes in situ) without the need for stripping of detection probes (L-probes as used herein). In the main design, a detection probe in the form of an L-probe can hybridize to the target nucleic acid molecule, herein exemplified by an RCP, and a detection oligonucleotide (DO) (i.e. a reporter probe) is then allowed to hybridize and is subjected to imaging. The first detection L-probe consists of a reporter probe binding site, a unique toehold region (capable of hybridising to one barcode subunit of its target barcode position) and a common binding region (capable of hybridising to a second barcode subunit of the barcode position). The second detection L-probe that is designed to compete with the first detection L-probe also consists of a reporter probe binding site, a unique toehold region and a common region which it shares with the first L-probe (which hybridises to the overlapping barcode subunit, which is shared by the first and second barcode positions). The second L-probe will bind to the RCP via its unique toehold and compete with and displace the common binding site of the first L-probe. This results in the second L-probe fully occupying its RCP binding region and the first L-probe is left hybridized with just its unique toehold region. In order to complete the reaction, the unique toehold region of the first L-probe then spontaneously dissociates leaving the second L-probe (and its signal) as the only probe on the RCP. The unique toehold region of the second probe then becomes the common region it shares with the third L-probe and this will be used to set up another toehold exchange. This cycle can be continued for as many rounds as is necessary to decode the barcode.

The spontaneous displacement of the first probe during the toehold exchange can be driven forwards by the stringency of the hybridization buffer. The stringency of the hybridization buffer during the toehold exchange and the subsequent wash buffer are designed so that a 20 bp hybridization (i.e. the fully bound second detection probe) is less likely to dissociate compared to a 10 bp hybridization (i.e. the partially bound first detection probe). In addition, the local concentration of the first probes is reduced to a level which is much lower than the concentration of the second probe, making it therefore much less likely to reverse the toehold exchange.

Methods

Mouse Tissue Section Preparation

Mouse strain C57BL/6 at 30 days age (P30) was euthanized and the olfactory bulb was dissected via cryosectioning. Cryosectioning was performed on ThermoFisher cryostat, at 10 µm thickness. Sections were then adhered onto ThermoFisher Superfrost™ glass slides and stored at −70 C until processing.

RCA Generation In Situ

Fixation and Permeabilization

The tissue slide was removed from −70° C. storage and allowed to thaw for 5 min at room temperature (RT). Fixation was then performed by incubating the slides in 3.7% PFA in 1×DEPC-PBS at RT for 5 min. The slide was then washed in 1×DEPC-PBS for 1 min at RT. This ensures that the PFA is completely removed before moving to the permeabilization step. The tissue sections were then permeabilized using 0.1M HCl in DEPC-H2O for 1 min at RT and subsequently quickly washed twice in 1×DEPC-PBS. Following this, the slides were then dehydrated with an ethanol series in 70% and 100% ethanol for 2 min respectively before the slides are air-dried for 5 min at RT. A Secure Seal™ Chamber (Grace Bio Labs) (adhesive enclosures) are applied to each section and the sections are rehydrated with 1×DEPC-PBS-T before continuing with the reverse transcription step.

Reverse Transcription

Using CARTANA's Neurokit, 43.75 µl Reaction Mix (RM1), 1.25 µl of Enzyme 1 (RNase Inhibitor) and 5.00 µl of Enzyme 2 (Reverse Transcriptase) was added to each SecureSeal™ chamber (adhesive enclosure) and the samples were incubated in a humidity chamber at 37° C. overnight.

Probe Ligation

The reverse transcription was removed from the SecureSeal™ chambers (adhesive enclosures) and the slides were subjected to a post-fixation step using 3.7% PFA in DEPC-PBS for 30 min at RT. After the post-fixation step, the sections were quickly washed twice with DEPC-PBS-T. Using CARTANA's Neurokit, 36.0 µl Reaction Mix 2 (RM2), 4.0 µl of Enzyme 3 (RNase H), 5.0 µl of Enzyme 4 (Tth Ligase) and 100 nM of each padlock probe were added into each SecureSeal™ chamber (adhesive enclosure) and incubated at 37° C. for 30 min followed by a second incubation at 45° C. for 60 min. The ligation reaction mix was then removed from the SecureSeal™ chambers (adhesive enclosures) and the chambers were then washed twice with DEPC-PBS-T.

Rolling Circle Amplification

Using CARTANA's Neurokit, 43.0 µl of Reaction Mix 3 (RM3) and 5 µl of Enzyme 5 (φ29 Polymerase) was added to the SecureSeal™ chambers (adhesive enclosures) and incubated at either 37° C. for 3 hrs or at 30° C. overnight. This is followed by the removal of the amplification reaction mix washed twice with DEPC-PBS-T. The SecureSeal™ chambers (adhesive enclosures) were then removed and the slides were then dehydrated with an ethanol series in 70% and 100% ethanol for 2 min respectively before the slides were air-dried for 5 min at RT. The sections were then used for in situ sequencing using the LSD design.

In Situ Sequencing of RCPs in Tissue Sections Using the LSD Design

Probe Design

The L-probes designed to hybridize to the RCP and displace each other consist of 3 distinct parts. The first part is the arm where the detection probe binds. This is 14-20 bp long and encodes for a unique binding site specific to one detection probe, and hence colour. The second is a unique toehold region (7-10 bp) that allows the initial hybridization and a third part is a common binding sequence (7-10 bp) that is shared by the displacer probe (i.e. the subsequent detection L-probe).

Probe Hybridization

The sections are rehydrated with 2×SSC and the first probe mix was added at 100 nM in basic hybridization buffer (2.5×SSC+5-20% Formamide (depending on hybridization length)) and incubated at 1 hr at RT. The sections are the washed twice with basic washing buffer (2×SSC in DEPC-H2O).

Detection Oligonucleotide (Reporter Probe) Hybridization

After the L-probe hybridization, 100 nM detection oligo mix was added in basic hybridization buffer and allowed to hybridize for 30 min at RT. The sections were then washed twice with basic washing buffer before dehydrating the sections with an ethanol series in 70% and 100% ethanol for 2 min respectively, before the slides were air-dried for 5 min at RT. 10 µl SlowFade™ Gold antifade reagent (Invitrogen) was then added to each section and covered with a coverslip. The slide was subjected to microscope imaging.

Toehold Exchange After imaging, the coverslip was removed, and the slide was subjected to an ethanol series in 70% and 100% ethanol for 2 min respectively before air-drying the slide for 5 min at RT to remove the mounting media. The sections were then rehydrated with 2×SSC in DEPC-H2O. The second L-probe mix was then added at 200 nM in displacement hybridization buffer (2.5×SSC, 0.05% Tween®-20 (nonionic detergent) and 5-20% formamide conc. (depending on the hybridization length)). The sections were then incubated for 1 hr at RT and were subsequently washed with displacement wash buffer (1×DEPC-PBS-T and 10% formamide) twice for 10 min. After the toehold exchange, the sections were then subjected to detection oligo mix hybridization as described above.

Results

The proof-of-concept experiment was performed using a 20 bp hybridization length i.e. L-probes of 20 nucleotides in length, with a 10 bp unique toehold region and a 10 bp common region. FIG. 6A shows the displacement scheme that was utilized. This is a reverse toehold exchange where the L-probe specific to Recognition site 2 is added first and the toehold exchange is performed with the L-probe mix specific to Recognition Site 1. When the first probe mix, containing a probe encoding for the Cy®5 (dye) detection probe, is allowed to hybridize to the 2nd recognition site, we find a strong signal in the Cy®5 (dye) channel but no signal in the Cy®3 (dye) channel, indicating the presence of the correct L-probe on the recognition site (FIG. 6B). After the toehold exchange is performed, we find a dramatic decrease of the Cy®5 (dye) signal, indicating that the L-probe on Recognition Site 2 has been successfully removed from the RCP. This drop in Cy®5 (dye) signal coincides with an increase of the Cy®3 (dye) signal from background levels seen before the toehold exchange. This indicates that the Cy®5 (dye)-specific probe on the second recognition site is successfully exchanged for the Cy®3 (dye)-specific probe binding to Recognition site 1.

As outlined in the description above, the "LSD Design" relies on each hybridization domain of the L-probe to have a unique toehold region and one sequence in common with the probe that is next in the toehold exchange sequence. Due to the design (FIG. 6A) this toehold exchange can take place in both the forward and the reverse direction. The latter mechanism is demonstrated here, and the results are shown in FIG. 6B. From this figure, it can be seen that the signal from the 2nd recognition site is reduced to near background levels during the toehold exchange, which coincides with a sharp increase in the signal for the L-probe specific to the 1st recognition site. This shows that the toehold exchange was successful, though some signal for the 2nd recognition site does remain. The spontaneous removal of the L-probe is not 100% efficient. However, as the signal after the toehold exchange is sufficiently reduced to near background levels, the remaining signals can be filtered out by tweaking the detection threshold during image processing.

Compared to the discontinuous barcode sequence design, the LSD design utilizes a 7-10 bp unique toehold region and a 7-10 bp common region. This hybridization length has a high specificity so it is very unlikely that non-specific hybridization and toehold exchange will occur.

Due to these factors, the LSD design is efficient, specific, cheap and compatible with downstream processes as it does not damage the tissue morphology due to high formamide usage.

Example 3—In Situ Target Nucleic Acid Molecule Detection Using RCA and L-Shaped Detection Probes

Methods

Mouse Tissue Section Preparation

Mouse strain C57BL/6 at 30 days age (P30) was euthanized and the olfactory bulb was dissected via cryosectioning. Cryosectioning was performed on ThermoFisher cryostat, at 10 μm thickness. Sections were then adhered onto ThermoFisher Superfrost™ glass slides and stored at −70 C until processing.

RCA Generation In Situ

Fixation and Permeabilization

The tissue slide was removed from −70° C. storage and allowed to thaw for 5 min at room temperature (RT). Fixation was then performed by incubating the slides in 3.7% PFA in 1×DEPC-PBS at RT for 5 min. The slide was then washed in 1×DEPC-PBS for 1 min at RT. This ensures that the PFA is completely removed before moving to the permeabilization step. The tissue sections were then permeabilized using 0.1M HCl in DEPC-H$_2$O for 1 min at RT and subsequently quickly washed twice in 1×DEPC-PBS. Following this, the slides were then dehydrated with an ethanol series in 70% and 100% ethanol for 2 min respectively before the slides are air-dried for 5 min at RT. A Secure Seal™ Chamber (Grace Bio Labs) (adhesive enclosures) are applied to each section and the sections are rehydrated with 1×DEPC-PBS-T before continuing with the reverse transcription step.

Reverse Transcription

Using CARTANA's Neurokit, 43.75 μl Reaction Mix (RM1), 1.25 μl of Enzyme 1 (RNase Inhibitor) and 5.00 μl of Enzyme 2 (Reverse Transcriptase) was added to each SecureSeal™ chamber (adhesive enclosure) and the samples were incubated in a humidity chamber at 37° C. overnight.

Probe Ligation

The reverse transcription was removed from the SecureSeal™ chambers (adhesive enclosures) and the slides were subjected to a post-fixation step using 3.7% PFA in DEPC-PBS for 30 min at RT. After the post-fixation step, the sections were quickly washed twice with DEPC-PBS-T. Using CARTANA's Neurokit, 36.0 μl Reaction Mix 2 (RM2), 4.0 μl of Enzyme 3 (RNase H), 5.0 μl of Enzyme 4 (Tth Ligase) and 100 nM of each padlock probe were added into each SecureSeal™ chamber (adhesive chamber) and incubated at 37° C. for 30 min followed by a second incubation at 45° C. for 60 min. The ligation reaction mix was then removed from the SecureSeal™ chambers (adhesive enclosures) and the chambers were then washed twice with DEPC-PBS-T.

Rolling Circle Amplification

Using CARTANA's Neurokit, 43.0 μl of Reaction Mix 3 (RM3) and 5 μl of Enzyme 5 (φ29 Polymerase) is added to the SecureSeal™ chambers (adhesive enclosures) and incubated at either 37° C. for 3 hrs or at 30° C. overnight. This is followed by the removal of the amplification reaction mix washed twice with DEPC-PBS-T. The SecureSeal™ chambers (adhesive enclosures) are then removed and the slides were then dehydrated with an ethanol series in 70% and 100% ethanol for 2 min respectively before the slides are air-dried for 5 min at RT. The sections can then be used for in situ sequencing using the LSD design.

In Situ Sequencing of RCPs in Tissue Sections Using the L-Probe Design

Probe Design

The L-shaped detection probes (L-probes) designed to hybridize to the RCP probe binding site consists of 2 distinct parts. The first part is a 14-20nt long arm that recognizes the RCP. Each RCP is unique to a particular gene and hence this binding arm is specific for a specific gene. The second arm encodes for a reporter probe binding site. This sequence can differ depending on which reporter probe will bind. This arm consists of a 2nt linker and an 18nt reporter probe binding site.

Detection Probe Hybridization

The sections were rehydrated with 2×SSC and the first detection probe mix was added at 100 nM in basic hybridization buffer (2.5×SSC+20% Formamide) and incubated at 1 hr at 20-37° C. The sections are the washed twice with basic washing buffer (2×SSC in DEPC-H$_2$O).

Reporter Probe Hybridization

After the L-probe hybridization, 100 nM reporter probe mix was added in basic hybridization buffer and allowed to hybridize for 30 min at 20-37° C. The sections were then washed twice with basic washing buffer before dehydrating the sections with an ethanol series in 70% and 100% ethanol for 2 min respectively before the slides are air-dried for 5 min at RT. 10 μl SlowFade™ Gold antifade reagent (Invitrogen) is then added to each section and covered with a coverslip. The slide was subjected to microscope imaging. After imaging, the L-probes and the reporter probes are removed and a new sequencing cycle can commence.

Results

The proof of concept experiments were carried out using L-probes with 20 bp hybridization length, with a 20 bp RCP binding region. FIGS. 12 and 13 show the probe hybridization and removal and hybridization of a different L-probe mix through 4 cycles of sequencing. Cycle 1 in both figures show a strong Cy®3 (dye) signal in cycle 1 as the L-probe with a sequence complementary to a Cy®3 (dye) reporter probe is hybridized. After the removal of the Cy®3 (dye) complementary L-probe, the Cy®5 (dye) complementary L-probe was allowed to hybridize and a Cy®5 (dye) signal was seen in Cycle 2 with the Cy®3 (dye) signal completely or almost completely removed. This same was true for Cycle 3 with ATTO425 and Cycle 4 with AF488 (Alexa Fluor® 488) (dye). This indicates that the L-probe hybridization in each cycle is encoding for a specific reporter probe and it is also efficiently removed and replaced with another L-probe encoding for a different L-probe encoding for a different reporter probe.

The design of the L-probe hybridization method provides a general sequencing reaction with a decoding scheme that is both straightforward and highly flexible and results in the identification of genes of interest in situ. In the main design, an L-shaped detection probe can hybridize to the RCP, and a reporter probe is then allowed to hybridize and is subjected to imaging. The L-probes consists of a reporter probe binding site (20nt), a 2nt linker region and a RCP binding region (18nt) (FIG. 10). The RCP binding region is specific to a gene (i.e. complementary to the nucleotide barcode sequence in the RCP) and the reporter probe binding region is specific to the reporter probe that will be used in the decoding scheme during a cycle (FIG. 10). In total, 4 L-probes will be designed for each gene which will have an identical RCP binding region but will differ in their reporter probe binding region. Each L-probe will contain a reporter probe binding region which is complementary to a different reporter probe with a different fluorophore, such as Cy®3 (dye), Cy®5 (dye), Cy®7 (dye) and AF488 (Alexa Fluor® 488) (dye). Other fluorophores may be used possible depending on the need. These 4 L-probes can be extended to include 5 or more L-probes each decoding for a unique reporter probe binding site while all having the same RCP binding site. The sequencing reaction is initiated by hybridizing a pool of L-probes, each encoding for a unique gene, to the RCPs in the tissue section. A universal pool of reporter probes is then allowed to hybridize the bound L-probes. Roughly $\frac{1}{4}^{th}$ of these L-probes will encode for a Cy®3 (dye) reporter probe, $\frac{1}{4}^{th}$ will encode for a Cy®5 (dye) reporter probe, etc. as shown in FIG. 11. The tissue section is then imaged and the L-probes and reporter probe are removed. The second cycle is like the first cycle except that the L-probe pool is altered. While the L-probes still encode and bind to the same genes, the reporter probe binding sites in the L-probes are altered so that the L-probes encoding for a particular reporter probe in the first cycle might, but will not necessarily, encode for a different reporter probe in the second cycle. For example, an L-probe encoding for gene 1 might encode for the Cy®3 (dye) reporter probe in the first cycle but encode for the Cy®5 (dye) reporter probe in the second cycle. This means that the decoding scheme for gene 1 might be Cy®3 (dye) (cycle 1), Cy®5 (dye) (cycle 2), AF488 (Alexa Fluor® 488) (dye) (cycle 3), etc. . . . . While this design means that 4 L-probes per gene are required, totaling a large amount of probes needed, it also provides flexibility in how the L-probe pools for the decoding are created. It also allows multiple sequencing cycles to be conducted without the need to alter the RCP sequence. It may therefore be seen that the decoding power lies in the L-probe pool mix, rather than being directly encoded onto the RCP.

This design gives greater flexibility to change the decoding mechanism to include additional genes to the pool or reduce the number of genes in the pool. From FIGS. 12 and 13, it is clear that it is possible to control which reporter probe will be decoded for in which cycle. A requirement of this design is that the L-probes will need to be removed in order to make the L-probe recognition site available again on the RCP. This may seem quite a harsh treatment compared to other designs disclosed and claimed herein which may not require such harsh treatment to remove the signal. However, from FIGS. 12 and 13, this removal is seen to be very efficient.

Having the decoding mechanism based on the L-probe pool and not the RCP means only a 20nt recognition site is required on the RCP and not multiple binding sites which are specific to a specific reporter probe. This keeps the padlock probe relatively small and easier to work with. The added benefit to having the decoding mechanism being based on the L-probe pool is that we can decide the length of the decoding barcode. This can range from 1 to 6 or more cycles without any need of increasing the padlock probe size and without the need for additional reporter probes to be designed. This also means that in order to encode for 4 reporter probes, 4 L-probes per gene will need to be designed. If an additional reporter probe will be used in the decoding scheme, another L-probe will have to be designed per gene to encode for this reporter probe. This, however, does provide us with an extra level of flexibility to implement an extra "base" if many genes will need to be sequenced.

Example 4—Linear Strand Displacement with "Back and Forth" Arrangement and Additional Displacer Probes (2-LSD)

This is a second iteration of the LSD design that is discussed above. In the original LSD method, a subsequent detection probe in the form of an L-probe was used to displace the previous detection probe, without the need for chemical stripping. In the 2-LSD design, the barcode comprises 2 binding sites, that is 2 barcode positions (i.e. recognition sites for 2 detection probes), which are arranged so as to facilitate a "back and forth" decoding approach. In this arrangement, only 2 binding sites are required on the target nucleic acid molecule (here an RCP) in order to fully decode the barcode. The binding sites on the RCP comprise a 5 bp common region (these are different to each other, but common among all RCPs). Both binding sites also contain a 5 bp region that is unique both to each binding site and each RCP. Lastly, there is a 10 bp region that is common to both binding sites but unique for each RCP (FIG. 14). This overlapping region is a displacement site where the detection probes can displace each other in both directions. Thus, the barcode can be seen to comprise first and second barcode positions (corresponding to the first and second domains of the target nucleic acid sequence). The first barcode position (BC1) comprises first and second barcode subunits (2 and 3 in FIG. 14) and the second barcode position (BC2) comprises first and second barcode subunits (3 and 4 in FIG. 14) wherein the second subunit of BC1 overlaps with (is common with or shared) with the first subunit of BC2. 3 is thus the shared or overlapping barcode subunit, and 2 and 4 are unique barcode subunits which are unique to BC1 and BC2 respectively. Each barcode position (BC1 and BC2) also comprises its own adjacent common region, 1 and 5 respectively in FIG. 14. The common regions are the same for the first and second positions barcodes used in different targets (RCPs) but are different from each other within a given barcode. BC1 and BC2 together with their adjacent common region make up the binding site for a detection probe.

The detection probes used in the 2-LSD method are modified L-probes which have been designed to have 2 overhangs, that is they are U-probes as defined above. They are slightly different from the detection probes used in the original LSD method in two ways. The first is the addition of a 10 bp displacer toehold overhang that acts as a toehold region for a short displacer probe to bind. This displacer toehold overhang is common for all detection probes which bind to a specific binding site (barcode position with common region). The presence of this additional displacer toehold region on the detection probes allows for displacement to occur simultaneously on both sides of the detection probe; at the displacer toehold site, the detection probe can be displaced by a displacer probe, and at the other end of the binding site, the detection probe can be displaced by the subsequent detection probe (as in the original LSD method).

The second change is that the detection probes are designed to bind specifically either to "binding site 1" or "binding site 2" (FIG. 15). The detection probes need to be in a certain configuration when bound to the RCP, and need to be able to bind to the specific sequences in one of the 2 binding sites, so they are each designed to bind only to one or other of the binding sites.

As a typical sequencing workflow consist of 6 rounds of decoding, ie. 6 unique detection probes, the detection probes will be designed such that detection probes for cycles 1, 3 and 5 will bind binding site 1 and detection probes for cycles 2, 4 and 6 will bind to binding site 2. This means that a detection probe designed for cycle 2 will not be able to be used for cycle 5, for example.

The 2-LSD design removes the need to use chemical stripping to remove the detection probes. This is more gentle on the tissue samples which are being investigated, and allows the morphology of the sample to be preserved. The use of a "back-and-forth" design means that very similar binding sites to those used in the original LSD method can be used, thus retaining the size of the padlock probe (which is used to generate the RCP, and thus which contains a complementary copy of the barcode which appears in the RCP; in effect the barcode is coded into the padlock probe, and is copied into the RCP). In addition, the use of a common displacer toehold overhang region means that only 2 distinct displacer probes are required to displace all of the detection probes in the entire detection probe pool for all of the sequencing cycles. This reduces the costs of reagents, and makes the reaction more efficient.

Methods

Mouse Tissue Section Preparation

Mouse strain C57BL/6 at 30 days age (P30) was euthanized and the olfactory bulb was dissected via cryosectioning. Cryosectioning was performed on ThermoFisher cryostat, at 10 µm thickness. Sections were then adhered onto ThermoFisher Superfrost™ glass slides (coated glass slides) and stored at −70 C until processing.

RCA Generation In Situ

Fixation and Permeabilization

The tissue slide was removed from −70° C. storage and allowed to thaw for 5 min at room temperature (RT). Fixation was then performed by incubating the slides in 3.7% PFA in 1×DEPC-PBS at RT for 5 min. The slide was then washed in 1×DEPC-PBS for 1 min at RT. This ensured that the PFA was completely removed before moving to the permeabilization step. The tissue sections were then permeabilized using 0.1M HCl in DEPC-H2O for 1 min at RT and subsequently quickly washed twice in 1×DEPC-PBS. Following this, the slides were then dehydrated with an ethanol series in 70% and 100% ethanol for 2 min respectively before the slides are air-dried for 5 min at RT. A Secure Seal™ Chamber (Grace Bio Labs) (adhesive enclosures) are applied to each section and the sections were rehydrated with 1×DEPC-PBS-T before continuing with the reverse transcription step.

Reverse Transcription

Using CARTANA's Neurokit, 43.75 µl Reaction Mix (RM1), 1.25 µl of Enzyme 1 (RNase Inhibitor) and 5.00 µl of Enzyme 2 (Reverse Transcriptase) was added to each SecureSeal™ chamber (adhesive enclosure) and the samples were incubated in a humidity chamber at 37° C. overnight.

Probe Ligation

The reverse transcription was removed from the SecureSeal™ chambers (adhesive enclosures) and the slides were subjected to a post-fixation step using 3.7% PFA in DEPC-PBS for 30 min at RT. After the post-fixation step, the sections were quickly washed twice with DEPC-PBS-T. Using CARTANA's Neurokit, 36.0 µl Reaction Mix 2 (RM2), 4.0 µl of Enzyme 3 (RNase H), 5.0 µl of Enzyme 4 (Tth Ligase) and 100 nM of each padlock probe were added into each SecureSeal™ chamber (adhesive enclosure) and incubated at 37° C. for 30 min followed by a second incubation at 45° C. for 60 min. The ligation reaction mix was then removed from the SecureSeal™ chambers (adhesive enclosures) and the chambers were then washed twice with DEPC-PBS-T.

Rolling Circle Amplification

Using CARTANA's Neurokit, 43.0 µl of Reaction Mix 3 (RM3) and 5 µl of Enzyme 5 (φ29 Polymerase) was added to the SecureSeal™ chambers (adhesive enclosures) and incubated at either 37° C. for 3 hrs or at 30° C. overnight. This was followed by the removal of the amplification reaction mix, and a step of washing twice with DEPC-PBS-T. The SecureSeal™ chambers (adhesive enclosures) were then removed and the slides were then dehydrated with an ethanol series in 70% and 100% ethanol for 2 min respectively before the slides were air-dried for 5 min at RT. The sections were then able to be used for in situ sequencing using the LSD design.

In Situ Sequencing of RCPs in Tissue Sections Using the 2-LSD Design

Probe Design

The detection probes were designed to hybridize either to binding site 1 or binding site 2 on the RCP. The 2 designs were identical except for the orientation. The detection probe comprised a 10 bp displacer toehold overhang region which, combined with a 5 bp sequence in the RCP recognition domain, functioned as a generic toehold region common to all detection probes. The RCP binding region, comprising the aforementioned 5 bp toehold plus an additional 15 bp, spanned 20 bp and the reporter probe binding site was 20 bp in length. The detection probe had a GC content of 50%. For binding site 1, the displacer toehold overhang region was on the left and the reporter probe binding region was on the right of the RCP binding domain. For the detection probe binding to binding site 2, the reporter probe binding region was on the left side of the RCP binding domain and the displacer toehold overhang region was on the right.

The barcode design of the padlock probe comprised a 30 bp detection probe binding domain. It had 2 common regions at either end of the barcode, each being 5 bp in length. These common regions were different to each other but were common for all padlock probes, regardless of their targets. There were 2 unique regions that were 5 bp in length and were located next to the common regions. These unique regions were unique to each binding site. In the middle of the 30 bp detection probe binding region, there was a 10 bp binding region that was shared between the two binding sites. This ensured the ability for one detection probe to partially displace another detection probe. Each binding site consisted of 1 common region (5 bp), 1 unique region (5 bp) and the 10 bp common region, thus providing a 20 bp binding region for the detection probe to hybridize to.

Probe Hybridization

The sections were rehydrated with 1×PBS and the first probe mix was added at 100 nM in basic hybridization buffer (2.5×SSC+5-20% Formamide (depending on hybridization length)) and incubated at 1 hr at 37 C. The sections were then washed twice with basic washing buffer (1×PBS).

Detection Oligo Hybridization

After the detection probe hybridization, 100 nM detection oligo mix was added in basic hybridization buffer and allowed to hybridize for 30 min at 37 C. The sections were then washed twice with basic washing buffer before dehydrating the sections with an ethanol series in 70% and 100% ethanol for 2 min respectively before the slides were air-dried for 5 min at RT. 10 µl SlowFade™ Gold antifade reagent (Invitrogen) was then added to each section and covered with a coverslip. The slide was subjected to microscope imaging.

Displacement of Detection Probes Using the 2-LSD Approach

After imaging, the coverslip was removed, and the slide was subjected to an ethanol series in 70% and 100% ethanol for 2 min respectively before air-drying the slide for 5 min at RT to remove the mounting media. The sections were then rehydrated with 1×PBS. The second detection probe and a displacer strand mix was then added, both at 200 nM final concentration in displacement hybridization buffer (2.5× SSC, 0.05% Tween®-20 (nonionic detergent) and 5-20% Formamide conc. (depending on the hybridization length)). The sections were then incubated for 1 hr at 37 C and were subsequently washed with displacement wash buffer (1×DEPC-PBS-T and 20% formamide) twice for 10 min at room temperature. After the displacement reaction was complete, the sections were then subjected to DO mix hybridization as described above.

Results

Displacement of Detection Probes Under Different Buffer Conditions

The buffer used to displace one detection probe with the next in the sequencing cycle is key to an efficient and complete displacement during the 2-LSD method. Variations of a standard hybridization buffer were used in order to test which components are necessary to efficiently displace the detection probe. Three cycles of sequencing involving 2 displacement steps were performed in order to observe a color change as well as the recovery of the signal from the first cycle in the third cycle. All the buffer compositions tested were deemed successful at displacing the detection probes in cycle 2 and cycle 3 and lead to a switch from Cy®5 (dye) to Cy®3 (dye) and back to Cy®5 (dye). From the results, it was concluded that the displacement in the second cycle (from Cy®5 (dye) to Cy®3 (dye)) is less efficient for condition 3 (2.5×SSC+20% Formamide). This can be seen by analyzing the child:parent ratio (FIGS. 17A & B i), which indicates lower child:parent ratio then other conditions. From the base quality (FIGS. 17A & B iii), it can also be seen that condition 3 shows a lower quality overall compared to the other conditions.

The recovery of the signal in the Cy®5 (dye) channel (i.e. the third cycle) was lower in terms of the signal intensity (FIG. 17 B ii) and the base quality (FIG. 17 B iii) showing that the displacement of the second detection probe was not complete, but this signal was still well above background levels and could easily be identified. This finding was confirmed by the fact that the child:parent ratio (FIG. 17 B i) in the third cycle showed a full recovery of signal in the Cy®5 (dye) channel. A suitable displacement buffer could thus be selected from either 5× or 2.5×SSC supplemented with 0.05% Tween®-20 (nonionic detergent) and 20% Formamide. These results further indicated that the 2-LSD method is capable of displacing the detection probe currently hybridized by using a combination of a displacer strand and another detection probe.

2-LSD Cycling of 2 Displacement Cycles Using "Back-and-Forth" Method

Utilizing the optimal displacement buffer composition as outlined above, a 3 cycle 2-LSD set-up was used to investigate how efficiently the detection probes are displaced. FIG. 18A shows microscope images illustrating the switch in the detection of the detection probes from the Cy®5 (dye) to the Cy®3 (dye) and back again to the Cy®5 (dye) channel in their respective cycles. As a reference for the RCPs, a Cy®7 (dye)-tagged anchor was used together with DAPI as a nuclear counterstain. Throughout all 3 cycles, the switch between the channels can be observed quite clearly. FIG. 18B shows a line plot across three RCPs and indicates the grey values of the RCPs in the respective channels. Here, Cy®5 (dye) showed the highest signal in cycle 1 and completely disappears in cycle 2 only to be detected again in cycle 3, albeit at a slightly lower intensity. The signal in the Cy®3 (dye) channel was only quite clearly above background in cycle 2 which is where signal was to be expected. In both cycle 1 and cycle 3, the Cy®3 (dye) signal was at background levels. This indicates that during the 3 cycles, the channel that was expected to show signal was quite clearly distinguishable from other channels and those channels that should not show any signal can be seen to have signal near or below background levels. It can, therefore, be concluded that the 2-LSD design is able to successfully displace the detection probes and cycle through 2 positions in a "back-and-forth" approach.

The invention claimed is:

1. A method of detecting a target nucleic acid molecule in a sample, comprising:
 (a) contacting the sample with a padlock probe specific for the target molecule, wherein the padlock probe is circularized after hybridization to a target sequence in the target nucleic acid molecule, wherein the padlock probe comprises a nucleotide barcode sequence to identify the padlock probe, and wherein the circularized padlock probe is amplified by rolling circle amplification (RCA) to produce a rolling circle product (RCP), the RCP containing multiple complementary copies of the nucleotide barcode sequence;
 (b) assigning a signal code sequence specific to the target nucleic acid molecule,
  wherein the signal code sequence may be derived by interrogating the complementary copies of the nucleotide barcode sequence with sequential detection probes each yielding a signal and the signals together make up the signal code sequence, and wherein a complementary copy of the nucleotide barcode sequence comprises a first domain and a second domain, wherein a portion of the first domain overlaps with some but not all of the second domain;
 (c) contacting the RCP with a first detection probe to hybridize the first detection probe to the RCP, wherein the first detection probe comprises:
  (i) a recognition sequence complementary to the first domain and
  (ii) a first reporter;
 (d) detecting a signal from the first reporter, thereby obtaining a first signal code of the signal code sequence;
 (e) contacting the RCP with a second detection probe to hybridize the second detection probe to the RCP, wherein the second detection probe comprises:
  (i) a recognition sequence complementary to the second domain and
  (ii) a second reporter,
  wherein the second detection probe initiates a strand displacement reaction displacing the first detection probe hybridized to the first domain;

(f) detecting a signal from the second reporter, thereby obtaining a second signal code of the signal code sequence; and (g) contacting the RCP with additional detection probes to identify additional signal codes of the signal code sequence until sufficient signal codes have been identified to detect the nucleic acid molecule, wherein the additional detection probes have recognition sequences complementary to the first or second domain such that additional detection probes successively hybridize to the first or second domain and displace preceding detection probes hybridized thereto.

2. The method of claim 1, wherein the first domain is 5' to the second domain in the complementary copy of the nucleotide barcode sequence.

3. The method of claim 1, wherein the first domain is 3' to the second domain in the complementary copy of the nucleotide barcode sequence.

4. The method of claim 1, wherein the target sequence is in a native genomic DNA or in a naturally occurring RNA molecule, or in a cDNA, or in an amplification product generated from any of the foregoing nucleic acid molecules.

5. The method of claim 1, wherein the first domain and the second domain each comprises a first subunit and a second subunit, and wherein the second subunit from the first domain fully overlaps with the first subunit of the second domain.

6. The method of claim 5, wherein the complementary copy of the nucleotide barcode sequence comprises: (i) a first common region adjacent to the first subunit of the first domain, wherein the recognition sequence of the first detection probe comprises a sequence which is complementary to the first common region; and (ii) a second common region adjacent to the second subunit of the second domain, wherein the recognition sequence of the second detection probe comprises a sequence which is complementary to the second common region.

7. The method of claim 6, wherein the first detection probe, the second detection probe, and the additional detection probes each comprise a displacer toehold overhang region.

8. The method of claim 7, wherein all of the detection probes comprising a recognition sequence that is complementary to the first domain comprise a first displacer toehold overhang sequence, and all of the detection probes comprising a recognition sequence that is complementary to the second domain comprise a second displacer toehold overhang sequence.

9. The method of claim 8, wherein (g) further comprises contacting the RCP with either a first displacer probe which comprises a displacer toehold binding region complementary to the first displacer toehold overhang and a sequence complementary to the first common region; or a second displacer probe which comprises a displacer toehold binding region complementary to the second displacer toehold overhang and a sequence complementary to the second common region.

10. The method of claim 1, wherein the target sequence is a nucleotide barcode sequence provided within the target nucleic acid molecule.

11. The method of claim 1, wherein the target nucleic acid molecule is linked to an antibody.

12. The method of claim 1, wherein the first domain and the second domain each comprises a unique subunit.

13. The method of claim 1, wherein the reporter of each detection probe is a binding site for a reporter probe comprising a detectable label, said binding site being contained in an overhang region of the detection probe which does not hybridize to the RCP, and wherein the signal is detected from said label.

14. The method of claim 13, wherein the detectable label is a fluorophore.

15. The method of claim 14, wherein the signal code signal code sequence is a unique fluorophore sequence.

16. The method of claim 1, for detecting multiple different nucleic acid molecules present in the sample, wherein each different nucleic acid molecule is assigned a different signal code sequence and is detected using a specific padlock probe with a different nucleotide barcode sequence.

17. The method of claim 1, wherein the sample is a cell or a tissue sample on a solid substrate.

* * * * *

UNITED STATES PATENT AND TRADEMARK OFFICE
CERTIFICATE OF CORRECTION

| | |
|---|---|
| PATENT NO. | : 11,555,219 B2 |
| APPLICATION NO. | : 17/335931 |
| DATED | : January 17, 2023 |
| INVENTOR(S) | : Malte Kühnemund et al. |

It is certified that error appears in the above-identified patent and that said Letters Patent is hereby corrected as shown below:

In the Claims

At Column 62, Claim number 15, Line number 32:
"15. The method of claim 14, wherein the signal code signal code sequence is a unique fluorophore sequence."

Should read:
-- 15. The method of claim 14, wherein the signal code sequence is a unique fluorophore sequence. --

Signed and Sealed this
Twenty-first Day of March, 2023

Katherine Kelly Vidal
*Director of the United States Patent and Trademark Office*